US012571004B2

(12) United States Patent　(10) Patent No.: US 12,571,004 B2
Khvorova et al.　(45) **Date of Patent: \*Mar. 10, 2026**

(54) EXOSOMAL LOADING USING HYDROPHOBICALLY MODIFIED OLIGONUCLEOTIDES

(71) Applicant: University of Massachusetts, Boston, MA (US)

(72) Inventors: Anastasia Khvorova, Westborough, MA (US); Neil Aronin, Newtonville, MA (US); Marie Cecile Didiot, Worcester, MA (US); Reka Haraszti, Tubingen (DE)

(73) Assignee: University of Massachusetts, Boston, MA (US)

(\*) Notice: Subject to any disclaimer, the term of this patent is extended or adjusted under 35 U.S.C. 154(b) by 106 days.

This patent is subject to a terminal disclaimer.

(21) Appl. No.: 17/968,720

(22) Filed: Oct. 18, 2022

(65) Prior Publication Data

US 2023/0399659 A1　Dec. 14, 2023

Related U.S. Application Data

(63) Continuation of application No. 16/714,015, filed on Dec. 13, 2019, now Pat. No. 11,505,807, which is a continuation of application No. 15/304,943, filed as application No. PCT/US2015/026350 on Apr. 17, 2015, now Pat. No. 10,513,710.

(60) Provisional application No. 61/981,722, filed on Apr. 18, 2014.

(51) Int. Cl.
　*C12N 15/88*　(2006.01)
　*C12N 15/113*　(2010.01)

(52) U.S. Cl.
　CPC .......... *C12N 15/88* (2013.01); *C12N 15/1137* (2013.01); *A01K 2267/0337* (2013.01); *C12N 2310/11* (2013.01); *C12N 2310/14* (2013.01); *C12N 2310/141* (2013.01); *C12N 2310/311* (2013.01); *C12N 2310/313* (2013.01); *C12N 2310/315* (2013.01); *C12N 2310/3181* (2013.01); *C12N 2310/321* (2013.01); *C12N 2310/322* (2013.01); *C12N 2310/3231* (2013.01); *C12N 2310/351* (2013.01); *C12N 2310/3515* (2013.01); *C12N 2310/531* (2013.01)

(58) Field of Classification Search
　None
　See application file for complete search history.

(56) References Cited

U.S. PATENT DOCUMENTS

| | | | |
|---|---|---|---|
| 7,498,316 B2 | 3/2009 | Xu et al. | |
| 8,148,344 B2 | 4/2012 | Akinc et al. | |
| 10,513,710 B2 * | 12/2019 | Khvorova | C12N 15/1137 |
| 10,851,372 B2 | 12/2020 | Gibbings et al. | |
| 11,505,807 B2 * | 11/2022 | Khvorova | C12N 15/88 |
| 2005/0164254 A1 | 7/2005 | Bennett et al. | |
| 2007/0298118 A1 | 12/2007 | Lotvall et al. | |
| 2008/0125386 A1 | 5/2008 | Rana et al. | |
| 2011/0039914 A1 | 2/2011 | Pavco et al. | |
| 2012/0301433 A1 | 11/2012 | Lu et al. | |
| 2013/0018082 A1 | 1/2013 | McSwigen et al. | |
| 2013/0053426 A1 | 2/2013 | Seow et al. | |
| 2013/0131141 A1 | 5/2013 | Khvorova et al. | |
| 2013/0203837 A1 | 8/2013 | Zhang et al. | |
| 2015/0093433 A1 | 4/2015 | Leonard et al. | |
| 2016/0000710 A1 | 1/2016 | Gupta et al. | |
| 2017/0183686 A1 | 6/2017 | Khvorova et al. | |
| 2020/0283801 A1 | 9/2020 | Khvorova et al. | |

FOREIGN PATENT DOCUMENTS

| | | | |
|---|---|---|---|
| WO | 2007/126386 A1 | 11/2007 | |
| WO | 2010/033247 A2 | 3/2010 | |
| WO | 2010/119256 A1 | 10/2010 | |
| WO | 2010/129672 A1 | 11/2010 | |
| WO | 2011/119852 A1 | 9/2011 | |
| WO | WO-2011109698 A1 * | 9/2011 | A61K 31/7088 |
| WO | 2013/084000 A2 | 6/2013 | |
| WO | 2013/084001 A1 | 6/2013 | |
| WO | 2014/028493 A2 | 2/2014 | |

OTHER PUBLICATIONS

U.S. Appl. No. 15/304,943; Declaration under 37 CFR 1.132 of Anastasia Khvorova, Ph.D, pp. 1-11 (Year: 2016).*
Shtam et al. Cell Communication and Signaling 11: 1-10 (Year: 2013).*
Advirna, RNAi research and development company. Products. WayBackMachine. 1 page, retrieved Aug. 2022.
Alterman et al., Hydrophobically Modified siRNAs Silence Huntingtin mRNA in Primary Neurons and Mouse Brain. Mol Ther Nucleic Acids. Dec. 1, 2015;4:e266.
Alvarez-Erviti et al., Delivery of siRNA to the mouse brain by systemic injection of targeted exosomes. Nat Biotechnol. Apr. 2011;29(4):341-5.
Asai et al., Systemic delivery of small RNA using lipid nanoparticles. Biol Pharm Bull. 2014;37(2):201-5.
Bryniarski et al., Antigen-specific, antibody-coated, exosome-like nanovesicles deliver suppressor T-cell microRNA-150 to effector T cells to inhibit contact sensitivity. J Allergy Clin Immunol. Jul. 2013;132(1):170-81.
Byrne et al., Novel hydrophobically modified asymmetric RNAi compounds (sd-rxRNA) demonstrate robust efficacy in the eye. J Ocul Pharmacol Ther. Dec. 2013;29(10):855-64.

(Continued)

*Primary Examiner* — Brian Whiteman
(74) *Attorney, Agent, or Firm* — McCarter & English, LLP; Jill Mello; Yelena Margolin

(57) ABSTRACT

In one aspect, the invention relates to a method of loading exosomes with oligonucleotide cargo, by incubating an oligonucleotide comprising one or more hydrophobic modifications with a population of exosomes for a period of time sufficient to allow loading of the exosomes with the oligonucleotide. Exosomes loaded with hydrophobically modified oligonucleotide cargo, and uses thereof, are also provided.

24 Claims, 29 Drawing Sheets
(9 of 29 Drawing Sheet(s) Filed in Color)
Specification includes a Sequence Listing.

(56) References Cited

OTHER PUBLICATIONS

De Paula et al., Hydrophobization and bioconjugation for enhanced siRNA delivery and targeting. RNA. Apr. 2007;13 (4):431-56.

Debart et al., Chemical modifications to improve the cellular uptake of oligonucleotides. Curr Top Med Chem. 2007;7 (7):727-37.

Declaration of Assignment, EP 2011 0760232. 1 page, Sep. 11, 2013.

Duechler, Vehicles for Small Interfering RNA trasfection: Exosomes versus Synthetic Nanocarriers. RNA Nanotechnologiy. 2013;pp. 16-26.

El-Andaloussi et al., Exosome-mediated delivery of siRNA in vitro and in vivo. Nat Protoc. Dec. 2012;7 (12):2112-26.

El Andaloussi et al., Extracellular vesicles: biology and emerging therapeutic opportunities. Nat Rev Drug Discov. May 2013;12(5):347-57.

Gagnon et al., 10th Annual Meeting of the Oligonucleotide Therapeutics Society. Meeting Report. Nucleic Acid Therapeutics. 2014;24(6):428-434.

Haraszti et al., Optimized Cholesterol-siRNA Chemistry Improves Productive Loading onto Extracellular Vesicles. Mol Ther. Aug. 1, 2018;26(8):1973-1982.

Kooijmans et al., Electroporation-induced siRNA precipitation obscures the efficiency of siRNA loading into extracellular vesicles. J Control Release. Nov. 28, 2013;172(1):229-238.

Kooijmans et al., Exosome mimetics: a novel class of drug delivery systems. Int J Nanomedicine. 2012;7:1525-41.

Lee et al., Exosomes and microvesicles: extracellular vesicles for genetic information transfer and gene therapy. Hum Mol Genet. Oct. 15, 2012;21(R1):R125-34.

Lou, No place like exosome. SciBX, Science-Business-eXchange. 2 pages, (2011).

Marcus et al., FedExosomes: Engineering Therapeutic Biological Nanoparticles that Truly Deliver. Pharmaceuticals (Basel). 2013;6(5):659-80.

Ohno et al., Systemically injected exosomes targeted to EGFR deliver antitumor microRNA to breast cancer cells. Mol Ther. Oct. 2, 2012;21(1):185-91.

Okumus et al., Vesicle encapsulation studies reveal that single molecule ribozyme heterogeneities are intrinsic. Biophys J. Oct. 2004; 87(4):2798-806.

O'Loughlin et al., Functional Delivery of Lipid-Conjugated siRNA by Extracellular Vesicles. Mol Ther. Jul. 5, 2017;25 (7):1580-1587.

Pfeiffer et al., Bivalent cholesterol-based coupling of oligonucletides to lipid membrane assemblies. J Am Chem Soc. Aug. 25, 2004;126(33):10224-5.

Pi et al., Nanoparticle orientation to control RNA loading and ligand display on extracellular vesicles for cancer regression. Nat Nanotechnol. Jan. 2018;13(1):82-89.

Qiagen, RNAi Human/Mouse Starter Kit Handbook, For RNAi in human and mouse cells, Third Edition. www.qiagen.com. 48 pages, May 2009.

Raouane et al., Lipid conjugated oligonucleotides: a useful strategy for delivery. Bioconjug Chem. Jun. 20, 2012;23 (6):1091-104.

Scholz et al., Therapeutic plasmid DNA versus siRNA delivery: common and different tasks for synthetic carriers. J Control Release. Jul. 20, 2012;161(2):554-65.

Schroeder et al., Lipid-based nanotherapeutics for siRNA delivery. J Intern Med. Jan. 2010;267(1):9-21.

Schwendener et al., Liposome Formulations of Hydrophobic Drugs. Liposomes, Methods in Molecular Biology. V. Weissig (Ed.) Humana Press. Chapter 8, pp. 129-138, (2010).

Shen, Exosomes: a new hope in RNAi delivery. BioTechniques. Retrieved online at: http://www.biotechniques.com/news/Exosomes-a-new-hope-in-RNAi-delivery. 4 pages, Jun. 2, 2011.

Stremersch et al., Hijacking nature's own communication system: evaluation of extracellular vesicles as a sirna delivery vehicle. NanoBio&Med. pp. 82-83, Nov. 18-21, 2014.

Sun et al., A novel nanoparticle drug delivery system: the anti-inflammatory activity of curcumin is enhanced when encapsulated in exosomes. Mol Ther. Sep. 2010; 18(9):1606-14.

Suntres et al., Therapeutic Uses of Exosomes. Exosomes and Microvesicles, 2013;1(5):1-8.

The Massachusetts Technology Transfer Center. The Eighth Early-Stage Life Sciences Technology Conference. Merck Research Laboratories. 72 pages, Apr. 12, 2012.

Vader et al., New considerations in the preparation of nucleic acid-loaded extracellular vesicles. Ther Deliv. Feb. 2014;5(2):105-7.

Wahlgren et al., Plasma exosomes can deliver exogenous short interfering RNA to monocytes and lymphocytes. Nucleic Acids Res. Sep. 1, 2012;40(17):e130, 12 pages.

Wood et al., Exosomes and the blood-brain barrier: implications for neurological diseases. Ther Deliv. Sep. 2011;2 (9):1095-9.

Yang et al., Efficient cytosolic delivery of siRNA using HDL-mimicking nanoparticles. Small. Mar. 7, 2011;7(5):568-73.

European Search Report for Application No. EP15779678.0, dated Aug. 4, 2017, 9 pages.

Extended European Search Report for Application No. 20167203.7, dated Dec. 22, 2023, 7 pages.

International Preliminary Report on Patentability for Application No. PCT/US2015/026350, dated Oct. 27, 2016, 11 pages.

International Search Report and Written Opinion for Application No. PCT/US2015/026350, dated Aug. 17, 2015.

* cited by examiner 011417 extruded exosomes_005
77413 f2 sample 1 em 1/17/14 sample # 1

500 nm

HV=90.0kV
Direct Mag: 40000x
AMT Camera System

+ biotin hsiRNA + streptavidin/gold 500 nm hsiRNA Passive Uptake hsiRNA (CY3)

Exosome Alone Uptake

Exosomes (PKH67)

Exosome-Mediated hsiRNA Uptake hsiRNA-Exosomes

Exosome-Mediated hsiRNA Uptake hsiRNA-Exosomes

Cholesterol
TEG linker
Phosphorothioate
5'-Phosphate
2'-Fluoro
2'-O-Methyl

Unformulated
hsiRNA hsiRNA-loaded
exosomes siRNA    hsiRNA

FIG. 12A
| | Unloaded exosomes | hsiRNA-loaded exosomes |
|---|---|---|
| Particles number (µl) | $10^9$ | $10^9$ |
| hsiRNAs (mol/exosome) | - | 1000-3000 |
| Mean size (nm) | 141 | 145 |
| Zeta potential (mV) | -13 | -32 |
FIG. 12B
Unloaded exosomes          hsiRNA-loaded exosomes
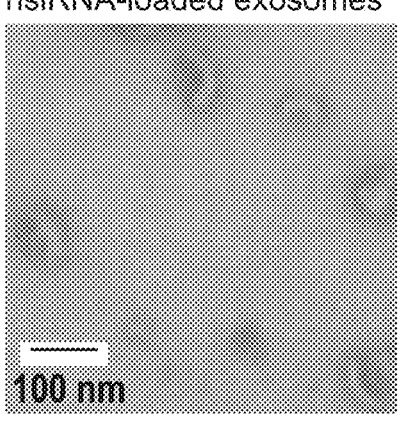
FIG. 12C
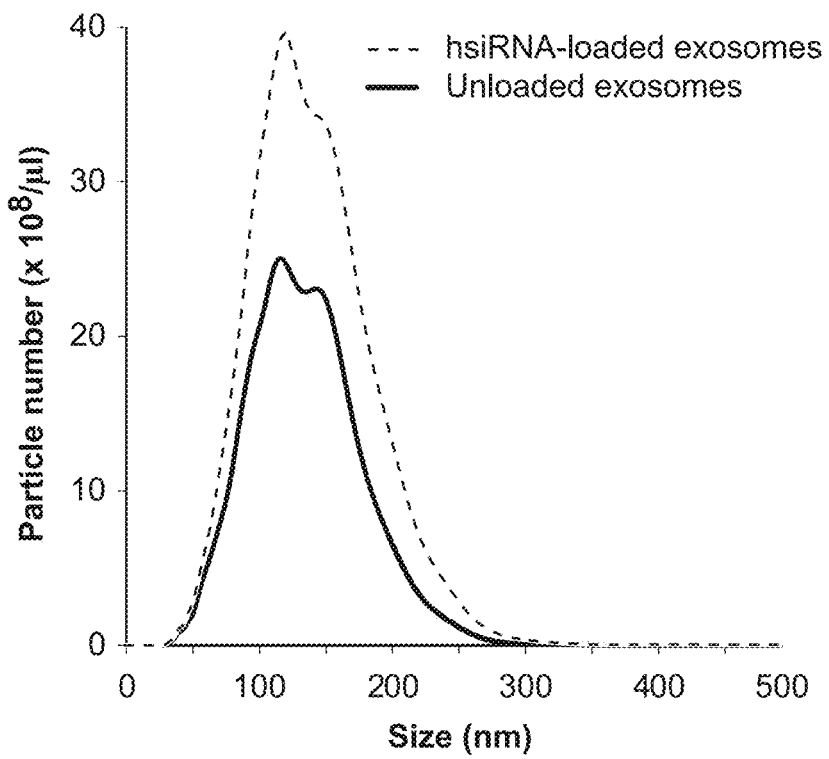

Time (hours)

| Dunn's multiple comparisons test | Mean rank difference | Significance | Adjusted P value |
|---|---|---|---|
| CSF vs. hsiRNA-htt | 21.89 | ns | 0.5162 |
| CSF vs. Exosomes | -10.43 | ns | > 0.9999 |
| CSF vs. NTC-Exosomes | 8.856 | ns | > 0.9999 |
| CSF vs. 3.5 ug CL | 54.68 | ** | 0.0061 |
| CSF vs. 3.5 ug IL | 62.46 | *** | 0.001 |
| CSF vs. 7 ug CL | 41.89 | *** | 0.0044 |
| CSF vs. 7 ug IL | 68.9 | *** | 0.0002 |

SEQUENCE LISTING

```
Sequence total quantity: 6
SEQ ID NO: 1              moltype = RNA   length = 13
FEATURE                   Location/Qualifiers
source                    1..13
                          mol_type = other RNA
                          organism = synthetic construct
                          note = Description of Artificial Sequence: Synthetic
                          oligonucleotide
modified_base             1
                          mod_base = OTHER
                          note = 2'-O-methyl nucleotide
modified_base             2
                          mod_base = OTHER
                          note = 2'-O-methyl nucleotide
modified_base             6
                          mod_base = OTHER
                          note = 2'-O-methyl nucleotide
modified_base             8
                          mod_base = OTHER
                          note = 2'-O-methyl nucleotide
modified_base             11
                          mod_base = OTHER
                          note = misc_feature - 2'-O-methyl phosphorothioate linkage
modified_base             12
                          mod_base = OTHER
                          note = misc_feature - 2'-O-methyl phosphorothioate linkage
modified_base             13
                          mod_base = OTHER
                          note = 2'-O-methyl triethylene glycol cholesterol modified
                          nucleotide
SEQUENCE: 1
acaaatacga tta                                                        13
```

```
SEQ ID NO: 2             moltype = RNA  length = 19
FEATURE                  Location/Qualifiers
source                   1..19
                         mol_type = other RNA
                         organism = synthetic construct
                         note = Description of Artificial Sequence: Synthetic
                          oligonucleotide
modified_base            1
                         mod_base = OTHER
                         note = 5' Phosphate 2'-O-methyl nucleotide
modified_base            4
                         mod_base = OTHER
                         note = 2'-Fluoro nucleotide
modified_base            5
                         mod_base = OTHER
                         note = 2'-Fluoro nucleotide
modified_base            7
                         mod_base = OTHER
                         note = 2'-Fluoro nucleotide
modified_base            9
                         mod_base = OTHER
                         note = 2'-Fluoro nucleotide
modified_base            10
                         mod_base = OTHER
                         note = 2'-Fluoro nucleotide
modified_base            11
                         mod_base = OTHER
                         note = 2'-Fluoro nucleotide
modified_base            13
                         mod_base = OTHER
                         note = misc_feature - internucleotide phosphorothioate
                          linkage
modified_base            14
                         mod_base = OTHER
                         note = misc_feature - 2'-O-methyl phosphorothioate linkage
modified_base            15
                         mod_base = OTHER
                         note = misc_feature - internucleotide phosphorothioate
                          linkage
modified_base            16
                         mod_base = OTHER
                         note = misc_feature - internucleotide phosphorothioate
                          linkage
modified_base            17
                         mod_base = OTHER
                         note = misc_feature - 2'-O-methyl phosphorothioate linkage
modified_base            18
                         mod_base = OTHER
                         note = misc_feature - 2'-O-methyl phosphorothioate linkage
SEQUENCE: 2
taatcgtatt tgtcaatca                                                  19

SEQ ID NO: 3             moltype = RNA  length = 15
FEATURE                  Location/Qualifiers
source                   1..15
                         mol_type = other RNA
                         organism = synthetic construct
                         note = Description of Artificial Sequence: Synthetic
                          oligonucleotide
modified_base            1
                         mod_base = OTHER
                         note = 2'-O-methyl nucleotide
modified_base            2
                         mod_base = OTHER
                         note = 2'-O-methyl nucleotide
modified_base            4
                         mod_base = OTHER
                         note = 2'-O-methyl nucleotide
modified_base            12
                         mod_base = OTHER
                         note = 2'-O-methyl nucleotide
modified_base            13
                         mod_base = OTHER
                         note = misc_feature - 2'-O-methyl phosphorothioate linkage
modified_base            14
                         mod_base = OTHER
                         note = misc_feature - 2'-O-methyl phosphorothioate linkage
modified_base            15
```

-continued

```
                         mod_base = OTHER
                         note = 2'-O-methyl nucleotide
SEQUENCE: 3
cagtaaagag attaa                                                 15

SEQ ID NO: 4            moltype = RNA  length = 20
FEATURE                 Location/Qualifiers
source                  1..20
                        mol_type = other RNA
                        organism = synthetic construct
                        note = Description of Artificial Sequence: Synthetic
                         oligonucleotide
modified_base           1
                        mod_base = OTHER
                        note = 5' Phosphate 2'-O-methyl nucleotide
modified_base           2
                        mod_base = OTHER
                        note = 2'-Fluoro nucleotide
modified_base           5
                        mod_base = OTHER
                        note = 2'-Fluoro nucleotide
modified_base           6
                        mod_base = OTHER
                        note = 2'-Fluoro nucleotide
modified_base           7
                        mod_base = OTHER
                        note = 2'-Fluoro nucleotide
modified_base           8
                        mod_base = OTHER
                        note = 2'-Fluoro nucleotide
modified_base           9
                        mod_base = OTHER
                        note = 2'-Fluoro nucleotide
modified_base           10
                        mod_base = OTHER
                        note = 2'-Fluoro nucleotide
modified_base           11
                        mod_base = OTHER
                        note = 2'-Fluoro nucleotide
modified_base           13
                        mod_base = OTHER
                        note = 2'-Fluoro nucleotide
modified_base           14
                        mod_base = OTHER
                        note = misc_feature - 2'-Fluoro phosphorothioate linkage
modified_base           15
                        mod_base = OTHER
                        note = misc_feature - internucleotide phosphorothioate
                         linkage
modified_base           16
                        mod_base = OTHER
                        note = misc_feature - internucleotide phosphorothioate
                         linkage
modified_base           17
                        mod_base = OTHER
                        note = misc_feature - 2'-Fluoro phosphorothioate linkage
modified_base           18
                        mod_base = OTHER
                        note = misc_feature - internucleotide phosphorothioate
                         linkage
modified_base           19
                        mod_base = OTHER
                        note = misc_feature - 2'-Fluoro phosphorothioate linkage
SEQUENCE: 4
ttaatctctt tactgatata                                            20

SEQ ID NO: 5            moltype = RNA  length = 15
FEATURE                 Location/Qualifiers
source                  1..15
                        mol_type = other RNA
                        organism = synthetic construct
                        note = Description of Artificial Sequence: Synthetic
                         oligonucleotide
modified_base           1
                        mod_base = OTHER
                        note = 2'-O-methyl nucleotide
modified_base           2
                        mod_base = OTHER
                        note = 2'-O-methyl nucleotide
```

-continued

```
modified_base       4
                    mod_base = OTHER
                    note = 2'-O-methyl nucleotide
modified_base       12
                    mod_base = OTHER
                    note = 2'-O-methyl nucleotide
modified_base       13
                    mod_base = OTHER
                    note = misc_feature - 2'-O-methyl phosphorothioate linkage
modified_base       14
                    mod_base = OTHER
                    note = misc_feature - 2'-O-methyl phosphorothioate linkage
modified_base       15
                    mod_base = OTHER
                    note = 2'-O-methyl triethylene glycol cholesterol modified
                     nucleotide
SEQUENCE: 5
cagtaaagag attaa                                                          15

SEQ ID NO: 6        moltype = RNA   length = 20
FEATURE             Location/Qualifiers
source              1..20
                    mol_type = other RNA
                    organism = synthetic construct
                    note = Description of Artificial Sequence: Synthetic
                     oligonucleotide
modified_base       1
                    mod_base = OTHER
                    note = 5' Phosphate 2'-O-methyl nucleotide
modified_base       2
                    mod_base = OTHER
                    note = 2'-Fluoro nucleotide
modified_base       5
                    mod_base = OTHER
                    note = 2'-Fluoro nucleotide
modified_base       6
                    mod_base = OTHER
                    note = 2'-Fluoro nucleotide
modified_base       7
                    mod_base = OTHER
                    note = 2'-Fluoro nucleotide
modified_base       8
                    mod_base = OTHER
                    note = 2'-Fluoro nucleotide
modified_base       9
                    mod_base = OTHER
                    note = 2'-Fluoro nucleotide
modified_base       10
                    mod_base = OTHER
                    note = 2'-Fluoro nucleotide
modified_base       11
                    mod_base = OTHER
                    note = 2'-Fluoro nucleotide
modified_base       13
                    mod_base = OTHER
                    note = 2'-Fluoro nucleotide
modified_base       14
                    mod_base = OTHER
                    note = misc_feature - 2'-Fluoro phosphorothioate linkage
modified_base       15
                    mod_base = OTHER
                    note = misc_feature - internucleotide phosphorothioate
                     linkage
modified_base       16
                    mod_base = OTHER
                    note = misc_feature - internucleotide phosphorothioate
                     linkage
modified_base       17
                    mod_base = OTHER
                    note = misc_feature - 2'-Fluoro phosphorothioate linkage
```

-continued

```
modified_base        18
                     mod_base = OTHER
                     note = misc_feature - internucleotide phosphorothioate
                      linkage
modified_base        19
                     mod_base = OTHER
                     note = misc_feature - 2'-Fluoro phosphorothioate linkage
SEQUENCE: 6
ttaatctctt tactgatata                                                  20
```

EXOSOMAL LOADING USING HYDROPHOBICALLY MODIFIED OLIGONUCLEOTIDES

RELATED APPLICATIONS

This application is a Continuation Application of U.S. patent application Ser. No. 16/714,015, filed on Dec. 13, 2019; which, in turn, is a Continuation Application of U.S. patent application Ser. No. 15/304,943, filed on Oct. 18, 2016, now U.S. Pat. No. 10,513,710, issued on Dec. 24, 2019; which is a 35 U.S.C. § 371 national stage filing of International Patent Application No. PCT/US2015/026350, filed on Apr. 17, 2015; which claims priority to U.S. Provisional Patent Application No. 61/981,722, filed on Apr. 18, 2014. The entire contents of each of the foregoing applications are incorporated herein by reference.

GOVERNMENT SUPPORT

This invention was made with government support under grant number TR000888 awarded by the National Institutes of Health. The government has certain rights in the invention.

SEQUENCE LISTING

The instant application contains a Sequence Listing which has been submitted electronically in XML format and is hereby incorporated by reference in its entirety. Said XML copy, created on Feb. 22, 2023, is named 122274-14004_SL.xml and is 44,808 bytes in size.

BACKGROUND OF THE INVENTION

Exosomes are extracellular particles produced by cells which can effectively transfer a variety of molecules, including small ribonucleic acids (RNAs), from cell to cell. Exosomes have been used as delivery vehicles to transfer synthetic small RNAs, e.g., small interfering RNAs (siR-NAs), to cells and tissues of interest in a proficient manner. Currently, however, the commercial potential of exosomes as delivery vehicles is minimal, due primarily to highly inefficient and non-scalable methods used for loading synthetic nucleic acids into exosomes.

SUMMARY OF THE INVENTION

Current methods of loading exosomes with nucleic acid cargo include electroporation, or transfection with cationic lipid reagents. Other methods include loading by ultracentrifugation. Each of these methods results in very low loading efficiency, where only a small fraction of added oligonucleotide molecules are transferred to exosomes. For example, one laboratory reported a loading efficiency using ultracentrifugation of 1 molecule of siRNA per 1000 exosomes.

New methods of loading exosomes with nucleic acid cargo are described herein. These methods are based, at least in part, on the discovery that introduction of a hydrophobic modification into an oligonucleotide facilitates exosomal loading. Accordingly, in some embodiments, the present invention relates to improved methods of loading exosomes with nucleic acid cargo. In other embodiments, the invention relates to exosomes loaded with nucleic acid cargo, in which the nucleic acid molecules contain one or more hydrophobic modifications. In other embodiments, the invention relates to the use of exosomes loaded with hydrophobically-modified nucleic acid cargo as delivery vehicles, e.g., for delivery of small oligonucleotides to cells or tissues.

Accordingly, in one aspect, the invention relates to a method of loading exosomes with oligonucleotide cargo, by incubating an oligonucleotide comprising one or more hydrophobic modifications with a population of exosomes. The hydrophobically modified oligonucleotide and the population of exosomes are incubated for a period of time sufficient to allow loading of the exosomes with the oligonucleotide. In preferred embodiments, the method takes place in the absence of electroporation, cationic liposome transfection reagents, and/or ultracentrifugation.

In another aspect, the invention provides a method of loading exosomes with oligonucleotide cargo, consisting essentially of incubating an oligonucleotide comprising one or more hydrophobic modifications with a population of exosomes.

The methods described herein are highly efficient and easily scalable, and allow the rapid production of oligonucleotide-loaded exosomes in quantities needed for therapeutic administration.

In certain embodiments of the foregoing aspects, loading of the exosomes with the oligonucleotide occurs in 30 minutes or less, e.g., 5 minutes or less. In some embodiments, loading of the exosomes occurs in 30 minutes, 20 minutes, 15 minutes, 10 minutes, 5 minutes, or 1 minute.

The methods described herein allow exosomes to be loaded with oligonucleotide cargo at efficiencies that were not achievable using traditional methods. Accordingly, in one embodiment, at least 80% of the exosomes incubated with an oligonucleotide comprising one or more hydrophobic modifications are loaded with the oligonucleotide. In a preferred embodiment, at least 90% of the exosomes incubated with an oligonucleotide comprising one or more hydrophobic modifications are loaded with the oligonucleotide. In exemplary embodiments, at least 91%, at least 92%, at least 93%, at least 94%, at least 95%, at least 96%, at least 97%, at least 98% or more of the exosomes incubated with an oligonucleotide comprising one or more hydrophobic modifications are loaded with the oligonucleotide. In one embodiment at least 99% of the exosomes incubated with an oligonucleotide comprising one or more hydrophobic modifications are loaded with the oligonucleotide.

The methods described herein also allow exosomes to be loaded with larger quantities of oligonucleotide cargo than was achievable using traditional methods. Accordingly, in one embodiment, exosomes are loaded with an average of at least 500 hydrophobically modified oligonucleotides per exosome, e.g., at least 600, at least 700, at least 800, at least 900, at least 1000, at least 1200, at least 1500, at least 2000, at least 2500, at least 3000 or more hydrophobically modified oligonucleotides per exosome. In one embodiment, exosomes are loaded with an average of about 500-3000 hydrophobically modified oligonucleotides per exosome. In another embodiment, exosomes are loaded with an average of about 500-1000 hydrophobically modified oligonucleotides per exosome. In another embodiment, exosomes are loaded with an average of about 1000-1500 hydrophobically modified oligonucleotides per exosome. In another embodiment, exosomes are loaded with an average of about 1000-3000 hydrophobically modified oligonucleotides per exosome. In another embodiment, exosomes are loaded with up to about 3000 hydrophobically modified oligonucleotides per exosome.

In preferred embodiments, the oligonucleotide is a synthetic oligonucleotide. In some embodiments, the oligonucleotide is a siRNA, siRNA-GalNAc, antisense RNA, LNA, hairpin siRNA, PMO, miRNA, miRNA inhibitor, or a combination thereof. In an exemplary embodiment, the oligonucleotide is siRNA. In another embodiment, the oligonucleotide is miRNA.

In certain embodiments of the foregoing aspects, the hydrophobic modification increases the hydrophobicity of the oligonucleotide by at least about 2 orders of magnitude relative to unmodified oligonucleotide.

In certain embodiments, the hydrophobic modification is a backbone modification, a sugar modification (e.g., a ribose modification), a base modification, or a combination thereof. Backbone modifications can include, in some embodiments, phosphorothioate modifications, phosphorodithioate modifications, p-ethoxy modifications, methylphosphonate modifications, methylphosphorothioate modifications, alkyl- and aryl-phosphate modifications, alkylphosphotriester modifications, peptide nucleic acid (PNA) modifications, and/or locked nucleic acid (LNA) modifications. Ribose modifications can include, in some embodiments, 2'O-Methyl, 2'Methoxy-ethyl, 2'Fluor, or 2'FANA. Base modifications can include, in some embodiments, phenyl, naphthyl, or isobutyl. In addition to increasing the hydrophobic character of oligonucleotide cargo, the foregoing modifications increase the stability of the oligonucleotide cargo in the presence of exosomes and make the oligonucleotide cargo resistant to degradation. In some embodiments, at least 30% of the nucleotides in the oligonucleotide contain one or more backbone modifications, sugar modifications, and/or base modifications. For example, at least 30%, at least 35%, at least 40%, at least 45%, at least 50%, at least 55%, at least 60%, at least 65% or more of the nucleotides in the oligonucleotide cargo can contain one or more backbone modifications, sugar modifications, and/or base modifications. In an exemplary embodiment, at least 50% of the nucleotides in the oligonucleotide contain one or more backbone modifications, sugar modifications, and/or base modifications.

In certain embodiments, the oligonucleotide can be conjugated to one or more hydrophobic moieties. For example, in some embodiments the hydrophobic moiety can be a sterol, GM1, a lipid, a vitamin, a small molecule, or a peptide, or a combination thereof. In an exemplary embodiment, the oligonucleotide cargo is conjugated to a sterol, e.g., cholesterol. In another exemplary embodiment, the oligonucleotide cargo is conjugated to GM1. In another exemplary embodiment, the oligonucleotide cargo is conjugated to myristic acid, or a derivative thereof.

In exemplary embodiments, the oligonucleotide cargo is stabilized by incorporation of one or more backbone modifications, sugar modifications, and/or base modifications as described herein, and additionally is conjugated to a hydrophobic moiety. For example, in one embodiment, the oligonucleotide cargo contains one or more backbone modifications, sugar modifications, and/or base modifications to at least 30%, at least 35%, at least 40%, at least 45%, at least 50%, at least 55%, at least 60%, at least 65% or more of the nucleotides, and further is conjugated to a hydrophobic moiety, e.g., a sterol, GM1, a lipid, a vitamin, a small molecule, or a peptide, or a combination thereof. In an exemplary embodiment, the oligonucleotide cargo is conjugated to a sterol, e.g., cholesterol. In another exemplary embodiment, the oligonucleotide cargo is conjugated to GM1. In another exemplary embodiment, the oligonucleotide cargo is conjugated to myristic acid, or a derivative thereof. In one embodiment, the oligonucleotide cargo is an siRNA that is modified as depicted in FIG. 10.

In certain embodiments, the exosomes can be derived from cultured cells. In exemplary embodiments, the exosomes can be derived from dendritic cells (DC), B cells, T cells, mast cells, epithelial cells, stem cells, neuronal cells, or tumor cells, or combinations thereof. In other embodiments, the exosomes can be derived from immature dendritic cells or induced pluripotent stem cells (iPS cells). In other embodiments, the exosomes are derived from neuronal cells. Alternatively, in some embodiments, the exosomes are synthetic exosomes.

In some embodiments, the exosomes can contain a targeting peptide, for example, a targeting peptide that directs the exosomes to neuronal cells.

In some embodiments, exosomes are purified after loading with hydrophobically modified oligonucleotide to separate the exosomes from unloaded oligonucleotide. In some embodiments, exosomes can be purified by ultrafiltration. In other embodiments, the exosomes can be purified by differential centrifugation.

In certain embodiments, the oligonucleotide directs the silencing of a mutant huntingtin gene or a mutant SOD1 gene. For example, in some embodiments, the oligonucleotide is an siRNA targeting a mutant huntingtin gene or a mutant SOD1 gene.

In another aspect, the invention provides compositions comprising exosomes loaded with hydrophobically modified oligonucleotide, whereby the compositions are produced by way of any of the foregoing methods. For example, in one embodiment, the invention provides a composition comprising exosomes loaded with hydrophobically modified oligonucleotide, wherein the exosomes are loaded by incubating an oligonucleotide comprising one or more hydrophobic modifications with a population of exosomes for a period of time sufficient to allow loading of the exosomes with the oligonucleotide.

In another aspect, the invention provides a composition comprising a plurality of exosomes loaded with an oligonucleotide comprising one or more hydrophobic modifications.

In some embodiments, at least 80% of the exosomes are loaded with the hydrophobically modified oligonucleotide. In a preferred embodiment, at least 90% of the exosomes are loaded with the hydrophobically modified oligonucleotide. In exemplary embodiments, at least 91%, at least 92%, at least 93%, at least 94%, at least 95%, at least 96%, at least 97%, at least 98% or more of the exosomes are loaded with the hydrophobically modified oligonucleotide. In one embodiment at least 99% of the exosomes are loaded with the hydrophobically modified oligonucleotide.

In other embodiments, the foregoing compositions contain exosomes that are loaded with an average of at least 500 hydrophobically modified oligonucleotides per exosome, e.g., at least 600, at least 700, at least 800, at least 900, at least 1000, at least 1200, at least 1500, at least 2000, at least 2500, at least 3000 or more hydrophobically modified oligonucleotides per exosome. In one embodiment, the exosomes contain an average of about 500-3000 hydrophobically modified oligonucleotides per exosome. In another embodiment, exosomes contain an average of about 500-1000 hydrophobically modified oligonucleotides per exosome. In another embodiment, exosomes contain an average of about 1000-1500 hydrophobically modified oligonucleotides per exosome. In another embodiment, exosomes contain an average of about 1000-3000 hydrophobically modified oligonucleotides per exosome. In another embodiment, exosomes contain up to about 3000 hydrophobically modified oligonucleotides per exosome.

In preferred embodiments, the oligonucleotide is a synthetic oligonucleotide. In some embodiments, the oligonucleotide is a siRNA, siRNA-GalNAc, antisense RNA, LNA, hairpin siRNA, PMO, miRNA, miRNA inhibitor, or a combination thereof. In an exemplary embodiment, the oligonucleotide is siRNA. In another embodiment, the oligonucleotide is miRNA.

In certain embodiments of the foregoing aspects, the hydrophobic modification increases the hydrophobicity of the oligonucleotide by at least about 2 orders of magnitude relative to unmodified oligonucleotide.

In certain embodiments, the hydrophobic modification is a backbone modification, a sugar modification (e.g., a ribose modification), a base modification, or a combination thereof. Backbone modifications can include, in some embodiments, phosphorothioate modifications, phosphorodithioate modifications, p-ethoxy modifications, methylphosphonate modifications, methylphosphorothioate modifications, alkyl- and aryl-phosphate modifications, alkylphosphotriester modifications, peptide nucleic acid (PNA) modifications, and/or locked nucleic acid (LNA) modifications. Ribose modifications can include, in some embodiments, 2'O-Methyl, 2'Methoxy-ethyl, 2'Fluor, or 2'FANA. Base modifications can include, in some embodiments, phenyl, naphthyl, or isobutyl. In addition to increasing the hydrophobic character of oligonucleotide cargo, the foregoing modifications increase the stability of the oligonucleotide cargo in the presence of exosomes and make the oligonucleotide cargo resistant to degradation. In some embodiments, at least 30% of the nucleotides in the oligonucleotide contain one or more backbone modifications, sugar modifications, and/or base modifications. For example, at least 30%, at least 35%, at least 40%, at least 45%, at least 50%, at least 55%, at least 60%, at least 65% or more of the nucleotides in the oligonucleotide cargo can contain one or more backbone modifications, sugar modifications, and/or base modifications. In an exemplary embodiment, at least 50% of the nucleotides in the oligonucleotide contain one or more backbone modifications, sugar modifications, and/or base modifications.

In certain embodiments, the oligonucleotide can be conjugated to one or more hydrophobic moieties. For example, in some embodiments the hydrophobic moiety can be a sterol, GM1, a lipid, a vitamin, a small molecule, or a peptide, or a combination thereof. In an exemplary embodiment, the oligonucleotide cargo is conjugated to a sterol, e.g., cholesterol. In another exemplary embodiment, the oligonucleotide cargo is conjugated to GM1. In another exemplary embodiment, the oligonucleotide cargo is conjugated to myristic acid, or a derivative thereof.

In exemplary embodiments, the oligonucleotide cargo is stabilized by incorporation of one or more backbone modifications, sugar modifications, and/or base modifications as described herein, and additionally is conjugated to a hydrophobic moiety. For example, in one embodiment, the oligonucleotide cargo contains one or more backbone modifications, sugar modifications, and/or base modifications to at least 30%, at least 35%, at least 40%, at least 45%, at least 50%, at least 55%, at least 60%, at least 65% or more of the nucleotides, and further is conjugated to a hydrophobic moiety, e.g., a sterol, GM1, a lipid, a vitamin, a small molecule, or a peptide, or a combination thereof. In an exemplary embodiment, the oligonucleotide cargo is conjugated to a sterol, e.g., cholesterol. In another exemplary embodiment, the oligonucleotide cargo is conjugated to GM1. In another exemplary embodiment, the oligonucleotide cargo is conjugated to myristic acid, or a derivative thereof. In one embodiment, the oligonucleotide cargo is an siRNA that is modified as depicted in FIG. 10.

In certain embodiments, the exosomes can be derived from cultured cells. In exemplary embodiments, the exosomes can be derived from dendritic cells (DC), B cells, T cells, mast cells, epithelial cells, stem cells, neuronal cells, or tumor cells, or combinations thereof. In other embodiments, the exosomes can be derived from immature dendritic cells or induced pluripotent stem cells (iPS cells). In other embodiments, the exosomes are derived from neuronal cells. Alternatively, in some embodiments, the exosomes are synthetic exosomes.

In some embodiments, the exosomes can contain a targeting peptide, for example, a targeting peptide that directs the exosomes to neuronal cells.

In some embodiments, the oligonucleotide targets a gene associated with a neurological disease or disorder. In certain embodiments, the oligonucleotide directs the silencing of a mutant huntingtin gene or a mutant SOD1 gene. For example, in some embodiments, the oligonucleotide is an siRNA targeting a mutant huntingtin gene or a mutant SOD1 gene.

In some embodiments, the foregoing compositions can be produced by incubating an oligonucleotide comprising one or more hydrophobic modifications with a population of exosomes.

In another aspect, the invention provides a pharmaceutical composition for delivery of a therapeutic oligonucleotide to a subject, comprising exosomes loaded with a therapeutically effective amount of an oligonucleotide containing one or more hydrophobic modifications, and a pharmaceutically acceptable carrier or excipient.

In another aspect, the invention provides a pharmaceutical composition that comprises exosomes loaded with a therapeutically effective amount of an oligonucleotide comprising one or more hydrophobic modifications, and a pharmaceutically acceptable carrier or excipient.

In one embodiment, the pharmaceutical compositions contain at least about $10^7$ exosomes, e.g., at least about $10^8$ exosomes, $10^9$ exosomes, $10^{10}$ exosomes, $10^{11}$ exosomes, $10^{12}$ exosomes, $10^{13}$ exosomes, $10^{14}$ exosomes, $10^{15}$ exosomes, $10^{16}$ exosomes, $10^{17}$ exosomes, $10^{18}$ exosomes, or $10^{19}$ exosomes. In an exemplary embodiments, the pharmaceutical compositions contain about $10^8$-$10^{15}$ exosomes.

In some embodiments, at least about 90% of the exosomes in the composition are loaded with hydrophobically modified oligonucleotide. In other embodiments, at least about 99% of the exosomes in the composition are loaded with hydrophobically modified oligonucleotide. The exosomes in the pharmaceutical compositions can be loaded with the hydrophobically modified oligonucleotide at concentrations described herein. For example, the exosomes may contain an average of about 500-1000 oligonucleotide molecules per exosome. In other embodiments, the exosomes may contain an average of about 1000-3000 oligonucleotide molecules per exosome.

In another embodiment, the invention provides a pharmaceutical composition containing a plurality of exosomes loaded with a hydrophobically modified oligonucleotide, as set forth in any embodiments described herein, and a pharmaceutically acceptable carrier or excipient.

In another aspect, the invention provides a method of delivering an exogenous oligonucleotide to a subject, by administering to the subject a composition comprising exosomes, wherein the exosomes are loaded with an exogenous oligonucleotide containing one or more hydrophobic modifications.

In another aspect, the invention provides a method of silencing gene expression in a cell, by contacting the cell with a composition comprising exosomes, wherein the exosomes are loaded with an oligonucleotide that directs the silencing of a target gene in the cell, and wherein the oligonucleotide contains one or more hydrophobic modifications. In certain embodiments, the target gene is associated with a neuronal disease or disorder. In exemplary embodiments, the target gene is a mutant huntingtin gene or a mutant SOD1 gene.

In another aspect, the invention provides a method of silencing gene expression in a subject, by administering to the subject a composition comprising exosomes, wherein the exosomes are loaded with an oligonucleotide that directs the silencing of a target gene in the subject, and wherein the oligonucleotide contains one or more hydrophobic modifications. In certain embodiments, the target gene is associated with a neuronal disease or disorder. In exemplary embodiments, the target gene is a mutant huntingtin gene or a mutant SOD1 gene.

In another aspect, the invention provides a method of treating a disease or disorder in a subject, by administering to the subject a composition containing exosomes loaded with hydrophobically modified oligonucleotide cargo, wherein the hydrophobically modified oligonucleotide cargo reduces or inhibits expression of a gene associated with a disease or disorder. In some embodiments, the disorder is a neurological disorder. In some embodiments, the disorder is Huntington's disease, and the oligonucleotide cargo reduces or inhibits expression of a mutant huntingtin gene. In other embodiments, the disorder is ALS, and the oligonucleotide cargo reduces or inhibits expression of a mutant SOD1 gene.

The foregoing methods can employ exosomes loaded with hydrophobically modified oligonucleotides as described herein.

For example, in one embodiment of the foregoing aspects, at least 90% of exosomes in the composition are loaded with the oligonucleotide. In other embodiments, at least 99% of the exosomes are loaded with the oligonucleotide. In one embodiment, the exosomes are loaded with the oligonucleotide at an average concentration of about 500-1000 oligonucleotide molecules per exosome. In another embodiment, the exosomes are loaded with the oligonucleotide at an average concentration of about 1000-3000 oligonucleotide molecules per exosome.

In preferred embodiments of the foregoing aspects, the oligonucleotide is a synthetic oligonucleotide. In some embodiments, the oligonucleotide is a siRNA, siRNA-GalNAc, antisense RNA, LNA, hairpin siRNA, PMO, miRNA, miRNA inhibitor, or a combination thereof. In an exemplary embodiment, the oligonucleotide is siRNA. In another embodiment, the oligonucleotide is miRNA.

In certain embodiments of the foregoing aspects, the hydrophobic modification increases the hydrophobicity of the oligonucleotide by at least about 2 orders of magnitude relative to unmodified oligonucleotide. In some embodiments, at least 30% of the nucleotides in the oligonucleotide contain a hydrophobic modification. In other embodiments, at least 50% of the nucleotides in the oligonucleotide contain a hydrophobic modification.

In certain embodiments, the hydrophobic modification is a backbone modification, a sugar modification (e.g., a ribose modification), a base modification, or a combination thereof. Backbone modifications can include, in some embodiments, phosphorothioate modifications, phosphorodithioate modifications, p-ethoxy modifications, methylphosphonate modifications, methylphosphorothioate modifications, alkyl- and aryl-phosphate modifications, alkylphosphotriester modifications, peptide nucleic acid (PNA) modifications, and/or locked nucleic acid (LNA) modifications. Ribose modifications can include, in some embodiments, 2'O-Methyl, 2'Methoxy-ethyl, 2'Fluor, or 2'FANA. Base modifications can include, in some embodiments, phenyl, naphthyl, or isobutyl.

In certain embodiments, the oligonucleotide can be conjugated to one or more hydrophobic moieties. For example, in some embodiments the hydrophobic moiety can be a sterol, GM1, a lipid, a vitamin, a small molecule, or a peptide, or a combination thereof. In an exemplary embodiment, the oligonucleotide cargo is conjugated to a sterol, e.g., cholesterol. In another exemplary embodiment, the oligonucleotide cargo is conjugated to GM1. In another exemplary embodiment, the oligonucleotide cargo is conjugated to myristic acid, or a derivative thereof. In one embodiment, the oligonucleotide cargo is an siRNA that is modified as depicted in FIG. 10.

In certain embodiments, the exosomes can be derived from cultured cells. In exemplary embodiments, the exosomes can be derived from dendritic cells (DC), B cells, T cells, mast cells, epithelial cells, stem cells, neuronal cells, or tumor cells, or combinations thereof. In other embodiments, the exosomes can be derived from immature dendritic cells or induced pluripotent stem cells (iPS cells). In other embodiments, the exosomes are derived from neuronal cells. Alternatively, in some embodiments, the exosomes are synthetic exosomes.

In some embodiments, the exosomes can contain a targeting peptide, for example, a targeting peptide that directs the exosomes to neuronal cells.

In another embodiment of the foregoing aspects, the exosomes loaded with hydrophobically modified oligonucleotide cargo are produced by a method comprising incubating the hydrophobically modified oligonucleotide with a population of exosomes.

In various embodiments of any of the foregoing aspects, the hydrophobically modified oligonucleotide can contain a detectable label. Exemplary labels include fluorescent labels and/or radioactive labels. In one embodiment, the detectable label is Cy3.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 12A-C. Characterization of unloaded and hsiRNA-loaded exosomes. Exosomes were loaded with hsiRNAs and purified by ultracentrifugation. Loaded and unloaded exosomes were characterized for (A) charge (Zetasizer, Malvern), (B) integrity (electron microscopy) and (C) size distribution (Nanosight, Malvern). No major changes with exception of a slight decrease in zeta potential are noted.

FIG. 19A-F. Exosomes and hsiRNA-loaded exosomes have no impact on immune response in vivo. (A to C) PBS, exosomes or HTT10150-loaded exosomes were unilaterally injected into the striatum of WT (FVBj) mice. Mice were perfused after 6 hours and brains were sliced into 40 µm sections. (A and B) Sections were stained with Iba1 antibody to evaluate microglial response. White arrowhead=resting microglia; Black arrowhead=Activated microglia. (C) Quantification of resting and activated microglia cells was performed manually and showed a slight increase in activated microglia in all samples in the ipsilateral side of the brain. (D to F) PBS, exosomes or HTT10150-loaded exosomes were unilaterally infused into the striatum of WT (FVBj) mice. Mice were perfused after 7 days and brains were sliced into 40 µm sections. (D and E) Sections were stained with Iba1 antibody to evaluate microglial response. White arrowhead=resting microglia; Black arrowhead=Actived microglia. (F) Quantification of resting and activated microglia cells was performed manually and showed an increase in activated microglia in all samples in the ipsilateral side of the brain.

DETAILED DESCRIPTION OF THE INVENTION

Figure 1A:
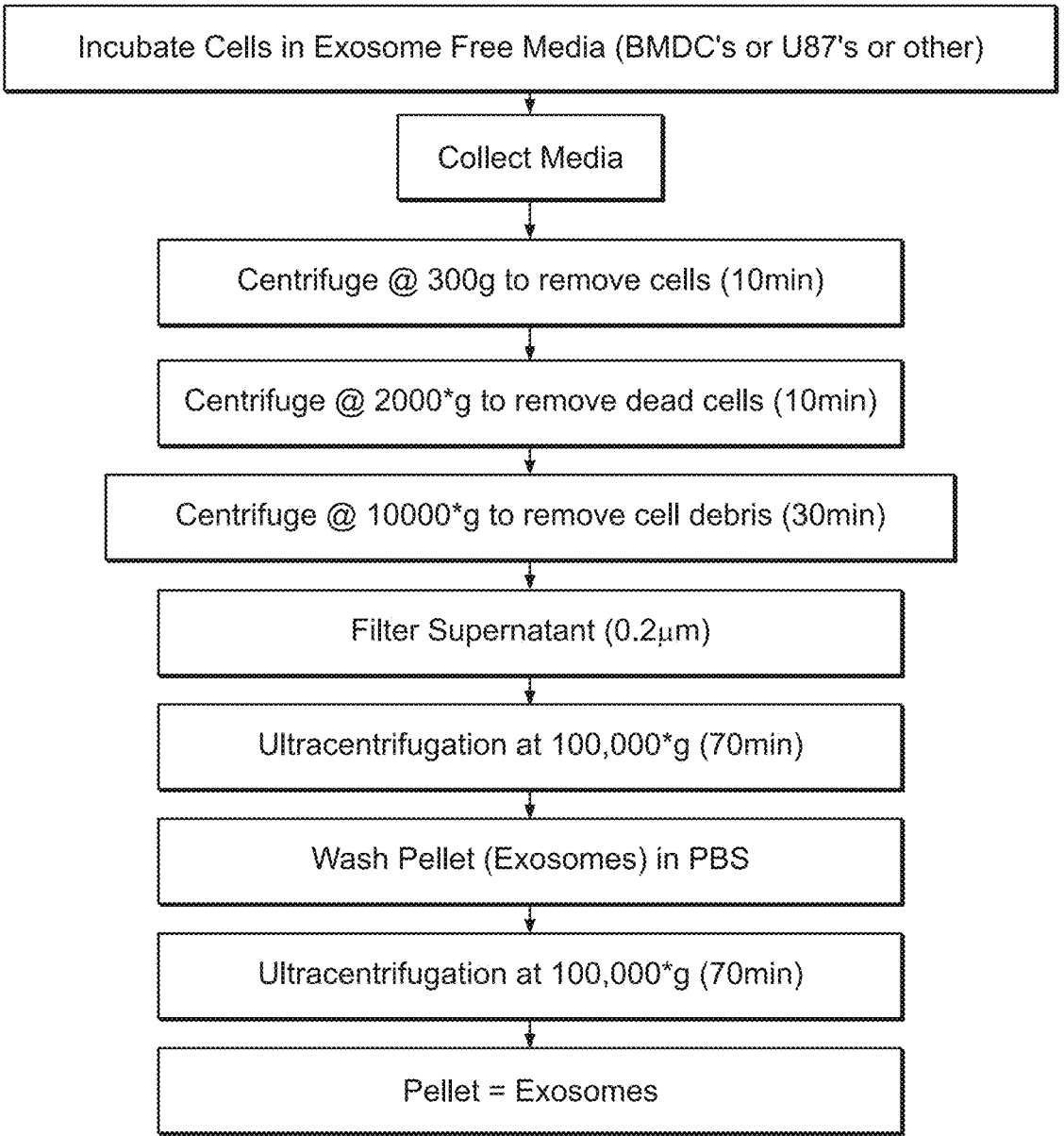
FIGS. 1A and B. Purification and QC of exosomes produced from U87 conditioned media. A. Overview of differential centrifugation protocol. B. Particle size and concentration evaluation by Nanoparticle tracking analyzer (Nanosight) C. Electron microscopy of exosome sample confirming size and integrity.

One limitation to the wide-spread adoption of oligonucleotide-based therapies is the highly inefficient transit of oligonucleotides from outside cells to the intracellular compartments where functional activity of the oligonucleotides takes place. Exploiting natural, evolutionarily conserved, mechanisms and pathways for trafficking of small RNAs across cellular boundaries may fundamentally improve the efficiency of oligonucleotide-based therapy. It has been previously demonstrated that exosomes might efficiently transfer therapeutic oligonucleotides to cells and tissues. However, one of the main technical unresolved issues is the loading of exosomes with oligonucleotides.

Current methods of loading exosomes with nucleic acid cargo include electroporation, or transfection with cationic lipid reagents. Other methods include loading by ultracentrifugation. Each of these methods results in very low loading efficiency, where only a small fraction of added oligonucleotide molecules are transferred to exosomes. For example, one laboratory reported a loading efficiency using ultracentrifugation of 1 molecule of siRNA per 1000 exosomes.

New methods of loading exosomes with nucleic acid cargo are described herein. These methods are based, at least in part, on the discovery that introduction of a hydrophobic modification into an oligonucleotide facilitates exosomal loading. Accordingly, in some embodiments, the present invention relates to improved methods of loading exosomes with nucleic acid cargo. In other embodiments, the invention relates to exosomes loaded with nucleic acid cargo, in which the nucleic acid molecules contain one or more hydrophobic modifications. In other embodiments, the invention relates to the use of exosomes loaded with hydrophobically-modified nucleic acid cargo as delivery vehicles, e.g., for delivery of small oligonucleotides to cells or tissues.

I. Definitions

Prior to setting forth the invention in detail, definitions of certain terms to be used herein are provided. Unless defined otherwise, all technical and scientific terms used herein have the same meaning as is commonly understood by one of skill in the art.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising, "having," "including," and "containing" are to be construed as open-ended terms (i.e., meaning "including, but not limited to") unless otherwise noted. Recitation of ranges of values herein are merely intended to serve as a shorthand method of referring individually to each separate value recited or falling within the range, unless otherwise indicated herein, and each separate value is incorporated into the specification as if it were individually recited.

The term "nucleotide" as used herein refers to a modified or naturally occurring deoxyribonucleotide or ribonucleotide capable of Watson-Crick base pairing with a complementary nucleotide. Nucleotides can include nucleotide analogs (e.g., morpholinos, PMOs, etc.) capable of Watson-Crick base pairing. Nucleotides typically include purines and pyrimidines, which include thymidine, cytidine, guanosine, adenine and uridine.

The term "oligonucleotide" or "nucleic acid molecule" as used herein refers to an oligomer of the nucleotides defined above.

The term "hydrophobic modification" as used herein refers to a modification that increases the hydrophobicity of an oligonucleotide, as compared to native (non-modified) RNA or DNA.

The term "including" is used herein to mean, and is used interchangeably with, the phrase "including but not limited to".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of an embodiment for a variable or aspect herein includes that embodiment as any single embodiment or in combination with any other embodiments or portions thereof.

As will be evident to one of ordinary skill, any compositions or methods provided herein can be combined with one or more of any of the other compositions and methods provided herein.

II. Exosomes

Exosomes are small vesicles that originate in eukaryotic cells, primarily from the endosomal pathway. Exosomes are bound by a plasma membrane and are released from cells into the extracellular environment. Generally, these vesicles are approximately 30-100 nM in diameter, but can range in size from approximately 20 nM to approximately 200 nM. Naturally occurring exosomes are hypothesized to transport molecules from one cell to another. Exosomes are taken up by recipient cells by endocytosis or by fusion of the exosomal membrane with the plasma membrane of the recipient cell.

These and other properties of exosomes have led to their use as delivery vehicles for synthetic cargo, e.g., proteins and nucleic acids. Exosomes are an attractive alternative to liposomes for use as delivery vehicles, because they readily cross major biological membranes due to their small size and the nature of their lipid bi-layer. They are well-tolerated by subjects, and are highly stable in biological fluids, which protects exosomal cargo from degradation.

Exosomes can be isolated and/or purified from the media of cells grown in culture (i.e., conditioned media), or from biological fluids obtained from a subject, e.g., plasma, blood, urine, lymph, etc. A majority of cell types produce exosomes, including, but not limited to, dendritic cells (DC), B cells, T cells, mast cells, epithelial cells, stem cells, neuronal cells, and tumor cells. Accordingly, exosomes used in the methods and compositions described herein can be derived from any of these cell types, or combinations thereof. By way of example, exosomes can be derived from immune cells, B lymphocytes, T lymphocytes, dendritic cells, immature dendritic cells, mast cells, neuronal cells, stem cells and/or tumor cells. In some embodiments, exosomes are derived from immature dendritic cells that do not express MHC-I, MHC-II, or CD86, and consequently minimize clearance by the immune system of a subject following administration. In an exemplary embodiment, exosomes are derived from neuronal cells. In another exemplary embodiment, exosomes are derived from stem cells, for example, adult pluripotent stem cells. In certain embodiments, exosomes are derived from induced pluripotent stem cells (iPS cells). In another exemplary embodiment, exosomes are derived from U87 cells.

Exosomes can be isolated from cells grown in culture or from biological fluids by any suitable method known in the art. For example, exosomes can be isolated using techniques including differential centrifugation, precipitation, gel-filtration, column binding, affinity purification, or combinations of these methods. By way of non-limiting example, exosomes can be purified by isolation from cells and other cellular components by differential centrifugation, whereby cell culture supernatants are centrifuged at low speeds (e.g., 20,000 g or less) to remove cells and cellular debris, followed by centrifugation at high speeds (e.g., 100,000 g or more) to pellet exosomes. This procedure can be used in conjunction with filtration (e.g., using filters of approximately 0.8 µM and/or 0.2 µM) to eliminate cell debris and other contaminants. In another example, exosomes can be purified using a density gradient, e.g., a sucrose density gradient, to isolate exosomes having an average density of approximately 1.13-2.21 g/mL. In an exemplary embodiment, exosomes can be purified by centrifugation at approximately 300 g to remove cells, followed by centrifugation at approximately 2000 g to remove dead cells, followed by centrifugation at approximately 10,000 g to remove cellular debris. The supernatant can be filtered using a filter of, for example, approximately 0.2 μm. The filtrate can then be centrifuged at 100,000 g to pellet exosomes. If desired, the pellet can be washed, and centrifuged again at 100,000 g to further purify the exosome population. Exemplary protocols for isolating exosomes are described in FIG. 1A and FIG. 9A.

Other methods of exosomal isolation are described by Raposo et al. (1996), B lymphocytes secrete antigen-presenting vesicles, *J. Exp. Med.* 183:1161-1172. One exemplary method of purifying exosomes from a large volume of conditioned medium by ultrafiltration is described by Lamparski et al. (2002), Production and characterization of clinical grade exosomes derived from dendritic cells, J. Immunol. Methods 270:211-226. This method is particularly for isolation of exosomes for therapeutic administration to a subject. Other exemplary methods of exosome purification are described by Thery et al., Isolation and Characterization of Exosomes from Cell Culture Supernatants and Biological Fluids, Current Protocols in Cell Biology (2006) 3.22.1-3.22.29.

A number of kits are commercially available to facilitate purification of exosomes from a variety of source material. These include, for example, the Exo-spin™ Exosome Purification Kit from Cell Guidance Systems, the Total Exosome Isolation Kit from Life Technologies, the ExoQuick™ Exosome Isolation Kit from System Biosciences, and the Exo-Flow™ exosome immunopurification kit from System Biosciences.

In some embodiments, exosomes are synthetically produced. In such embodiments, artificial exosomes can be created by embedding exosomal proteins in a lipid bilayer. For example, liposomes can be assembled which contain a variety of components found in native exosomes. Such synthetic exosomes are sometimes termed exosome mimetics. Synthetic exosomes are described in, for example, Kooijmans et al., Int. J. Nanomedicine (2012), 7:1525-1541, and in De La Pena et al., J. Immunol. Methods (2009), 344 (2): 121-32.

III. Loading Exosomes with Hydrophobically Modified Nucleic Acid Cargo

In certain embodiments, the invention relates to a highly efficient method of loading exosomes with nucleic acid cargo. Currently, a predominant obstacle to the commercialization of exosomes as a delivery vehicle for oligonucleotides is highly inefficient loading. This obstacle can be overcome by hydrophobically modifying nucleic acid cargo prior to loading the cargo into exosomes. As described herein, hydrophobic modification of nucleic acid cargo facilitates loading of nucleic acid into exosomes. Without wishing to be bound by theory, it is proposed that hydrophobic modification of nucleic acid cargo allows self-assembly of the cargo into exosomal vesicles. Surprisingly, hydrophobic modification of nucleic acid cargo permits exosomal loading in the absence of electroporation, and without the use of transfection reagents, e.g., cationic liposome transfection reagents. Hydrophobic modification of nucleic acid cargo also permits exosomal loading without the need for ultracentrifugation (however, in some embodiments, ultracentrifugation may nonetheless be useful for purification of exosomes prior to or after loading). Hydrophobically modified nucleic acid cargo can be loaded into exosomes with significantly improved efficiency relative to that which is generally reported for methods of loading exosomes by traditional methods, for example, electroporation, lipid-mediated transfection, or ultracentrifugation.

Accordingly, in some embodiments, the invention features a method of loading exosomes with oligonucleotide cargo, by incubating a hydrophobically modified oligonucleotide with a population of exosomes for a period of time sufficient to permit loading of the exosomes with the hydrophobically modified oligonucleotide.

In other embodiments, the invention features a method of loading exosomes with oligonucleotide cargo, consisting of or consisting essentially of incubating a hydrophobically modified oligonucleotide with a population of exosomes for a period of time sufficient to permit loading of the exosomes with the hydrophobically modified oligonucleotide.

In other embodiments, the invention features a method of loading exosomes with oligonucleotide cargo, by introducing one or more hydrophobic modifications into the oligonucleotide cargo, and incubating the hydrophobically modified oligonucleotide with a population of exosomes for a period of time sufficient to permit loading of the exosomes with the hydrophobically modified oligonucleotide.

In a preferred aspect of each of the foregoing embodiments, exosomes are loaded without the use of electroporation, and in the absence of transfection reagents. For example, exosomes can be efficiently loaded with hydrophobically modified oligonucleotide in the absence of lipid-based transfection reagents, such as cationic liposome transfection reagents. Exosomes can also be loaded without the use of ultracentrifugation (however, in some embodiments, ultracentrifugation may nonetheless be useful for purification of exosomes prior to or after loading).

The duration of time sufficient to permit loading of the exosomes with hydrophobically modified oligonucleotide cargo can be optimized for the particular type of cargo and the type of modification. Generally, an incubation of 1 hour or less is sufficient to permit efficient loading of exosomes with hydrophobically modified cargo. In many instances, hydrophobically modified cargo is efficiently loaded into exosomes in a very rapid period of time, for example, within 5 minutes. Accordingly, in some embodiments, efficient loading takes place during an incubation period of 5 minutes or less, e.g., from 1-5 minutes. In exemplary embodiments, efficient loading takes place during an incubation period of 5 minutes, 10 minutes, 15 minutes, 20 minutes, 30 minutes, etc. In other embodiments, efficient loading may take place within 1 hour, within 2 hours, within 3 hours, within 4 hours, within 5 hours, within 6 hours, within 7 hours, within 8 hours, within 9 hours, within 10 hours, within 12 hours, within 24 hours, etc.

Loading of exosomes with hydrophobically modified oligonucleotides is not highly temperature dependent. In exemplary embodiments, exosomes are loaded at or around 37° C. In other embodiments, exosomes can be loaded at or around room temperature. In other embodiments, exosomes can be loaded at or around 4° C.

The methods of loading exosomes with oligonucleotide cargo (i.e. hydrophobically modified oligonucleotide cargo) set forth herein significantly improve loading efficiency as compared to the loading efficiency previously reported for introducing unmodified nucleic acid cargo into exosomes by, for example, electroporation or cationic lipid transfection. In some embodiments, over 50% of hydrophobically modified oligonucleotide cargo is incorporated into exosomes using the methods described herein. Accordingly, in some embodiments, hydrophobically modified oligonucleotide cargo is incorporated into exosomes with an efficiency of 5-40%. For example, hydrophobically modified oligonucleotide cargo is incorporated into exosomes with an efficiency of 5% or greater, 10% or greater, 15% or greater, 20% or greater, 25% or greater, 30% or greater, 35% or greater, 40% or greater, or 50% or greater. The methods described herein result in the incorporation of hydrophobically modified oligonucleotide into all or nearly all of the exosomes that are treated. For example, at least 80% of the exosomes incubated with hydrophobically modified oligonucleotide are typically loaded with the oligonucleotide. In some embodiments, hydrophobically modified oligonucleotide cargo is incorporated in at least 90% of the exosomes incubated with the oligonucleotide. Thus, populations of exosomes in which at least 80%, at least 90%, at least 91%, at least 92%, at least 93%, at least 94%, at least 95%, at least 96%, at least 97%, at least 98% or more of the exosomes are loaded with the oligonucleotide cargo can be readily obtained. In one embodiment at least 99% of the exosomes are loaded with the hydrophobically modified oligonucleotide.

The methods described herein also allow greater quantities of cargo oligonucleotides to be loaded into exosomes than could be achieved using traditional methods. For example, exosomes can be loaded with over 500 hydrophobically modified oligonucleotide molecules per exosome, e.g., at least 500, at least 600, at least 700, at least 800, at least 900, at least 1000, at least 1200, at least 1500, at least 2000, at least 2500, at least 3000 or more hydrophobically modified oligonucleotides per exosome. In one embodiment, the exosomes contain an average of about 500-3000 hydrophobically modified oligonucleotides per exosome. In another embodiment, exosomes contain an average of about 500-1000 hydrophobically modified oligonucleotides per exosome. In another embodiment, exosomes contain an average of about 1000-1500 hydrophobically modified oligonucleotides per exosome. In another embodiment, exosomes contain an average of about 1000-2000 hydrophobically modified oligonucleotides per exosome. In another embodiment, exosomes contain an average of about 1000-3000 hydrophobically modified oligonucleotides per exosome. In another embodiment, exosomes contain up to about 3000 hydrophobically modified oligonucleotides per exosome. The quantities of hydrophobically modified oligonucleotide cargo that can be loaded into exosomes allow the production of exosomes in which the hydrophobically modified oligonucleotide cargo occupies a significant proportion of the exosomal membrane. For example, exosomes can be produced in which hydrophobically modified oligonucleotide cargo occupies about 1-10% of the surface area of the exosome, e.g., about 1%, 2%, 3%, 4%, 5%, 6%, 7%, 8%, 9%, or 10% of the surface area of the exosome.

In another embodiment, hydrophobically modified nucleic acid molecules can be incorporated into exosomes during exosome production by cells in culture. In accordance with this embodiment, hydrophobically modified nucleic acid molecules can be incubated with cells in culture, resulting in efficient uptake of hydrophobic nucleic acid by cells. Cells are then incubated for a period of time sufficient for exosome production. Exosomes isolated from the culture media will contain exosomes loaded with the hydrophobic nucleic acid molecule taken up by the cells.

Accordingly, in one embodiment, a method of loading exosomes with oligonucleotide cargo is provided, comprising incubating cells capable of exosome production with an oligonucleotide containing one or more hydrophobic modifications for a period of time sufficient for the oligonucleotide to be internalized by the cells, culturing the cells for a period of time sufficient for exosome secretion, and isolating exosomes loaded with the oligonucleotide from the culture medium.

IV. Hydrophobically Modified Nucleic Acid Molecules

Oligonucleotide molecules which are amenable to hydrophobic modification can be loaded into exosomes as described herein. In some embodiments, the oligonucleotide cargo is DNA. In other embodiments, the oligonucleotide cargo is RNA. In other embodiments, the oligonucleotides are nucleotide analogs. Non-limiting examples of oligonucleotide molecules which can be loaded into exosomes as described herein include siRNA, siRNA-GalNAc, antisense, Locked Nucleic Acids (LNAs), hairpin siRNA, phosphorodiamidate morpholino oligomers (PMOs), miRNA, and oligonucleotide miRNA inhibitors. In some embodiments, the oligonucleotide molecules are plasmid DNA, which can be modified with a hydrophobic modification post-transcriptionally. In an exemplary embodiment, the oligonucleotide cargo is a siRNA. In another exemplary embodiment, the oligonucleotide cargo is a hairpin siRNA. In another exemplary embodiment, the oligonucleotide cargo is a miRNA.

In certain embodiments, the oligonucleotide cargo is capable of modifying gene expression in a target cell. For example, the oligonucleotide cargo may reduce or inhibit expression of one or more genes in a target cell. This can occur by way of direct targeting of DNA or RNA through Watson-Crick base pairing. By way of example, cargo molecules capable of reducing or inhibiting expression of one or more genes in a target cell can include siRNA, siRNA-GalNAc, antisense, Locked Nucleic Acids (LNAs), hairpin siRNA, phosphorodiamidate morpholino oligomers (PMOs), miRNA, and oligonucleotide miRNA inhibitors. In other embodiments, the oligonucleotide cargo may increase expression of one or more genes in a target cell.

By way of example, cargo molecules capable of increasing expression of one or more genes in a target cell include expression vectors and oligonucleotide miRNA inhibitors.

In some embodiments, the oligonucleotide cargo is a therapeutic oligonucleotide. A therapeutic oligonucleotide is useful in treating or ameliorating the signs and symptoms of a disease or disorder when administered to a subject. For example, a therapeutic oligonucleotide can target a gene involved in a disease process, thereby reducing the symptoms of the disease in a subject to whom the therapeutic oligonucleotide is administered.

In order to facilitate exosomal loading, oligonucleotide cargo contains one or more hydrophobic modifications. Hydrophobic modifications increase the hydrophobicity of the oligonucleotide cargo, as compared to native (non-modified) RNA or DNA. In certain embodiments, the hydrophobic modifications increase the hydrophobicity of the oligonucleotide by at least two orders of magnitude (e.g., at least 3, 4, 5, 6, 7, 8, 9, 10 or more orders of magnitude) relative to native (non-modified) RNA or DNA. In other embodiments, the hydrophobic modifications increase the hydrophobicity of the oligonucleotide by at least 10 orders of magnitude relative to native (non-modified) RNA or DNA. In other embodiments, the hydrophobic modifications increase the hydrophobicity of the oligonucleotide by at least two orders of magnitude (e.g., at least 3, 4, 5, 6, 7, 8, 9, 10 or more orders of magnitude) relative to the unmodified oligonucleotide. In other embodiments, the hydrophobic modifications increase the hydrophobicity of the oligonucleotide by at least ten orders of magnitude relative to the unmodified oligonucleotide. Increases in hydrophobicity can be assessed using any suitable method. For example, hydrophobicity can be determined by measuring the percentage solubility in an organic solvent, such as octanol, as compared to solubility in an aqueous solvent, such as water.

In some embodiments, the hydrophobic character of oligonucleotide cargo can be increased by increasing the proportion of nucleotides within the oligonucleotide molecule that are hydrophobically modified. For example, in one embodiment, 20% or more of the nucleotides in an oligonucleotide molecule are hydrophobically modified, e.g., 25% or more, 30% or more, 40% or more, 50% or more, 60% or more, 70% or more, 80% or more, 90% or more, 95% or more, 99% or more, etc. of the nucleotides in an oligonucleotide molecule are hydrophobically modified. In one embodiment, 100% of the nucleotides in an oligonucleotide molecule are hydrophobically modified. In an exemplary embodiment, 30% or more of the nucleotides in an oligonucleotide molecule contain hydrophobic modifications.

Increasing the proportion of hydrophobically modified nucleotides in an oligonucleotide molecule can be useful when, for example, the hydrophobic modification is weakly hydrophobic, for example, a 2'O-methyl modification. In embodiments where a strongly hydrophobic modification is employed, for example, a sterol, a lipid, etc., a single hydrophobic modification can be sufficient to facilitate exosomal loading.

Figure 3A:
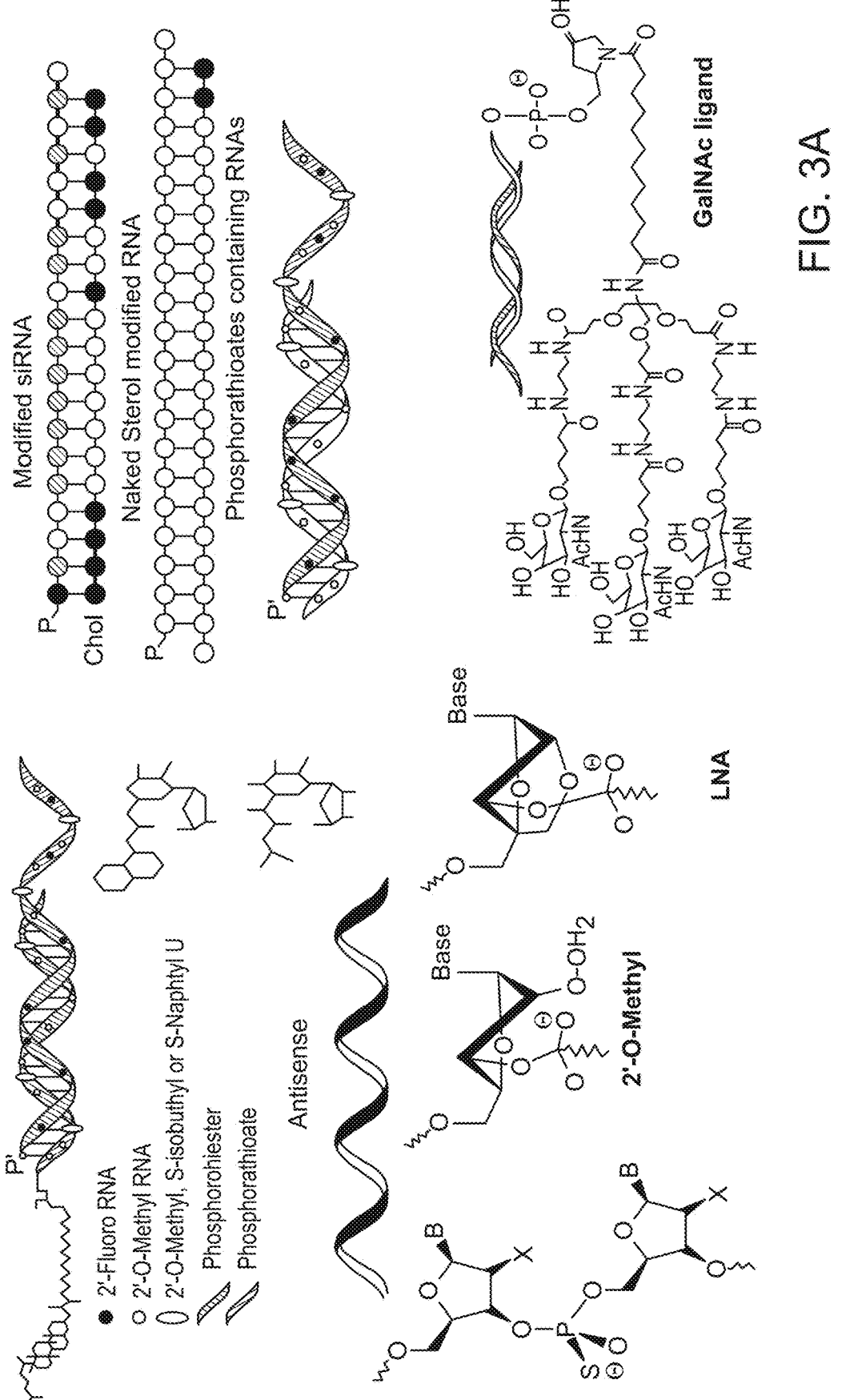
FIG. 3A-B. Examples of hydrophobically modified oligonucleotides. An example of hydrophobically modified asymmetric siRNAs, siRNA-sterol conjugates, siRNA-GalNac conjugates, 2'F, 2' O-methyl modified siRNAs, phosphorothioated ASOs, LNAs, methoxyethyl, phenol, isobutyl, and naphthyl modifications.
Figure 3B:
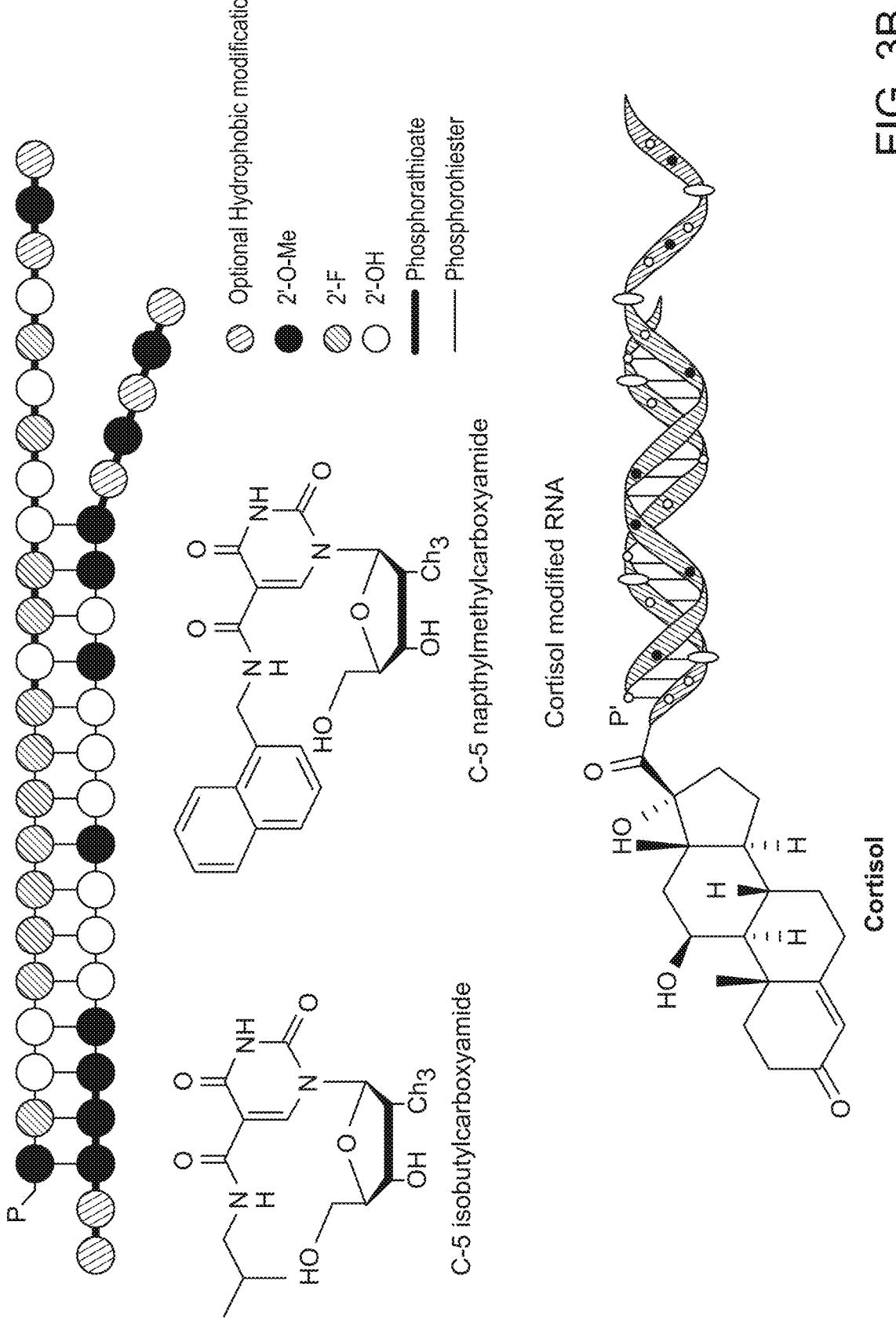

In preferred embodiments, the hydrophobic modification is a covalent modification. Exemplary hydrophobic modifications are depicted in FIG. 3 and FIG. 10, and in Table 2.

Hydrophobic modifications of nucleic acid molecules can include, for example, backbone modifications, sugar modifications, base modifications and/or conjugate modifications, and combinations thereof.

Backbone modifications involve alterations to the phosphate ester linkages in the nucleic acid molecule. Examples of suitable backbone modifications include, but are not limited to, phosphorothioate modifications, phosphorodithioate modifications, p-ethoxy modifications, methylphosphonate modifications, methylphosphorothioate modifications, alkyl- and aryl-phosphates (in which the charged phosphonate oxygen is replaced by an alkyl or aryl group), alkylphosphotriesters (in which the charged oxygen moiety is alkylated), peptide nucleic acid (PNA) backbone modifications, locked nucleic acid (LNA) backbone modifications, and the like. These modifications may be used in combination with each other and/or in combination with phosphodiester backbone linkages.

In one embodiment, the hydrophobic modification is a phosphorothioate (PS) modification, where one of the nonbridging phosphate oxygen atoms is replaced by sulfur to give a PS group (see, for example, Eckstein, *Biochimie.* 2002, 84, 841-848). This modification provides significant resistance to nuclease degradation and has favorable pharmacokinetic properties (Bumcrot et al, *Nat. Chem. Biol.* 2006, 2, 711-719). PS linkages can readily incorporated into oligonucleotide molecules using standard techniques, such as solid-phase oligonucleotide synthesis (Sanghvi, *Current Protocols in Nucleic Acid Chemistry,* 2011, 4.1.1-4.1.22).

In another embodiment, the hydrophobic modification is a phosphonate modification, in which one nonbridging oxygen is replaced with an alkyl group. In other embodiments, the hydrophobic modification is a peptide nucleic acid (PNA) modification. PNAs are oligonucleotide mimics that have a peptide backbone with a neutral charge, as compared with the highly charged sugar-phosphate backbone of native RNA and DNA (see, for example, Nielsen et al, *Science* 1991, 254, 1497-1500; Demidov et al, *Biochem Pharmacol,* 1994, 48, 1310-1313). In other embodiments, the hydrophobically modified nucleic acid molecule is a phosphorodiamidate morpholino oligonucleotide (PMO).

In other embodiments, oligonucleotide cargo molecules may be hydrophobically modified at the sugar moiety (e.g., ribose, deoxyribose, etc.). Sugar modifications often occur at the 2' position of the sugar ring, where, for example, the 2' moiety can be modified or substituted with a hydrophobic moiety, such as a halo, alkoxy, aminoalkoxy, alkyl, azido or amino group. In non-limiting examples, sugar modifications can include O-methyl, F, methoxy-ethyl, and 2'-fluoro-β-D-arabinonucleotide (FANA). Other 2' modifications include, for example, 2'O-allyl, 2'O-ethylamine, and 2'O-cyanoethyl modifications. In addition, modifications can be made at other sites including the 4' position of the sugar (see, for example, Deleavey, et al, *Chem Bio,* 2012, 19, 937-954).

In other embodiments, oligonucleotide cargo molecules may contain hydrophobic base modifications. In exemplary embodiments, these modifications include phenyl, naphthyl, and isobutyl. Other embodiments include C-5 propynyl modified bases, 5-methylcytosine, 2-aminopurine, 2-amino-6-chloropurine, 2,6-diaminopurine, and hypoxanthine.

In addition to increasing the hydrophobic character of the oligonucleotide cargo, the foregoing backbone, sugar, and base modifications increase the stability of the olignoucleotides in the presence of exosomes, and minimize any degradation that may occur during loading.

Hydrophobic moieties can also be chemically conjugated to oligonucleotide cargo to enhance its hydrophobic character. In exemplary embodiments, the moiety is a sterol (e.g., cholesterol), GM1, a lipid, a vitamin, a small molecule, a peptide, or a combination thereof. In some embodiments, the moiety is a lipid. For example, in certain embodiments, the moiety is palmitoyl. In some embodiments, the moiety is a sterol, e.g., cholesterol. Additional hydrophobic moieties include, for example, phospholipids, vitamin D, vitamin E, squalene, and fatty acids. In another exemplary embodiment, the oligonucleotide cargo is conjugated to myristic acid, or a derivative thereof (e.g., myristoylated oligonucleotide cargo). In some embodiments, the hydrophobic moiety is conjugated at the termini of the oligonucleotide cargo (i.e., "terminal modification"). In other embodiments, the hydrophobic moiety is conjugated to other portions of the oligonucleotide molecule.

In one embodiment, the oligonucleotide cargo is stabilized by incorporation of one or more backbone modifications, sugar modifications, and/or base modifications as described herein, and additionally is conjugated to a hydrophobic moiety. Exemplary embodiments are shown in FIG. 3 and FIG. 10. For example, the oligonucleotide cargo in certain embodiments can contain one or more backbone modifications, sugar modifications, and/or base modifications to at least 30%, at least 35%, at least 40%, at least 45%, at least 50%, at least 55%, at least 60%, at least 65% or more of the nucleotides, and further is conjugated to a hydrophobic moiety as described herein, e.g., conjugated to a sterol, GM1, a lipid, a vitamin, a small molecule, or a peptide, or a combination thereof. In an exemplary embodiment, the oligonucleotide cargo is conjugated to a sterol, e.g., choles-terol. In another exemplary embodiment, the oligonucle-otide cargo is conjugated to GM1. In another exemplary embodiment, the oligonucleotide cargo is conjugated to myristic acid, or a derivative thereof.

In one embodiment, the oligonucleotide cargo is an siRNA that contains a short duplex region (for example, 14-16 base pairs, e.g., 15 base pairs), and a single-stranded fully phosphorothioated tail. This embodiment is illustrated in FIG. 10. In this exemplary construct, pyrimidines are modified with 2'-fluoro and 2'-O-methyl modifications. The 3' end of the passenger strand of this exemplary construct is conjugated to cholesterol.

In some embodiments, the hydrophobically modified oli-gonucleotide can include a detectable label. Exemplary labels include fluorescent labels and/or radioactive labels. In embodiments where hydrophobically modified oligonucle-otides are fluorescently labeled, the detectable label can be, for example, Cy3. Adding a detectable label to hydropho-bically modified oligonucleotides can be used as a way of labeling exosomes, and following their biodistribution. In other embodiments, a detectable label can be attached to exosomes directly, for example, by way of labeling an exosomal lipid and/or an exosomal peptide.

Nucleic acids can be synthesized using any number of procedures known in the art. A number of automated nucleic acid synthesizers are commercially available for this pur-pose. In a preferred embodiment, the nucleic acid cargo is a synthetic oligonucleotide. In other embodiments, nucleic acids can be prepared using, for example, restriction enzymes, exonucleases, or endonucleases.

V. Compositions Containing Exosomes Loaded with Hydrophobically Modified Cargo In certain aspects, the invention provides exosomes loaded with hydrophobically modified oligonucleotide cargo. For example, in one aspect, the invention provides a composition comprising a population of exosomes loaded with an oligonucleotide comprising one or more hydropho-bic modifications. Exemplary exosome populations and hydrophobically modified oligonucleotides are set forth herein.

For example, the invention includes, in various embodi-ments, exosomes loaded with the hydrophobically modified oligonucleotides described herein. By way of example, the hydrophobically modified oligonucleotides can be synthetic oligonucleotides. In some embodiments, the hydrophobi-cally modified oligonucleotides are siRNA, siRNA-Gal-NAc, antisense RNA, LNA, hairpin siRNA, PMO, miRNA, miRNA inhibitors, or combinations thereof. In exemplary embodiments, the hydrophobically modified oligonucle-otides are siRNA or miRNA.

In some embodiments, the hydrophobic modifications increase the hydrophobicity of the oligonucleotide by at least two orders of magnitude, e.g., 2-10 orders of magni-tude, as described above. In some embodiments, the hydro-phobic character and/or the stability of the oligonucleotide cargo can be increased by increasing the proportion of nucleotides within the oligonucleotide molecule that are hydrophobically modified, as described above. Exemplary hydrophobic modifications include, e.g., backbone modifi-cations, ribose modifications, base modifications, and com-binations thereof, as described herein. For example, in embodiments the oligonucleotide cargo contains one or more backbone modifications, sugar modifications, and/or base modifications to at least 30%, at least 35%, at least 40%, at least 45%, at least 50%, at least 55%, at least 60%, at least 65% or more of the nucleotides In some embodi-ments, the oligonucleotide is conjugated to a hydrophobic moiety, e.g., sterol, GM1, a lipid, a vitamin, a small mol-ecule, or a peptide, or combinations thereof. Other examples of hydrophobic moieties are described herein, and include but are not limited to cholesterol, GM1, and myristic acid, or a derivative thereof.

In some embodiments, at least 80% of the exosomes in the compositions of the invention are loaded with the hydro-phobically modified oligonucleotide. In a preferred embodi-ment, at least 90% of the exosomes are loaded with the hydrophobically modified oligonucleotide. In exemplary embodiments, at least 91%, at least 92%, at least 93%, at least 94%, at least 95%, at least 96%, at least 97%, at least 98% or more of the exosomes are loaded with the hydro-phobically modified oligonucleotide. In one embodiment at least 99% of the exosomes are loaded with the hydropho-bically modified oligonucleotide.

In other embodiments, the compositions of the invention contain exosomes that are loaded with an average of at least 500 hydrophobically modified oligonucleotides per exo-some, e.g., at least 600, at least 700, at least 800, at least 900, at least 1000, at least 1200, at least 1500, at least 2000, at least 2500, at least 3000 or more hydrophobically modified oligonucleotides per exosome. In one embodiment, the exosomes contain an average of about 500-3000 hydropho-bically modified oligonucleotides per exosome. In another embodiment, exosomes contain an average of about 500-1000 hydrophobically modified oligonucleotides per exo-some. In another embodiment, exosomes contain an average of about 1000-1500 hydrophobically modified oligonucle-otides per exosome. In another embodiment, exosomes contain an average of about 1000-3000 hydrophobically modified oligonucleotides per exosome. In another embodi-ment, exosomes contain up to about 3000 hydrophobically modified oligonucleotides per exosome.

In another embodiment, the compositions of the invention include a plurality of exosomes in which hydrophobically modified oligonucleotide cargo occupies about 1-10% of the exosome surface, e.g., about 1%, 2%, 3%, 4%, 5%, 6%, 7%, 8%, 9%, or 10% of the surface area of the exosome.

Exosomes suitable for use in the compositions of the invention include exosomes having the characteristics described herein. For example, in one embodiment, the exosomes are derived from cultured cells, including but not limited to dendritic cells (DC), B cells, T cells, mast cells, epithelial cells, stem cells, neuronal cells, and tumor cells. In some embodiments, the cultured cells are immature den-dritic cells, neuronal cells, or stem cells, e.g., iPS cells. In other embodiments, the exosomes are synthetic exosomes. Optionally, the exosomes can include a targeting peptide, which can facilitate targeting of the exosomes to a particular cell type, for example, neuronal cells.

In some embodiments, the exosome compositions are pharmaceutical compositions. Accordingly, in one aspect, the invention provides pharmaceutical compositions con-taining exosomes loaded with hydrophobically modified oligonucleotides, as described herein, and a pharmaceuti-cally acceptable carrier or excipient. Such compositions can include exosomes loaded with a therapeutically effective amount of an oligonucleotide comprising one or more hydrophobic modifications, and a pharmaceutically accept-able carrier or excipient. Such pharmaceutical compositions are suitable for administration to a subject, e.g. a human subject or an animal subject. Pharmaceutical compositions containing exosomes loaded with hydrophobically modified oligonucleotides are described in additional detail below.

The simplicity and scalability of the exosomal loading methods described herein allow oligonucleotide-loaded exosomes to be readily generated in sufficient quantities for administration to a subject. In one embodiment, the pharmaceutical compositions contain at least about $10^7$ exosomes, e.g., at least about $10^8$ exosomes, about $10^9$ exosomes, about $10^{10}$ exosomes, about $10^{11}$ exosomes, about $10^{12}$ exosomes, about $10^{13}$ exosomes, about $10^{14}$ exosomes, about $10^{15}$ exosomes, about $10^{16}$ exosomes, about $10^{17}$ exosomes, about $10^{18}$ exosomes, or about $10^{19}$ exosomes. In an exemplary embodiments, the pharmaceutical compositions contain about $10^8$-$10^{15}$ exosomes. Additional dosage amounts of exosomes suitable for therapeutic administration are described below.

In some embodiments, at least about 90% of the exosomes in the composition are loaded with hydrophobically modified oligonucleotide. In other embodiments, at least about 99% of the exosomes in the composition are loaded with hydrophobically modified oligonucleotide. The exosomes in the pharmaceutical compositions can be loaded with the hydrophobically modified oligonucleotide at concentrations described herein. For example, the exosomes may contain an average of about 500-1000 oligonucleotide molecules per exosome. In other embodiments, the exosomes may contain an average of about 1000-3000 oligonucleotide molecules per exosome.

In another embodiment, the invention provides a pharmaceutical composition containing a plurality of exosomes loaded with a hydrophobically modified oligonucleotide, as set forth in any embodiments described herein, and a pharmaceutically acceptable carrier or excipient.

The composition may be formulated for parenteral, intramuscular, intracerebral, intravascular (including intravenous), subcutaneous, or transdermal administration. Pharmaceutical compositions may include sterile aqueous solutions which may also contain buffers, diluents and other suitable additives. The compositions may include pharmaceutically acceptable carriers, thickeners, diluents, buffers, preservatives, and other pharmaceutically acceptable carriers or excipients and the like in addition to the exosomes.

A "pharmaceutically acceptable carrier" (excipient) is a pharmaceutically acceptable solvent, suspending agent or any other pharmacologically inert vehicle for delivering exosomes to a subject. Typical pharmaceutically acceptable carriers include, but are not limited to, binding agents (e.g., pregelatinised maize starch, polyvinylpyrrolidone or hydroxypropyl methylcellulose, etc); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.).

The compositions provided herein may additionally contain other adjunct components conventionally found in pharmaceutical compositions. Thus, for example, the compositions may contain additional compatible pharmaceutically-active materials or may contain additional materials useful in physically formulating various dosage forms of the composition of present invention, such as dyes, flavouring agents, preservatives, antioxidants, opacifiers, thickening agents and stabilizers. However, such materials, when added, should not unduly interfere with the biological activities of the components of the compositions provided herein.

In certain embodiments, the exosome compositions of the invention are produced in accordance with the methods described herein. For example, exosome compositions containing exosomes loaded with hydrophobically modified oligonucleotides can be produced by incubating an oligonucleotide comprising one or more hydrophobic modifications with a population of exosomes.

VI. Exosome Delivery and Methods of Treatment

The exosomal compositions described herein can be used to deliver oligonucleotide cargo to cells. In one embodiment, the compositions described herein are used to deliver oligonucleotide cargo to cells in culture. In other embodiments, the compositions described herein are used to deliver oligonucleotide cargo to cells in a subject, i.e., a human or animal subject. Accordingly, in some embodiments, the compositions described herein can be used to alter gene expression in cells or tissues in vitro and/or in vivo by efficient delivery of oligonucleotide cargo to such cells or tissues.

In some embodiments, exosomes can be specifically targeted to a desired cell type or tissue type, e.g., damaged or diseased tissues. For example, exosomes can be specifically targeted to a desired cell type or tissue type by expression of a targeting peptide on the exosome surface. The targeting peptide can bind to a moiety present on the surface of the desired target cells. For example, expression of a specific cell-surface marker can be induced on the exosome, which results in specific interaction with a receptor on a desired target tissue.

Suitable targeting peptides are those which bind to cell surface moieties, such as receptors or their ligands, found on the cell surface of the cell to be targeted. Examples of suitable targeting moieties are short peptides, scFv and complete proteins, so long as the targeting peptide can be expressed on the surface of the exosome. In some embodiments, targeting peptides are full-length proteins. In other embodiments, targeting peptides are fragments of full-length proteins. In some examples, targeting peptides are than 100 amino acids in length, for example less than 50 amino acids in length, less than 30 amino acids in length, to a minimum length of 10, 5 or 3 amino acids.

Targeting peptides can be selected to target particular tissue types such as muscle, brain, liver, pancreas and lung for example, or to target a diseased tissue such as a tumor. In a preferred embodiment, the exosomes are targeted to brain tissue. This can be achieved using a targeting peptide that interacts with a neuronal cell surface marker. Exemplary neuronal cell surface markers include, but are not limited to GM1, Neun etc. RVG peptides and the peptide part of tetanus and cholera toxin can also be used in some embodiments to specifically target exosomes to neurons.

The targeting peptide targeting can be localized to the surface of the exosome by expressing it as a fusion protein with an exosomal transmembrane protein. A number of proteins are known to be associated with exosomes. Exemplary exosomal transmembrane proteins include but are not limited to Lamp-1, Lamp-2, CD1 3, CD86, Flotillin, Syntaxin-3, CD2, CD36, CD40, CD40L, CD41a, CD44, CD45, ICAM-I, Integrin alpha4, LiCAM, LFA-I, Mac-1 alpha and beta, Vti-1 A and B, CD3 epsilon and zeta, CD9, CD1 8, CD37, CD53, CD63, CD81, CD82, CXCR4, FcR, GluR2/3, HLA-DM (MHC II), immunoglobulins, MHC-I or MHC-II components, TCR beta and tetraspanins. In certain embodiments, the exosomal transmembrane protein is Lamp-1, Lamp-2, CD1 3, CD86, Flotillin, or Syntaxin-3. In an exemplary embodiment, the exosomal transmembrane protein is Lamp-2.

The exosomal transmembrane protein can be modified to incorporate a targeting moiety. For example, the exosomal transmembrane protein can be expressed as a fusion protein comprising the targeting peptide. The targeting peptide is incorporated into the transmembrane protein such that it will be positioned on the surface of the exosomes. The targeting peptide can be introduced into the exosome by expressing a fusion protein comprising the targeting peptide and the exosomal transmembrane protein (or a portion thereof) within a cell used to produce the exosomes. Expression of this fusion protein in the cell allows for the fusion protein to be incorporated into the exosome as it is produced from the cell. This process is described in, for example, US2013/0053426, the entire contents of which are incorporated herein by reference.

Antibodies and antibody fragments, e.g., scFv antibody fragments, can also be used as targeting peptides to target specific antigens, such as NGFR for neuronal targeting. In addition, natural ligands for receptors can be expressed as fusion proteins to promote exosome targeting. By way of example, NGF and fragments thereof binds NGFR and thereby confers neuron-specific targeting.

In other embodiments, targeting of the exosomes is not performed.

In one embodiment, the native contents of the exosome are removed and replaced with desired exogenous proteins or nucleic acids. In another embodiment, the native contents of exosomes are supplemented with desired exogenous proteins or nucleic acids.

Exosomes loaded with hydrophobically modified oligonucleotide cargo can be used therapeutically in subjects, i.e., human subjects or animal subjects. Accordingly, in one aspect, the invention features a method of treating a disease or disorder in a subject, by administering to the subject a composition comprising exosomes loaded with hydrophobically modified oligonucleotide cargo. Any of the hydrophobically modified oligonucleotide molecules described herein are suitable cargo for such methods of treatment. Likewise, any of the exosomal preparations described herein are suitable for use in methods of treatment. The particular oligonucleotide cargo can be selected based upon the disease or disorder to be treated. Non-limiting examples of oligonucleotide molecules which can be utilized in methods of treatment when loaded into exosomes as described herein include siRNA, siRNA-GalNAc, antisense, Locked Nucleic Acids (LNAs), hairpin siRNA, phosphorodiamidate morpholino oligomers (PMOs), miRNA, and oligonucleotide miRNA inhibitors. In some embodiments, the oligonucleotide cargo is an siRNA, a hairpin RNA, or a miRNA.

In some embodiments, hydrophobically modified oligonucleotide cargo is selected that reduces or inhibits expression of a gene associated with a disease or disorder.

For example, in a method of treating Huntington's disease, hydrophobically in 5 modified oligonucleotides targeting a mutant allele of the huntingtin gene are incorporated into the exosomes that are administered to a subject. Accordingly, in one embodiment, the invention provides a method of treating Huntington's disease in a subject, by administering to the subject a composition comprising exosomes loaded with hydrophobically modified oligonucleotide that reduces expression of a mutant allele of the huntingtin gene in the subject. In an exemplary embodiment, the oligonucleotide is an siRNA. In a method of treating Huntington's disease, it may be desirable to utilize exosomes that target neuronal cells. In some embodiments, such exosomes are derived from neuronal cells. In other embodiments, the exosomes are derived from stem cells, e.g., iPS cells. In other embodiments, the exosomes are synthetic exosomes. In some embodiments, the exosomes contain a targeting peptide which targets the exosomes to neuronal cells. In other embodiments, the exosomes do not contain a targeting peptide.

In another example, in a method of treating Amyotrophic Lateral Sclerosis (ALS), hydrophobically modified oligonucleotides targeting a mutant allele of the superoxide dismutase 1 (SOD1) gene are incorporated into the exosomes that are administered to a subject. Accordingly, in one embodiment, the invention provides a method of treating ALS in a subject, by administering to the subject a composition comprising exosomes loaded with hydrophobically modified oligonucleotide that reduces expression a mutant allele of SOD1 in the subject. In an exemplary embodiment, the oligonucleotide is an siRNA. In a method of treating ALS, it may be desirable to utilize exosomes that target neuronal cells. In some embodiments, such exosomes are derived from neuronal cells. In other embodiments, the exosomes are derived from stem cells, e.g., iPS cells. In other embodiments, the exosomes are synthetic exosomes. In some embodiments, the exosomes contain a targeting peptide which targets the exosomes to neuronal cells. In other embodiments, the exosomes do not contain a targeting peptide.

Other non-limiting examples of diseases or disorders that can be treated by administration of exosomes loaded with hydrophobically modified oligonucleotide cargo in accordance with the methods of the invention are set forth in Table 1. Exemplary genes that can be targeted by the hydrophobically modified oligonucleotide cargo in each instance are also provided.

TABLE 1

| Exemplary Disorders Treatable by Administration of Exosomes Loaded with Hydrophobically Modified Oligonucleotide Cargo | |
| --- | --- |
| Disorder | Gene Target(s) |
| Huntington's disease | Htt |
| Amyotrophic lateral sclerosis | SOD1, C9orf72 |
| Spinocerebellar ataxias (SCA) | ATXN1 |
| SCA1 | |
| SCA3 | ATXN3 |
| SCA6 | CACNA1 |
| Parkinson's disease | a-synuclein |
| | LRRK2 |
| | GAD67 |
| Alzheimer's disease | APP |
| | PS1 |
| Multiple sclerosis | Act1 |
| Prion disease | PrP(C) |
| Crohn's disease, IBD | ICAM-1 |
| Ulcerative colitis | ICAM-1 |
| Rheumatoid arthritis | TNF-α |
| HIV | Gag |
| CMV retinitis | CMV mRNA |
| Ovarian cancer | C-rat |
| Cancer | Hif-1α |
| CML | c-Myb |
| Solid cancer: ovarian and others | c-Raf |
| Cancer (e.g., malignant melanoma, NHL, CLL, MM, NSCLC) | Bcl-2 |
| Cancer | Hsp27 |
| Solid cancer | Survivin |
| Solid tumors | eIF-4E |
| Prostate, breast and lung cancers | Clusterin |
| Malignant glioma | TFT-β2 |

TABLE 1-continued

Exemplary Disorders Treatable by Administration of Exosomes
Loaded with Hydrophobically Modified Oligonucleotide Cargo

| Disorder | Gene Target(s) |
|---|---|
| Lymphomas and solid cancers | Ribonucleotide reductase R1 |
| Renal cancer | Ribonucleotide reductase R2 |
| Solid tumors | XIAP |
| Metastatis renal cancer | DNA methyltransferase |
| Head and neck cancer | DNA methyltransferase |
| Colon cancer, breast cancer and brain cancer | MDM2 |
| Prostate cancer | IGFBP2 and IGFBP5 |
| Prostate cancer | HSP27 |
| Asthma | IL4R-alpha |
| Hypercholesterolemia | Apo-B100 |
| Diabetes | PTP-1B |
| HCV | HCV IRES |
| Type II diabetes | Glucagon receptor |
| Restenosis | c-Myc mRNA |
| Polycystic kidney disease | c-Myc mRNA |
| Cancer | c-Myc mRNA |
| Cardiovascular disease | c-Myc inhibitor |
| Myasthenia gravis | AchE |
| Cancer/metabolism | Cyp 3A4 |
| Muscular dystrophy | Dystrophin |
| Multiple sclerosis | VLA-4 |
| Diabetes type I | CD40, CD80, CD86 in dentritic cells |
| Diabetic retinopathy | c-Raf |
| Age-related macular edema (AMD), Diabetic macular edema | VEGF |
| Acute kidney injury | P53 |
| Pachyonychia congenital | Mutant keratin |
| Metastatic melanoma | immunoproteasome |
| Liver cancer | VEGF KSP |
| Chronic nerve atrophy Nonarteritic ischemic optic neuropathy | Caspase 2 |
| Intraocular pressure and glaucoma | β-adrenergic receptor 2 |
| Ovarian cancer | Furin |
| Transthyretin amyloidosis | Transthyretin |
| Operable pancreatic ductal adenocarcinoma | Mutated KRAS |
| Solid cancers and lymphoma | Polo-like kinase |
| Hypercholesterolemia | PCSK9 |
| Dermal scarring | CTGF |
| HIV infection | CCR5 |
| Familial amyloid polyneuropathy | TTR |
| Acromegaly | Growth hormone receptor |

Exosomes loaded with hydrophobically modified oligonucleotide cargo that are administered to a subject or used in methods of treatment include those produced according to any of the methods described herein.

The exosomal compositions described herein can be administered to a subject (i.e., a human or animal subject) by any suitable means. For example, appropriate routes of administration include parenteral, intramuscular, intracerebral, intravascular, subcutaneous, or transdermal. In preferred embodiments, the mode of administration is by injection, e.g., intramuscular or intravenous injection. A physician will be able to determine the mode of administration appropriate for a given subject.

Exosome administration may be by local or systemic administration. Local administration, depending on the tissue to be treated, may in some embodiments be achieved by direct administration to a tissue (e.g., direct injection, such as intratumoral injection, intramyocardial injection, or injection of neuronal cells or tissue). Local administration may also be achieved by, for example, lavage of a particular tissue (e.g., intra-intestinal or peritoneal lavage). In several embodiments, systemic administration is used and may be achieved by, for example, intravenous and/or intra-arterial delivery. In certain embodiments, intracoronary delivery is used.

In some embodiments, subcutaneous or transcutaneous delivery methods are used. Due to the relatively small size, exosomes are particularly advantageous for certain types of therapy because they can pass through blood vessels down to the size of the microvasculature, thereby allowing for significant penetration into a tissue. In some embodiments, this allows for delivery of the exosomes directly to central portion of the damaged or diseased tissue (e.g., to the central portion of a tumor or an area of infarcted cardiac tissue). In addition, in several embodiments, use of exosomes is particularly advantageous because the exosomes can deliver their payload (e.g., the resident nucleic acids and/or proteins) across the blood brain barrier, which has historically presented an obstacle to many central nervous system therapies. In certain embodiments, however, exosomes may be delivered to the central nervous system by injection through the blood brain barrier.

In some embodiments, exosomes are directly infused into the tissue of interest. For example, exosomes can be directly infused into the brain, e.g., by intra-striatal injection. As demonstrated herein, intra-striatal infusion of exosomes loaded with hydrophobically modified oligonucleotide results in bilateral distribution. The constructs can delivered as a composition, e.g., a pharmaceutical composition, as described herein. The composition may be formulated for parenteral, intramuscular, intracerebral, intravascular (including intravenous), subcutaneous, or transdermal administration. Compositions for parenteral administration may include sterile aqueous solutions which may also contain buffers, diluents and other suitable additives. The constructs of the invention may be formulated in a pharmaceutical composition, which may include pharmaceutically acceptable carriers, thickeners, diluents, buffers, preservatives, and other pharmaceutically acceptable carriers or excipients and the like in addition to the exosomes.

A "pharmaceutically acceptable carrier" (excipient) is a pharmaceutically acceptable solvent, suspending agent or any other pharmacologically inert vehicle for delivering exosomes to a subject. Typical pharmaceutically acceptable carriers include, but are not limited to, binding agents (e.g., pregelatinised maize starch, polyvinylpyrrolidone or hydroxypropyl methylcellulose, etc); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.).

The compositions provided herein may additionally contain other adjunct components conventionally found in pharmaceutical compositions. Thus, for example, the compositions may contain additional compatible pharmaceutically-active materials or may contain additional materials useful in physically formulating various dosage forms of the composition of present invention, such as dyes, flavouring agents, preservatives, antioxidants, opacifiers, thickening agents and stabilizers. However, such materials, when added, should not unduly interfere with the biological activities of the components of the compositions provided herein.

A therapeutically effective amount of exosomal compositions are administered to subjects. The dose may be determined according to various parameters, especially according to the severity of the condition, age, and weight of the patient to be treated; the route of administration; and the required regimen. A physician will be able to determine the required route of administration and dosage for any particular patient. Optimum dosages may vary depending on the relative potency of individual constructs, and can generally be estimated based on EC50s found to be effective in vitro and in in vivo animal models.

The dose of exosomes administered, depending on the embodiment, ranges from about $1.0 \times 10^5$ to about $1.0 \times 10^9$ exosomes, including about $1.0 \times 10^5$ to about $1.0 \times 10^6$, about $1.0 \times 10^6$ to about $1.0 \times 10^7$, about $1.0 \times 10^7$ to about $5.0 \times 10^7$, about $5.0 \times 10^7$ to about $1.0 \times 10^8$, about $1.0 \times 10^8$ to about $2.0 \times 10^8$, about $2.0 \times 10^8$ to about $3.5 \times 10^8$, about $3.5 \times 10^8$ to about $5.0 \times 10^8$, about $5.0 \times 10^8$ to about $7.5 \times 10^8$, about $7.5 \times 10^8$ to about $1.0 \times 10^9$, and overlapping ranges thereof. In certain embodiments, the exosome dose is administered on a per kilogram basis, for example, about $1.0 \times 10^4$ exosomes/kg to about $1.0 \times 10^9$ exosomes/kg. In additional embodiments, exosomes are delivered in an amount based on the mass of the target tissue, for example about $1.0 \times 10^4$ exosomes/gram of target tissue to about $1.0 \times 10^9$ exosomes/gram of target tissue. In several embodiments, exosomes are administered based on a ratio of the number of exosomes to the number of cells in a particular target tissue, for example exosome: target cell ratio ranging from about $10^9$:1 to about 1:1, including about $10^8$:1, about $10^7$:1, about $10^6$:1, about $10^5$:1, about $10^4$:1, about $10^3$:1, about $10^2$:1, about 10:1, and ratios in between these ratios. In additional embodiments, exosomes are administered in an amount about 10-fold to an amount of about 1,000,000-fold greater than the number of cells in the target tissue, including about 50-fold, about $10^0$-fold, about 500-fold, about 1000-fold, about 10,000-fold, about $10^{0,000}$-fold, about 500,000-fold, about 750,000-fold, and amounts in between these amounts. In certain embodiments, the dosage is from 0.01 mg/kg to 100 mg per kg of body weight. For example, a daily dose can range from about 0.1 to 50 mg per kg, preferably from about 0.1 mg/kg to 10 mg/kg of body weight, according to the potency of the specific construct, the age, weight and condition of the subject to be treated, the severity of the disease and the frequency and route of administration. Different dosages of the construct may be administered depending on whether administration is by intramuscular injection or systemic (intravenous or subcutaneous) injection. In an exemplary embodiment, the dose of a single intramuscular injection is in the range of about 5 to 20 μg. In another exemplary embodiment, the dose of single or multiple systemic injections is in the range of 10 to 100 mg/kg of body weight.

In several embodiments, the exosomes are delivered in a single, bolus dose. In some embodiments, however, multiple doses of exosomes may be delivered. In certain embodiments, exosomes can be infused (or otherwise delivered) at a specified rate over time. Due to construct clearance (and breakdown of any targeted molecule), the patient may have to be treated repeatedly, for example once or more daily, weekly, monthly or yearly. Persons of ordinary skill in the art can easily estimate repetition rates for dosing based on measured residence times and concentrations of the construct in bodily fluids or tissues.

VII. Kits

In another aspect, the present invention provides a kit for producing a population of exosomes loaded with hydrophobically modified oligonucleotide.

In one embodiment, the kit includes a population of exosomes and instructions for loading the exosomes with hydrophobically modified oligonucleotide.

In another embodiment, the kit includes a hydrophobically modified oligonucleotide and instructions for incorporating the oligonucleotide into exosomes.

In another embodiment, the kit includes a composition comprising a population of exosomes loaded with hydrophobically modified oligonucleotide, and instructions for administration of the composition to a subject.

In another embodiment, the kit includes a population of exosomes, and a hydrophobic moiety suitable for conjugation to an oligonucleotide molecule, together with instructions for preparing a hydrophobically modified oligonucleotide, and instructions for loading the hydrophobically modified oligonucleotide into exosomes.

The kits of the invention can optionally contain additional components useful for performing the methods of the invention.

By way of example, the kits can contain reagents suitable for incubating exosomes with hydrophobically modified oligonucleotides. In another example, the kits can contain reagents suitable for purification of exosomes prior to or subsequent to loading with hydrophobically modified oligonucleotides.

In another embodiment, the kits of the invention provide reagents and/or instructions for determining the loading efficiency of hydrophobically modified oligonucleotides into exosomes.

The invention is further illustrated by the following examples, which should not be construed as limiting. The entire contents of all references, patents and published patent applications cited throughout this application are hereby incorporated by reference in their entirety.

EXAMPLES

The experiments described herein demonstrate a simple and robust method to efficiently load exosomes with oligonucleotide cargo. Loaded exosomes mediated efficient and non-toxic internalization of hydrophobically modified siRNA (hsiRNA) and dose-dependent silencing. This data provides a path to utilize exosomes as highly efficient vehicles for delivery of oligonucleotides in vivo and in vitro.

Example 1: Exosome Production, Purification and Quality Control from Conditioned Media of U87s, BMDCs, HeLa, Huh7 Cells Exosomes were produced from conditioned media derived by growing several types of cultured cells, including U87, BMDCs, HeLa, and Huh7. Media was conditioned for various periods of time (2 hours to 72 hours). Exosomes from conditioned media were purified using a differential ultracentrifugation method (Thery, C., et al., *Isolation and characterization of exosomes from cell culture supernatants and biological fluids*. Curr Protoc Cell Biol, 2006. Chapter 3: Unit 3 22). The differential centrifugation protocol is outlined in FIG. 1A. Briefly, cells were cultured in exosome free media. The media was harvested, and centrifuged at 300 g for 10 minutes to remove cells. The media was then centrifuged at 2000 g for 10 minutes to remove any remaining dead cells, and was subsequently centrifuged at 10000 g for 30 minutes to remove cellular debris. The supernatant was filtered using a 0.2 μm filter, and the filtrate was spun in an ultracentrifuge at 100,000 g for 70 minutes to pellet exosomes. The pellet was washed in PBS, and the sample was spun in an ultracentrifuge at 100,000 g for 70 minutes. The pellet contained an isolated population of exosomes. Alternatively exosomes were purified using commercially available kits like ExoQuick (System Bioscience) or Exosome Purification kit (Life Technology). In addition, exosomes can be purified by ultrafiltration or gel filtration (Thery, 2006).

Figure 1B:
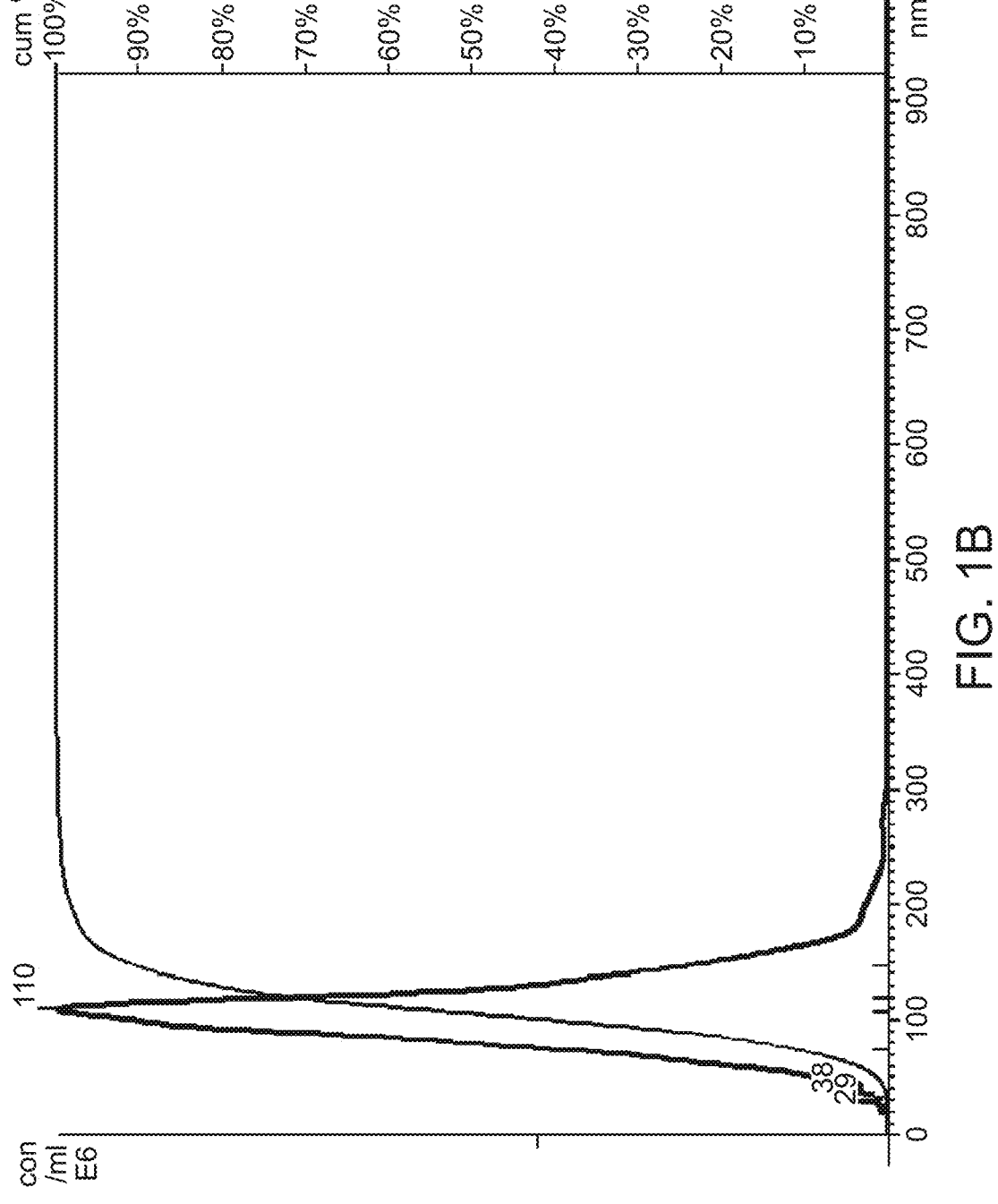
Figure 1C:
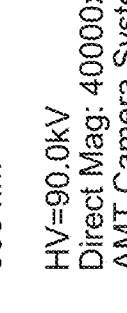

Purified exosome size and number was analyzed by light scattering using Nanosight (Malvern). The results of this analysis are presented in FIG. 1B. The average size of the exosomes was between 30-120 nm, with most of the preps having an average size of ~100-120 nM. In addition, electron microscopy was used to confirm exosome structure and integrity. A representative electron micrograph is shown in FIG. 1C. In summary, exosomes can be produced by wide range of cells and different methods can be used to purify a relatively homogeneous population, which can be used for loading of the vesicles with hydrophobically modified oligonucleotides.

Example 2: Efficient Incorporation of Hydrophobically Modified siRNAs into Exosomes Purified from U87 Cells Exosomes have been previously demonstrated to efficiently transfer natural RNAs between cells. It has been shown that exosomes can be used as delivery vehicles to deliver synthetic RNAs to cells, however, the efficiency of loading synthetic RNA into cells has been very low. For example, it has been reported that exosomes can be loaded with non-natural RNAs by several methods, including (1) making exosomes from cells over-expressing or pre-transferred with artificial RNAs, (2) electroporation or lipofection of RNAs into purified exosomes, and (3) co-ultra-precipitating exosomes with siRNAs. The efficiency of each of these methods is very low. It has been reported that loading exosomes with oligonucleotide using electroporation results in less than 1-2% of oligonucleotides being delivered (El-Andaloussi, S., et al., *Exosome-mediated delivery of siRNA in vitro and in vivo*. Nat Protoc, 2012. 7 (12): p. 2112-26) while interfering with exosome integrity (Kooijmans, S. A., et al., *Electroporation-induced siRNA precipitation obscures the efficiency of siRNA loading into extracellular vesicles*. J Control Release, 2013. 172 (1): p. 229-238). Other labs have used co-ultracentrifugation, resulting in less than one molecule of small RNA loaded per 1000 exosomes, and still demonstrated some functional outcomes (Bryniarski, K., et al., *Antigen-specific, antibody-coated, exosome-like nanovesicles deliver suppressor T-cell microRNA*-150 *to effector T cells to inhibit contact sensitivity*. J Allergy Clin Immunol, 2013. 132 (1): p. 170-81). Hydrophobic modifications of oligonucleotides have been used to enhance delivery to cells. The experiments described herein were designed to explore whether hydrophobic modification of oligonucleotides can be used as way to load exosomes with artificial oligonucleotides such as RNAs.

Figure 2A:
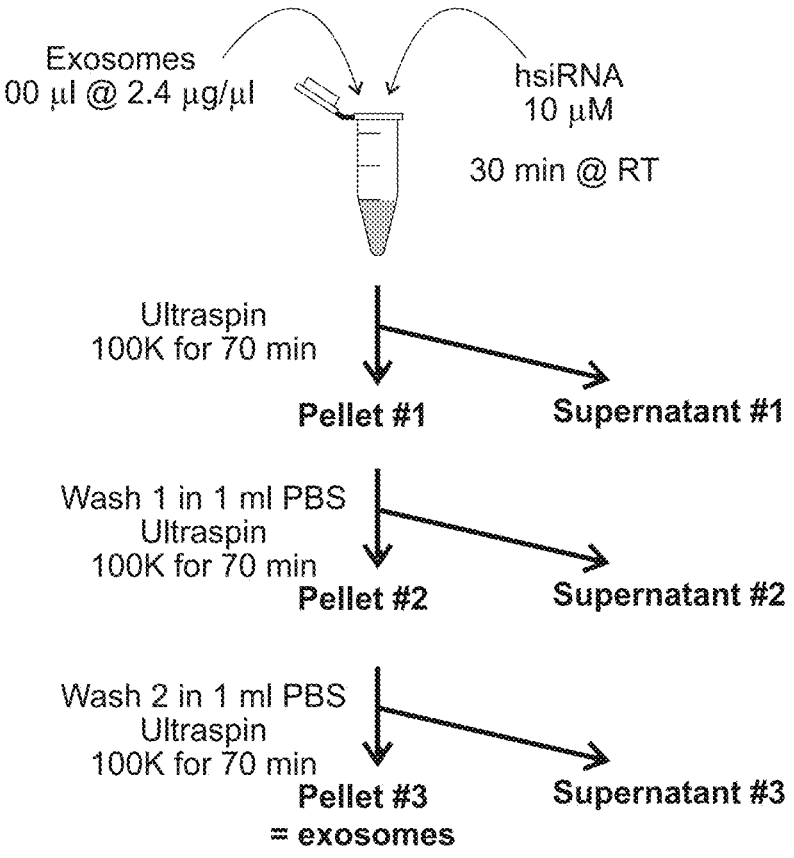
FIG. 2A-D. Efficient loading of hydrophobically modified siRNA (hsiRNA) into Exosomes. A. Loading and purification scheme. B. % of DY547-hsiRNA bound to exosomes and free in solution after ultracentrifugation were measured by nandrop/Q-RT-PCR. ~25% of hsiRNA were bound to exosomes stably as less than 5% is released after the second spin. No hsiRNA were precipitated in the absence of exosomes. C. Nanosight profile of exosomes before and after hsiRNA loading (treated in parallel). In presence of exosomes we observe a clear increase in size and shift in the zeta potential (Melvern). D. Electron microscopy of Exosomes loaded with Biotinylated Htt-hsiRNA detected by streptavidin/Immunogold particles used to detect the biotin-hsiRNA. The arrows indicate exosomes with biotin-hsiRNA on surface.

Exosomes isolated according to Example 1 were loaded with hydrophobically modified siRNA (hsiRNA). The exosome loading and purification scheme are depicted in FIG. 2A. Briefly, exosomes (100 μl @ 2.4 μg/μl) were added to a microcentrifuge tube with hsiRNA (10 μM), and were incubated at room temperature for 30 minutes. Tubes were spun at 100,000 g for 70 minutes. The pellet was washed in 1 mL PBS, and the tubes were spun for a second time at 100,000 g for 70 minutes. The second pellet was washed in 1 mL of PBS, and the tubes were spun for a third time at 100,000 g for 70 minutes. The third pellet contained exosomes loaded with hsiRNA.

Figure 2B:
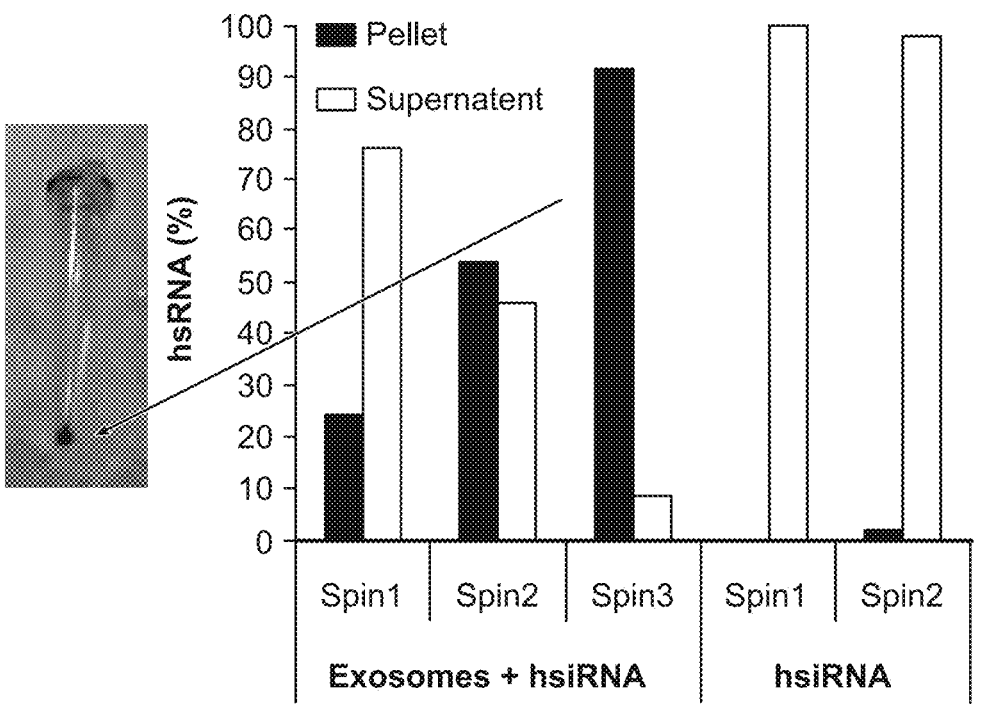
Figure 2C:
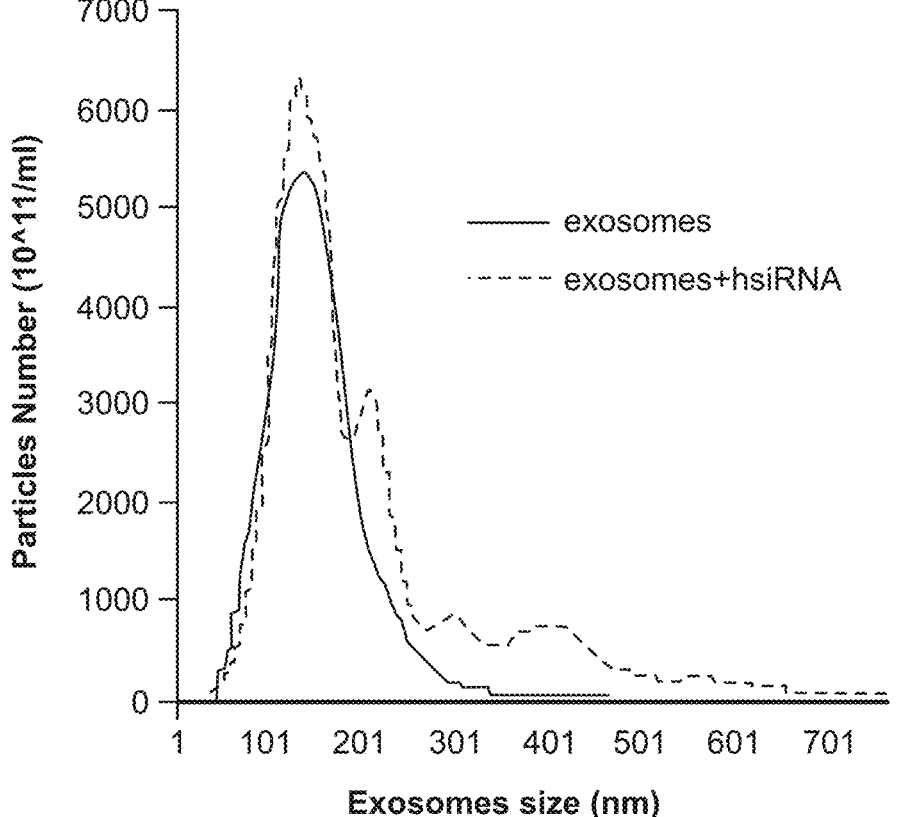

The sterol conjugates stabilized Cy-labeled-siRNAs (10 μM final concentration) were mixed with exosomes derived from U87 cell conditioned media and incubated for 30 minutes at room temperature (RT). 5 minutes to 3 hours incubation times at different temperatures (ranging from RT-37° C.) were tested and produced similar results. We decided to evaluate whether hsiRNAs described above can be loaded into exosomes. Indeed, when the exosome preparation was incubated with 10 μM Dy547-hsiRNA for 1 hour at 37° C., we observed ~25% of the molecules associated with the exosomal pellet after ultracentrifugation. In addition, almost no RNA was released in the media after the 3$^{rd}$ spin indicating that binding is stable. This data is depicted in FIG. 2B. The size distribution and Z-potential of exosomes was measured before and after hsiRNA loading (FIG. 3C). A slight shift in size was observed, and an expected change in Z potential (from −5 to −24), oligo fluorescence tracking with the larger exosomes, consistent with exosome association with negatively charged oligonucleotides. To separate exosome-associated RNA from non-bound hydrophobic siRNA the ultracentrifugation was performed again. A significant part of the fluorescence appeared in pellet (~25%). The pellet was bright pink confirming that fluorescently labeled siRNAs were associated with the exosomes. Ultracentrifugation of the hsiRNA alone did not generate any visible precipitant. The pellet was re-suspended in PBS and washed twice. After a second re-centrifugation, the majority of the compound stayed associated with exosomes. The loaded exosomes have slightly shifted Nanosight profiles with a majority of vesicles maintaining the original size. The Zeta membrane potential for loaded exosomes was decreased from −5.7 to −21.2 mV, confirming negatively charged RNA association with exosomal membrane. This data supports efficient and productive loading of exosomes with chemically synthesized hsiRNA.

Figure 2D:
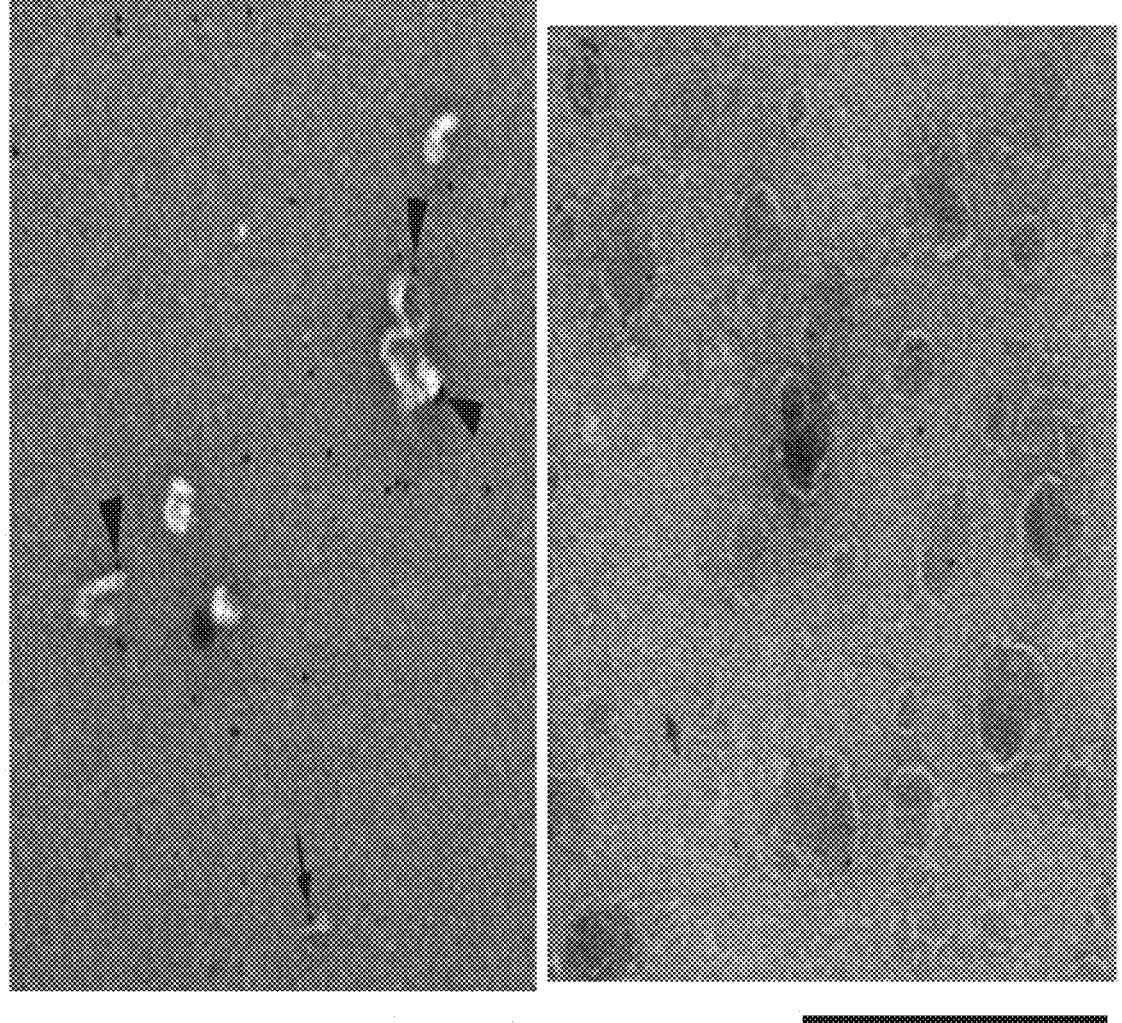

To further evaluate whether s majority of hydrophobically labeled siRNAs are associated with the surface of exosomes or internalized, U87 produced exosomes were incubated with biotinylated, hydrophobically modified siRNAs. The streptavidin gold particles in combination with electron microscopy were used to detect hydrophobic siRNA localization (FIG. 2D). Gold particles were detected both inside and on the surface of exosomes confirming the oligonucleotides are both internalized and are bound to the exosomal membrane.

This data together indicated that hydrophobically modified siRNA efficiently associates with exosomes with more than 25% of added oligonucleotides being incorporated in vesicles.

Examples of hydrophobic oligonucleotide modifications are depicted in FIG. 3.

Example 3: Fractionation of Exosome-siRNA Complexes by Gel-Filtration

Figures 4A, 4B, 4C:
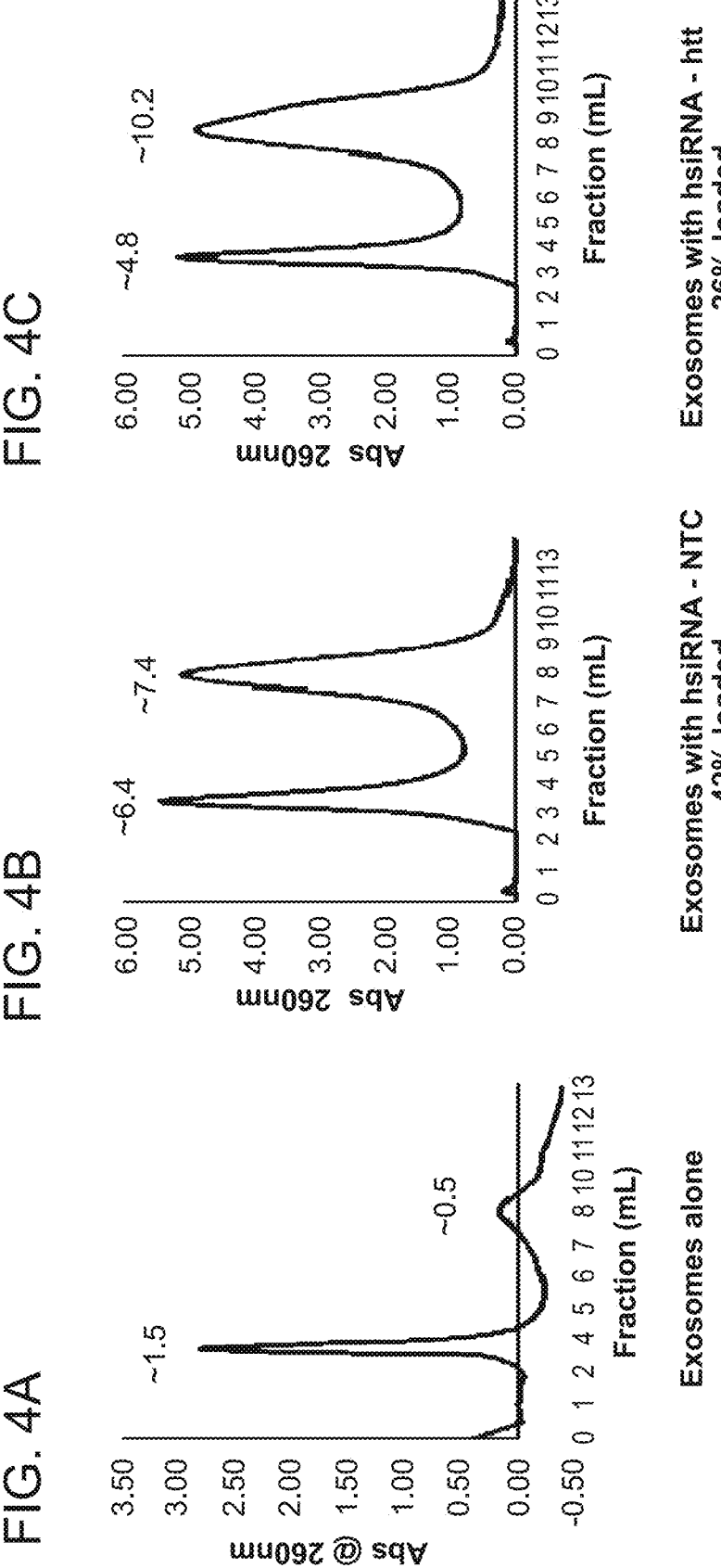
FIG. 4A-C. Optimization of exosome loading with RNAi agents using Sephacryl S-1000 Fractionation. Exosomes purified from U87 cells and purified by ultracentrifugation were loaded with in the presence of 10 µM hsiRNA (NTC and htt targeting). Samples were fractionated in PBS on Sephacryl S-1000 at 0.5 ml/min. A. Profile of absorbance at 260 nm of non-loaded exosomes. B. Profile of absorbance at 260 nm of exosomes loaded with hsiRNA NTC.C. Profile of absorbance at 260 nm of exosomes loaded with hsiRNA htt. Efficient loading (26-42%) was observed.

To further evaluate the percentage of hydrophobically modified oligos associated with exosomes, the oligo-exosome mixtures were fractionated on a Sephacryl S-1000 gel filtration column (FIG. 4). Exosomes were eluted in a void volume. Several preps were fractionated using this method. Non-Targeting Control sterol conjugated siRNA was incubated with U87 derived exosomes for 1 hour at 37° C. Approximately 43% of oligo stayed associated with exosomes after gel filtration. The sterol-conjugated siRNA targeting huntingtin was incubated with same exosomal prep and showed ~26% of oligo associated with exosomes. Consistent loading of hydrophobically modified oligonucleotides with exosomes (>25%) was confirmed with multiple siRNAs and antisense, multiple exosomal preps from different cell types by different methods, indicating that hydrophobic modification of oligonucleotides is a viable approach for loading artificial RNAs and DNAs into exosomes.

Figures 5A, 5B:
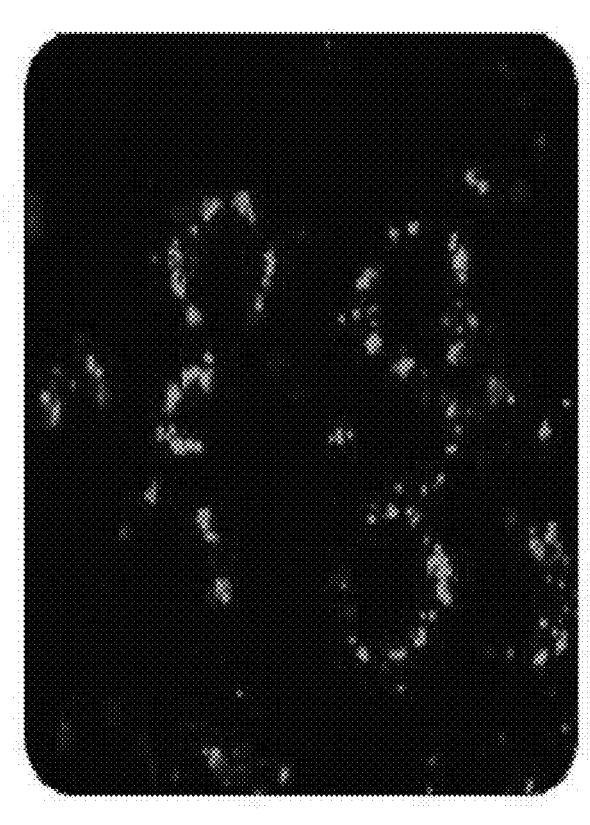
FIG. 5A-D. hsiRNA-Exosome Complexes: Passive vs. Exosome-mediated hsiRNA Uptake in HeLa cells. U87 cell-derived exosomes were purified by differential centrifugation and labeled by PKH67 dye (Sigma). HeLa cells were treated with exosomes (labeled with PKH67), hsiRNA and hsiRNA pre-formulated with exosomes. A. Exosomes alone (PKH67), 24 hours. B. hsiRNA alone, 12 hours; membrane and cytoplasmic staining C. hsiRNA-loaded exosomes, 12 hours; clear asymmetric peri-nuclear staining. D. hsiRNA (Cy3)-loaded exosomes (PKH67); degree of co-localization. Exosomes=green (PKH67 dye); hsiRNA=red (Cy3); nucleus=blue (dapi)
Figure 5D:
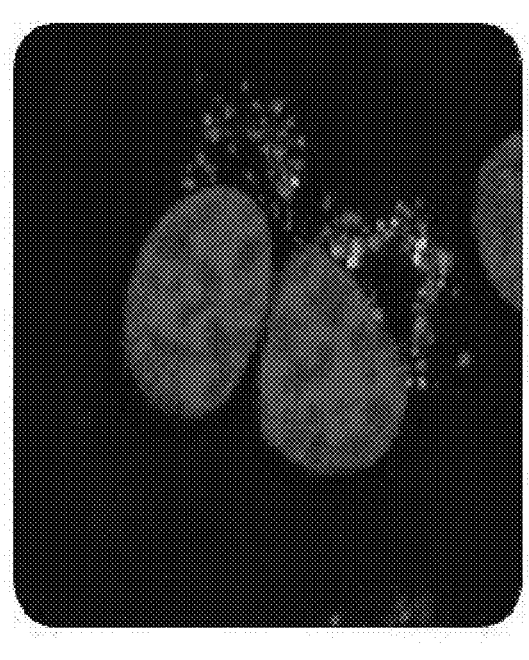
Figure 5C:
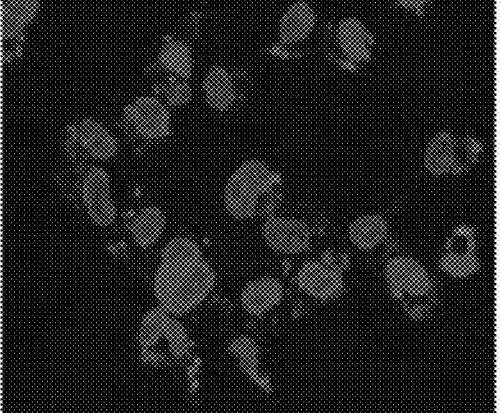

Example 4: Exosome Formulated Hydrophobic siRNAs are Efficiently Internalized by HeLa Cells, Mimicking Intracellular Localization of Unloaded Exosomes The prior examples demonstrate efficient loading of hydrophobically modified hsiRNA into exosomes by different methods. This example addresses whether the presence of the hydrophobically modified oligo can impact exosome trafficking, as hsiRNAs are capable of direct internalization. It was important to demonstrate that this method of exosome loading did not interfere with exosome biology and did not effect pathways normally utilized for exosome cellular trafficking. Exosome uptake in HeLa cells was studied (FIG. 5). Exosomes were labeled with PKH67 lipophilic dye (Sigma) and their kinetics of internalization were followed by confocal microscopy. Exosomes were internalized and detected within the cells in 6-12 hours.

As depicted in FIG. 5, intracellular localization of hsiRNA loaded exosomes closely resembled exosomes alone but was distinctly different from naked hsiRNAs. While hsiRNA was characterized by membrane and diffuse cytoplasmic vesicular presence, exosome loaded hsiRNAs showed distinct asymmetric peri-nuclear and no membrane localization. In addition, while hsiRNA was internalized instantaneously within minutes of exposure, no detectable internalization with exosome-formulated hsiRNA was observed for hours (similar to native exosomes), indicating that an alternative trafficking pathway was used. Taken together, this data demonstrates that hydrophobically modified oligonucleotide-loaded exosomes resemble native exosomes and this method can be used to efficiently load exosomes without interference with their native trafficking abilities. This approach can be highly valuable in situations in which exosomes are considered as a potential therapeutic.

Figure 6A:
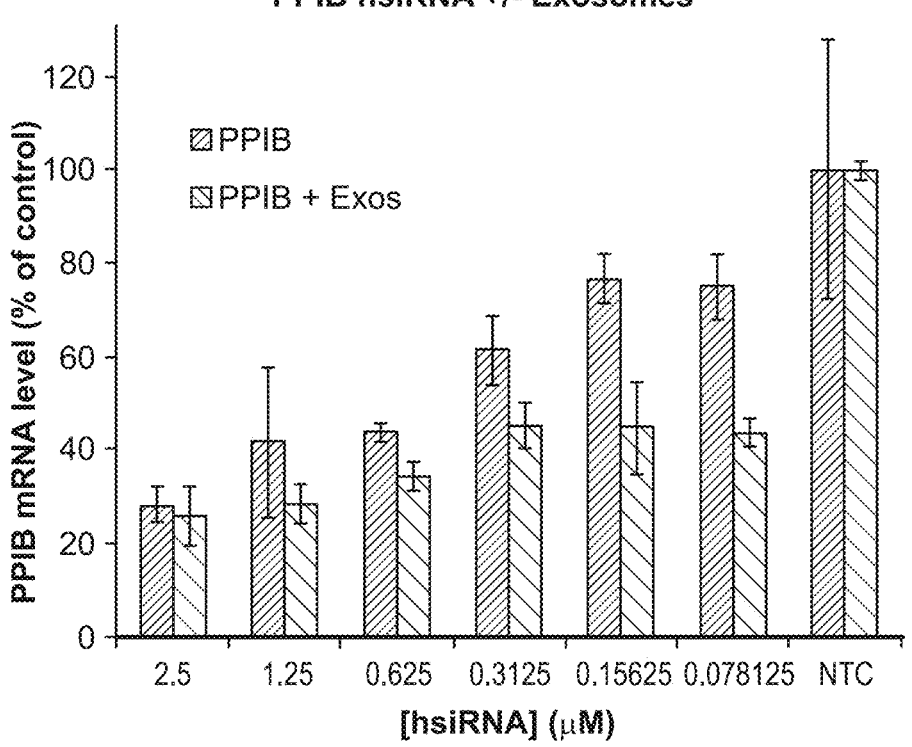
FIGS. 6A and B. Comparison of silencing efficiency: hsiRNA passive vs. exosome-mediated hsiRNA functionality test in HeLa cells. U87 cell-derived exosomes were purified by differential centrifugation. A. HeLa were treated with hsiRNA-PPIB alone or PPIB hsiRNA into loaded exosomes. The level of PPIB silencing was measured at 72 hours, using HTT as housekeeping (QuantiGene 2.0 assay, Affimetrix). B. Comparison of silencing efficiency of PPIB hsiRNA alone or mediated by exosomes.
Figure 6B:
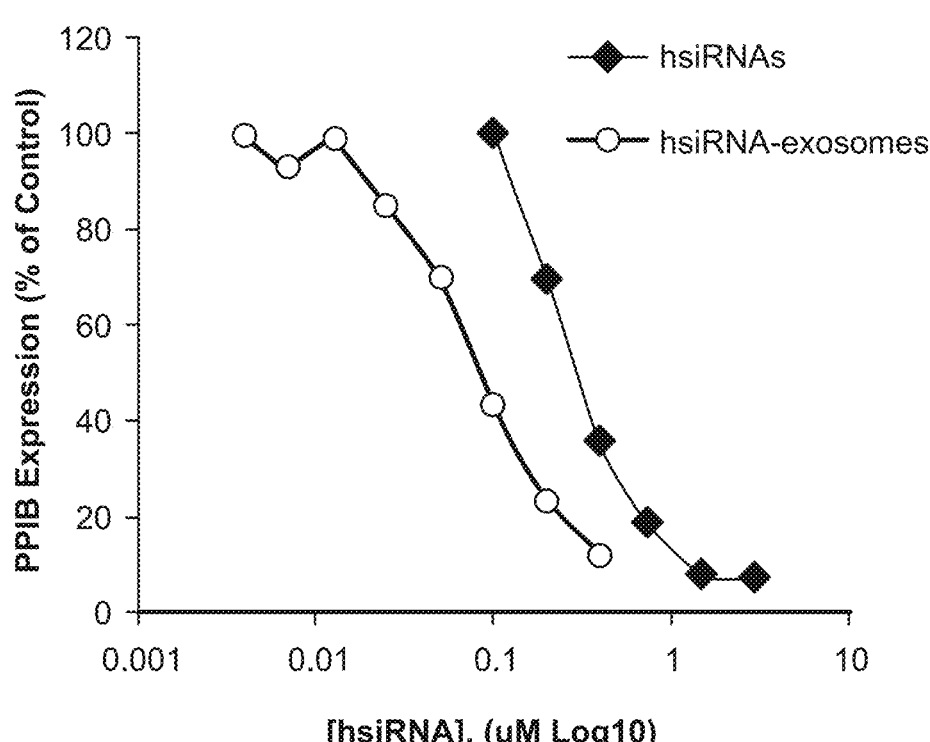

Example 5: Exosome Formulated Hydrophobic siRNA Mediates Gene Silencing in HeLa Cells This example demonstrates that uptake of siRNA loaded exosomes results in productive gene silencing. Sterol modified siRNA targeting PPIB, and non-targeting control, were incubated with U87 derived exosomes. SiRNA-exosome complexes were purified by ultracentrifugation and siRNA loading and exosome integrity was confirmed by Nanosight. HeLa cells were treated with hydrophobically modified siRNA alone, siRNA-exosomes complexes, and non-loaded exosomes. Only PPIB-siRNA loaded exosomes show dose dependent silencing of PPIB (Cyclophilin B), as depicted in FIG. 6A. The presence of exosomes enhanced efficacy as demonstrated by comparison with hydrophobically modified siRNA alone (FIG. 6B). The level of PPIB expression was determined by QuantiGene Assay and normalized to a house keeping gene. Thus exosome mediated siRNA uptake results in strong and specific gene silencing and can be used as a potential vesicle for therapeutic applications.

Figures 7A, 7B:
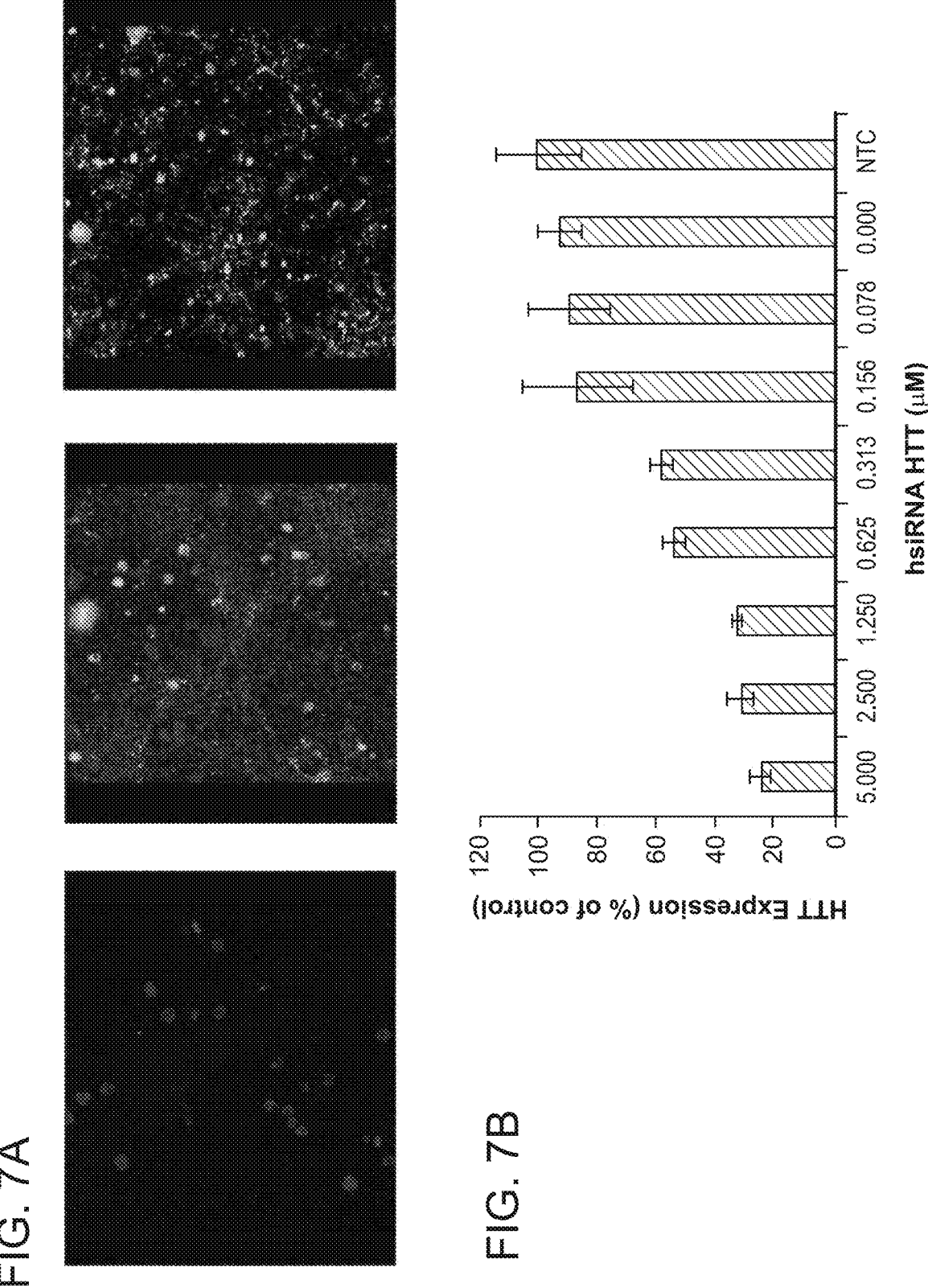
FIGS. 7A and B. hsiRNA-loaded exosomes in primary neurons: uptake and functionality monitoring of hsiRNA targeting PPIB and HTT mRNA. A. Exosomes from U87 cells were labeled with PKH67 (Sigma), loaded with Cy3-labeled hsiRNA (PPIB) and added at $10^8$ per well. Each well contained ~2*$10^6$ cell per well. Exosomes=green (PKH67 dye); hsiRNA=red (Cy3); nucleus=blue (dapi). B. Exosomes purified from U87 cells by standard differential centrifugation were loaded with hsiRNA against huntingtin mRNA: incubation for 1 hr at 37° C. and ultra-centrifuged. Loaded exosomes were then transferred onto WT (FVB) Primary Cortical Neurons (1×10⁵/well), followed by a week of incubation. Level of silencing was determined by QuantiGene Assay (housekeeping gene=PPIB; n=3, error is a STDEV).

Example 6: Efficient Internalization of Exosome Formulated Hydrophobic siRNAs by Primary Neurons and Exosome-Mediated Silencing of the Huntingtin Gene Hydrophobic siRNAs targeting huntingtin were loaded in U87 derived exosomes, purified by ultracentrifugation, and used to treat primary cortical neurons. Similar to the previously described experiment in HeLa cells, exosomes promoted uptake of fluorescently labeled siRNAs into primary neurons, and this uptake resulted in potent and specific gene known-down, as shown in FIG. 7. These experiments validate that hydrophobic modification of oligonucleotides is an efficient method for loading of exosomes, and the resulting hsiRNA-exosome complexes demonstrated efficient cellular uptake and gene specific silencing independent of the target gene and type of cells used.

Figures 8A, 8B:
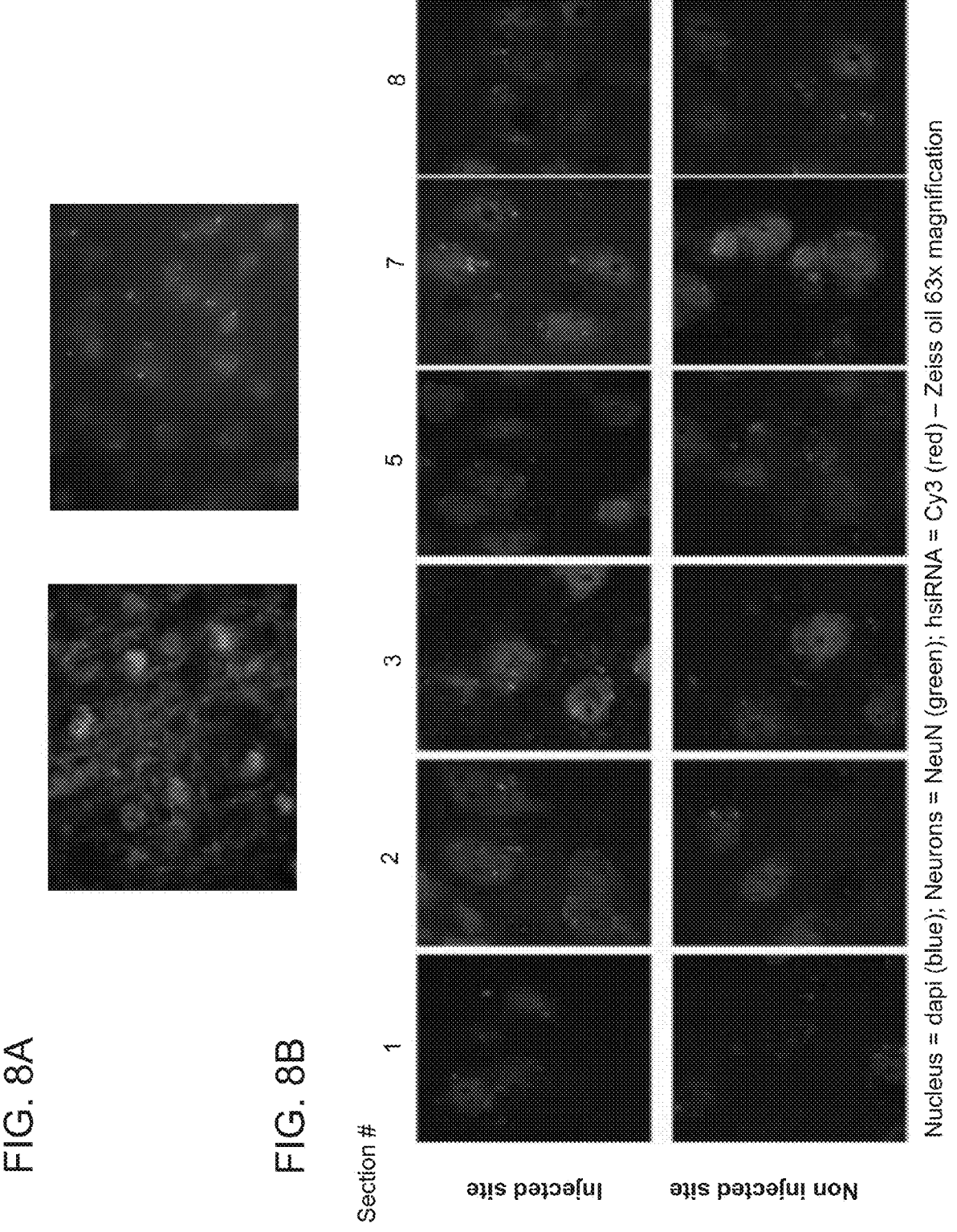
FIGS. 8A and B. In vivo distribution of hsiRNA-loaded exosomes in mouse brain. Exosomes purified from U87 cells were loaded with Cy3-labeled hsiRNA against HTT mRNA. A single injection of exosome-hsiRNA complexes was performed on mouse brain. Mice were sacrificed 24 h or 72 h after the injection. Neurons=NeuN staining (neuronal marker; green); hsiRNA=red (Cy3). A. Visualization of injected side (left) and non-injected side (right) of mouse brain by fluorescence microscopy. B. Visualization of brain sections from injected side (upper panel) and non-injected side (lower panel) of mouse brain fixed after 72 h after exosome-hsiRNA complex injection by fluorescence confocal microscopy.

Example 7: Exosome Formulated siRNAs Efficiently Distribute Through the Brain and Result in Targeted Delivery to Majority of Neurons hsiRNA-exosome complexes were further studied to determine whether they had the ability to distribute through the animal brain in vivo. Injection of hydrophobically modified siRNA resulted in limited brain distribution (majority of compounds stayed around the site of administration), and significant compounds associating with cellular matrix and some cellular uptake. Interestingly exosome mediated hsiRNA delivery into brain resulted in uniformly distribution throughout the brain and preferential delivery to neurons (FIG. 8, stained green with NeuN). This homogenous distribution represents a major breakthrough for therapeutic oligonucleotide delivery and confirms tissue culture data that loading of exosomes with hydrophobically modified oligonucleotide does not interfere with its ability to promote targeted and productive cellular uptake.

Example 8: Efficient Loading of Exosomes with Hydrophobically Modified siRNAs (hsiRNAs)

Figures 9A, 9B, 9C, 9D:
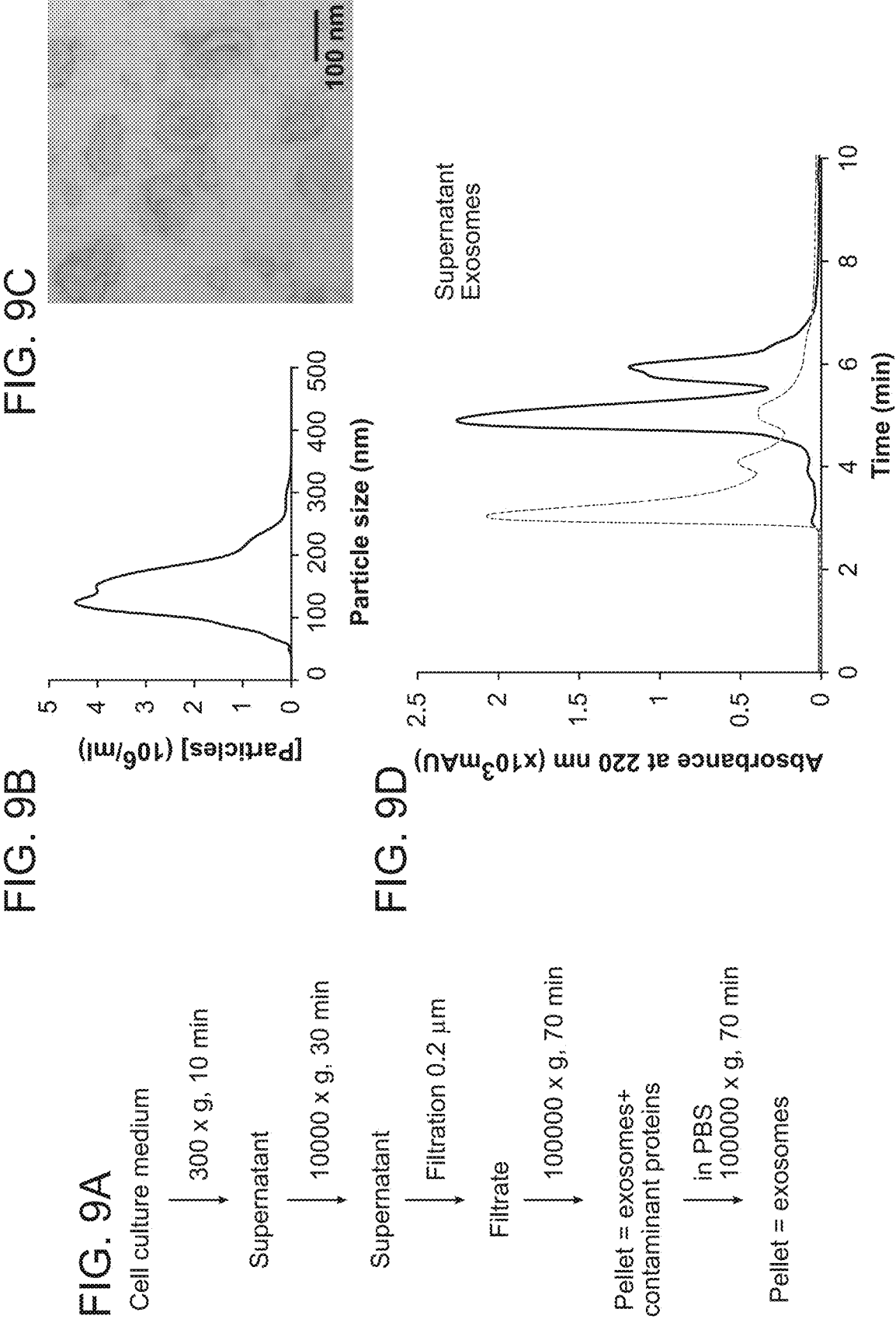
FIG. 9A-D. Exosome purification and characterization. (A) Schematic for an exosome purification procedure based on differential ultracentrifugation (Thery et al, 2006.). The speed and length of each centrifugation are indicated to the right of the arrows. After the first two centrifugations, pellets (cells, dead cells and cell debris) are discarded, and the supernatant is kept for the next step. In contrast, after the two 100,000 g centrifugations, pellets (exosomes+contaminant proteins, exosomes) are kept, and supernatants are discarded. (B) Quantification and size monitoring of U87 MG-derived vesicles by Nanoparticle Tracking Analysis. Particle concentration is shown as a function of particle size. (C) Electron microscopy validates vesicle integrity. (D) U87 glioblastoma cells were cultured in exosome-free medium for 3 days. Exosomes were purified from conditioned medium as described above. Following purification, 50 µl of conditioned medium or exosome sample were analyzed by size-exclusion chromatography.

In another experiment, exosomes were purified from conditioned medium of glioblastoma U87 cells by differential centrifugation (FIG. 9A) (Thery et al., 2006). Exosome enrichment was confirmed by size exclusion chromatography of conditioned medium, from which exosomes were purified. (FIG. 9D). Nanoparticle tracking analysis (NTA) showed that the purified exosomes had the expected size distribution peaking at 140 nm in diameter. Electron microscopy revealed the cup shape and double membrane features characteristic of exosomes (FIGS. 9B and C).

Figure 10A:
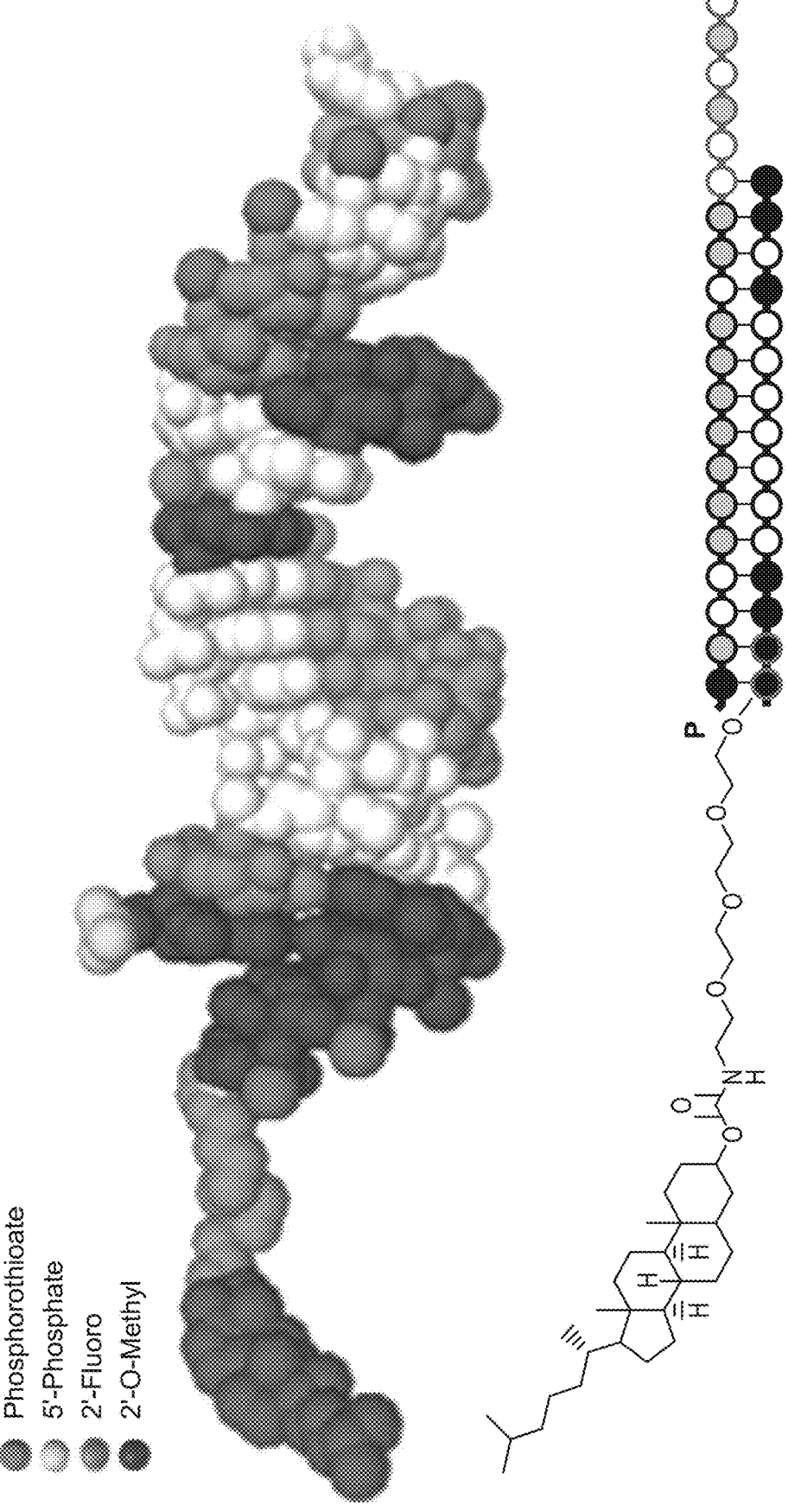
FIG. 10A-C. Efficient loading of exosomes with hydrophobically modified siRNAs (hsiRNAs). (A) The hsiRNAs used in this experiment are asymmetric compounds, with a short duplex region (15 base-pairs) and single-stranded fully phosphorothioated tail, where all pyrimidines are modified with 2'-fluoro and 2'-O-methyl modifications and the 3' end of the passenger strand is conjugated to Teg-Cholesterol. (B) Co-incubation of hsiRNAs and exosomes (U87-derived) results in ~1000 to 3000 hsiRNA association per exosome. hsiRNA-loaded exosomes were separated by ultracentrifugation. The pellet (pink) contains Cy3-hsiRNA-loaded exosomes. (C) Percent of hsiRNAs in the pellet (black bar) vs in the solution (grey bar) after ultracentrifugation of hsiRNAs in the presence and absence of exosomes indicates that ~30% of hsiRNAs are associated with exosomes only in the presence of exosomes (n=3, standard deviation shown).

In order to explore if incorporation of hydrophobic modifications into siRNAs can be used to promote exosome loading, hydrophobically modified siRNAs (hsiRNAs) were used, as described by Byrne et al. *Novel hydrophobically modified asymmetric RNAi compounds (sd-rxRNA) demonstrate robust efficacy in the eye*. J. Ocul. Pharmacol. Ther. 29, 855-64 (2013). The hsiRNAs are asymmetric compounds, with a short duplex region (15 base-pairs) and a single-stranded fully phosphorothioated tail. All pyrimidines were modified with 2'-fluoro and 2'-O-methyl modifications and the 3' end of the passenger strand was conjugated to Teg-Cholesterol (FIG. 10A). The cholesterol enables quick membrane association, while the single-stranded phosphorothioated tail is essential for cellular internalization by a mechanism similar to that used by conventional antisense oligonucleotides (data not shown).

To silence Huntingtin (HTT) expression, hsiRNA HTT10150, targeting position 10150 of the HTT mRNA sequence, was used. Sequences and chemical modification patterns of compounds used in this study are described in Table 2, below.

approximately a 4 nm$^2$ footprint (Watson et al. *Molecular Structure of Nucleic Acids. A Structure for Deoxyribose Nucleic Acid*, Nature 171, 737-738 (1953)), then 1000 hsiRNA per exosome will occupy ~8% of the surface area of an exosome.

TABLE 2

Hydrophobic modification patterns of exemplary siRNA (Table discloses SEQ ID NOS 1-6, respectively, in order of appearance)

| Gene | Compound Name | Compound Type | Strand | Sequence 5'-3' | Conjugate 5' | Conjugate 3' |
|---|---|---|---|---|---|---|
| Non Targeting Control | NTC | hsiRNA | s | mA.mC.A.A.A.mU.A.mC.G.A.mU#mU#mA | Cy3 | Teg-Cholesterol |
| | | | as | PmU.A.A.fU.fC.G.fU.A.fU.fU.fU.GU#mC#A#A#mU #mC#A | | |
| Huntingtin | HTT | SIRNA | s | mC.mA.G.mU.A.A.A.G.A.G.A.mU.mU#mA#mA1 | Cy3 | |
| | | | as | PmU.fU.A.A.fU.fC.fU.fC.fU.fU.fU.A.fC.fU#G# A#fU#A#TU#A | | |
| Huntingtin | HTT10150 | hsiRNA | s | mC.mA.G.mU.A.A.A.G.A.G.A.mU.mU#mA#mA1 | Cy3 | Teg-Cholesterol |
| | | | as | PmU.fU.A.A.fU.fC.fU.fC.fU.fU.fU.A.fC.fU#G# A#fU#A#fU#A | | |

Figure 10B:
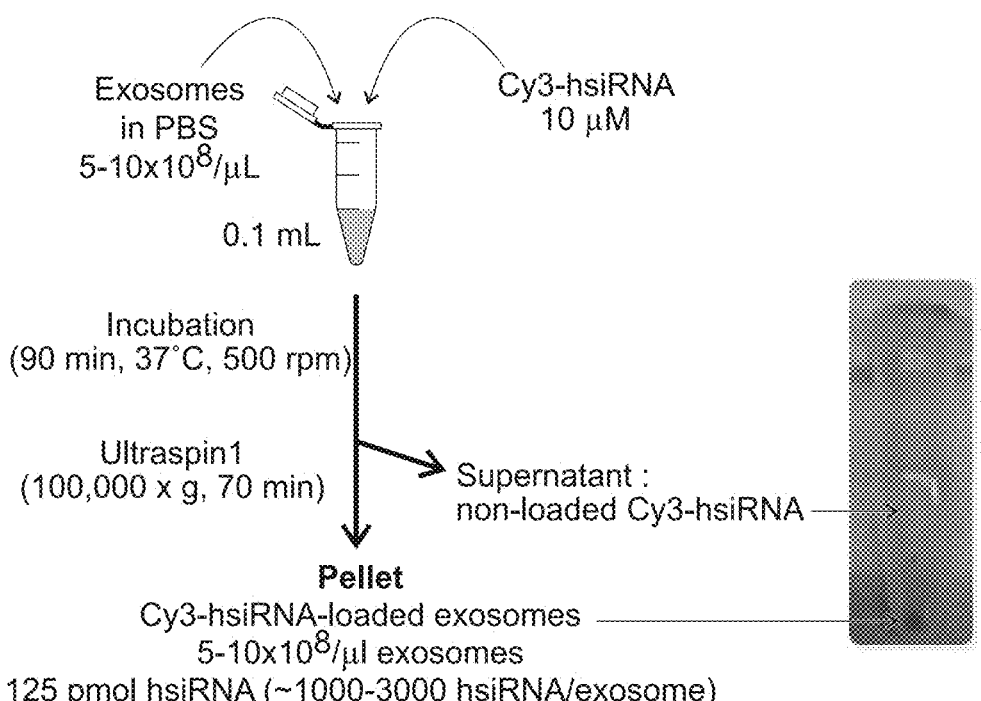
Figure 10C:
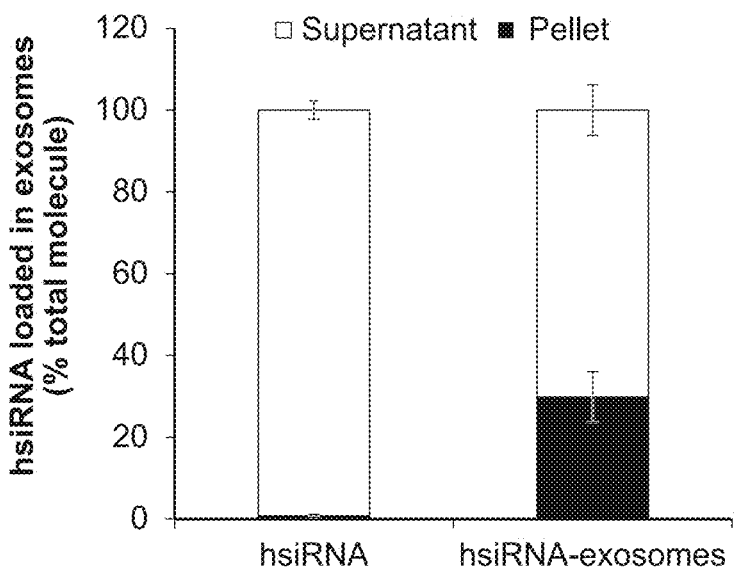
Figures 11A, 11B, 11C:
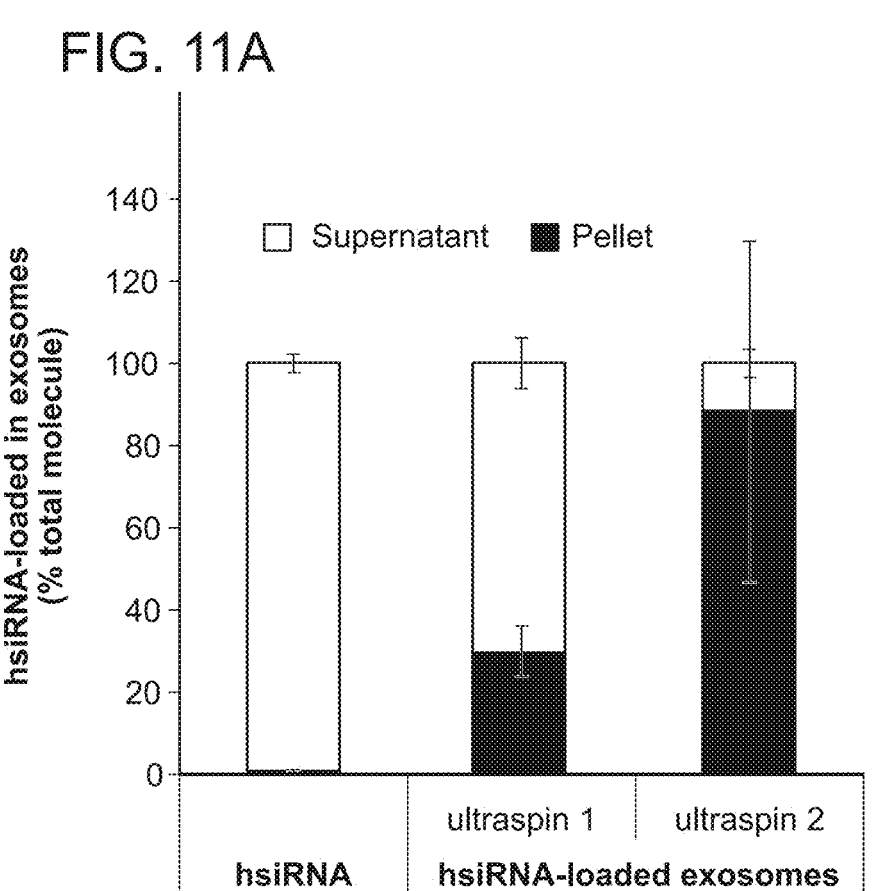
FIG. 11A-C. Cholesterol promotes efficient loading and interaction of hsiRNA into exosomes. (A) Cy3-HTT10150-loaded exosome fluorescence was measured by spectrophotometer. After ultracentrifugation 1, approximately 20% of hsiRNA are associated with the exosomes (black), while non formulated hsiRNA do not pellet. After ultraspin 2, majority of hsiRNA remains associated with the exosomes (n=3 replicates; mean±S.D.). (B) Representative pictures of ultracentrifuged non-formulated hsiRNA (left tube) or hsiRNA-loaded exosomes (right tube). (C) Representative pictures of ultracentrifuged siRNA-loaded exosomes (left tube) or corresponding hsiRNA-loaded exosomes (right tube).

The loading of exosomes with hsiRNA was performed by the co-incubation of Cy3-HTT10150 (10 μM) with freshly purified U87-derived exosomes for 90 min at 37° C. hsiRNAs-loaded exosomes were separated from non-bound hsiRNAs by ultracentrifugation (FIG. 10B). Ultracentrifugation of exosomes after incubation with CY3-hsiRNA resulted in production of a bright red pellet (FIG. 10B) with some of the fluorescence remaining in solution. The ultracentrifugation of hsiRNA in PBS did not produce any pellet indicating that pelleted hsiRNAs are indeed associated with exosomes (FIG. 10C). Approximately 30% of hsiRNA were associated with exosomes based on comparison of fluorescence present in the pellet vs solution (FIG. 10C. To evaluate stability of the hsiRNA-loaded exosomes, the pellet was suspended in PBS followed by a second ultracentrifugation. About 80% of Cy3 fluorescence remained in the pellet confirming a stable interaction between hsiRNA and exosomes (11A). FIG. 11B shows representative pictures of ultracentrifuged non-formulated hsiRNA (left tube) or hsiRNA-loaded exosomes (right tube). In addition, the presence of the hydrophobic modification (e.g., cholesterol) was essential for the association of siRNA and exosomes, as non-cholesterol conjugated hsiRNA, of the same chemical composition, was not pelleted with exosomes (FIG. 11C). Substitution of cholesterol to other hydrophobic modifications can affect the efficiency of loading (data not shown).

In summary, co-incubation of hsiRNAs and exosomes resulted in efficient loading of hsiRNA into exosomes, and the observed loading was dependent on the presence of the hydrophobic modification, (e.g., cholesterol).

Figures 13A, 13B, 13C:
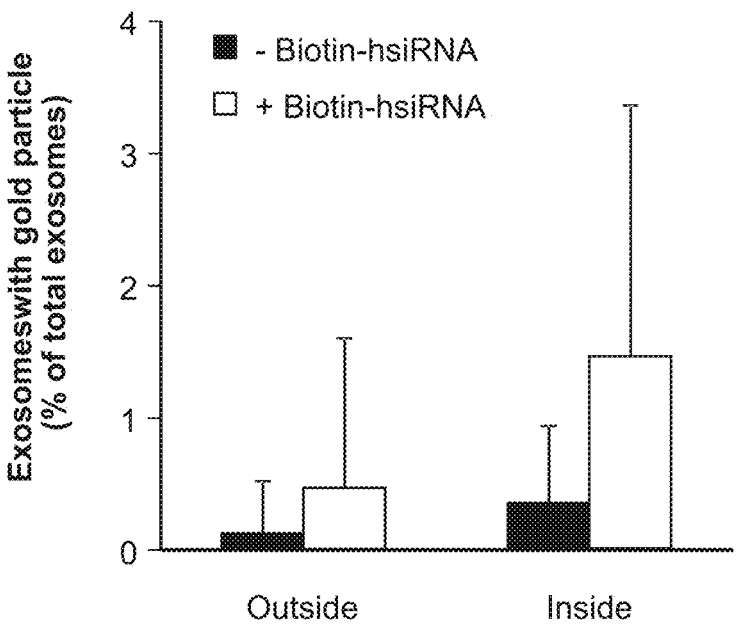
FIG. 13A-C. Electron microscopy validates the presence of hsiRNA at the surface and in the lumen of exosomes. Exosomes were incubated with biotinylated HTT10150 hsiRNA and purified as described herein. Electron microscopy was performed in the absence (data not shown) or presence (A) of streptavidin immunogold particles on sample not treated (A) or treated with 0.1% saponin (B). (C) Quantification of gold particles inside or outside of exosomes.

Example 9: Characterization of hsiRNA-Loaded Exosomes hsiRNA loading was evaluated to see if it interfered with physical properties of the exosomes. First, measurement of the fluorescence intensity in relation to particle numbers (Nanosight), revealed an estimate of about ~1000-3000 hsiRNA per exosome (FIG. 12A). To estimate the surface area of exosome occupied by hsiRNA, 130 nm was used as an average diameter and ~53100 nm$^2$ as surface area of an exosome. If the diameter of the RNA duplex is 2 nm with Next, the impact of hsiRNA loading on particle size and charge was evaluated (FIG. 12). Nanoparticle tracking analysis of unloaded and loaded exosomes indicates similar particle size distribution (FIGS. 12A and C), and electron microscopy showed similar shapes indicating that hsiRNA association did not interfere with exosome integrity (FIG. 12B). A slight decrease in a Zeta potential of the hsiRNA-loaded exosomes, compared to unloaded exosomes, (from −13 to −30 mV) is consistent with additional, negatively charged hsiRNA presence on the surface of the exosomes (FIG. 12A). To evaluate localization of hsiRNA on exosomes, exosomes were loaded with a biotinylated HTT10150, labeled with streptavidin-gold and analyzed by electron microscopy. hsiRNA were detected both at the surface and in the lumen of exosomes (FIG. 13A-C). Taken together, these data suggest that exosomes loaded with hsiRNA are not altered in their physical properties and overall integrity.

Example 10: HTT10150-Loaded Exosomes Traffic Efficiently into Primary Cortical Neurons and Induce Potent HTT mRNA Silencing hsiRNA labeled with Cy3 (red) and exosomes labeled with a lipophilic dye PKH67 (green), were added to primary cortical neurons and their uptake was evaluated over time using confocal microscopy (FIG. 14). hsiRNA-loaded exosomes efficiently trafficked into primary neurons with approximately 62% of hsiRNAs co-localizing with exosomes at 24 hours.

Figures 15A, 15B, 15C:
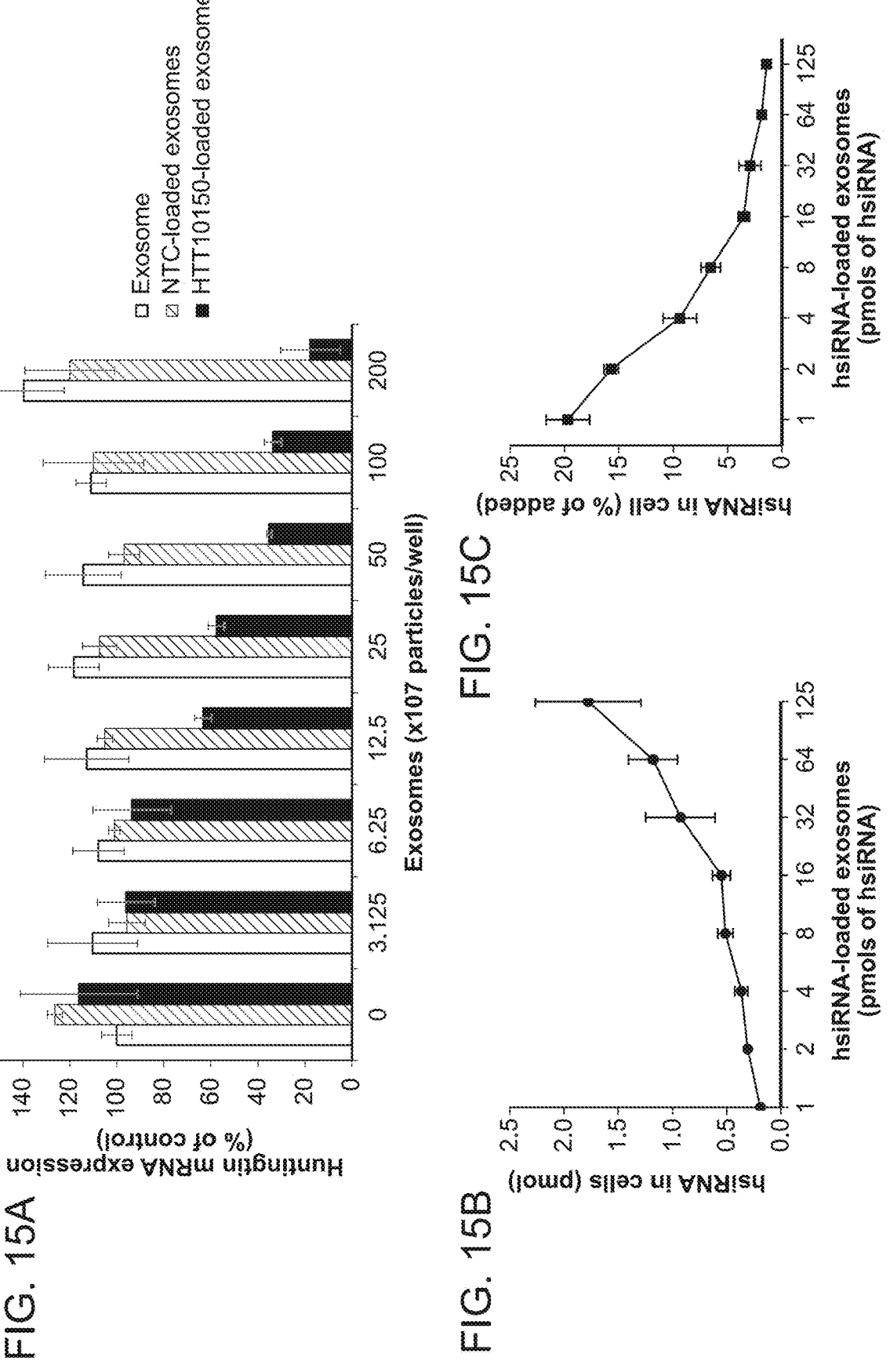
FIG. 15A-C. Concentration dependent silencing of huntingtin mRNA by HTT10150-loaded exosomes in primary cortical neurons. Exosomes were loaded with 20 µM hsiRNA HTT10150 or NTC as described herein. (A) Primary cortical neurons were incubated with non-loaded exosomes (left bar; light grey), NTC-loaded exosomes (middle bar; dark grey) and HTT10150-loaded exosomes (right bar; black) for one week. The level of huntingtin mRNA was measured using QUANTIGENE assay (Affymetrix) at 7 days and normalized to the housekeeping gene, PPIB (cyclophillin B), and presented as percent of untreated control (n=3 replicates, mean±SD). NTC=non-targeting control. (B and C) Primary cortical neurons were incubated with Cy3-hsiRNA-loaded exosomes for 4 days. (B) The level of Cy3 fluorescence was monitored in cell lysate by HPLC (n=3 replicates, mean±SD). (C) The proportion of Cy3 fluorescence detected in cell lysate was calculated among the total fluorescence added on cells.

To assess whether exosome mediated hsiRNA delivery would result in productive gene silencing, mouse primary cortical neurons were treated for 7 days in the presence of unloaded, NTC-loaded and HTT10150-loaded exosomes (FIG. 15A). Dose dependent HTT mRNA silencing was observed upon treatment with HTT10150-loaded exosomes but not controls with an estimated IC$_{50}$ the low nM range. This suggests that exosomes support efficient neuronal delivery and do not interfere with RISC assembly and gene silencing induced by hsiRNA cargo. The HTT mRNA silencing was observed when cells were treated with at least 50×10$^7$ exosomes per well.

Figure 14:
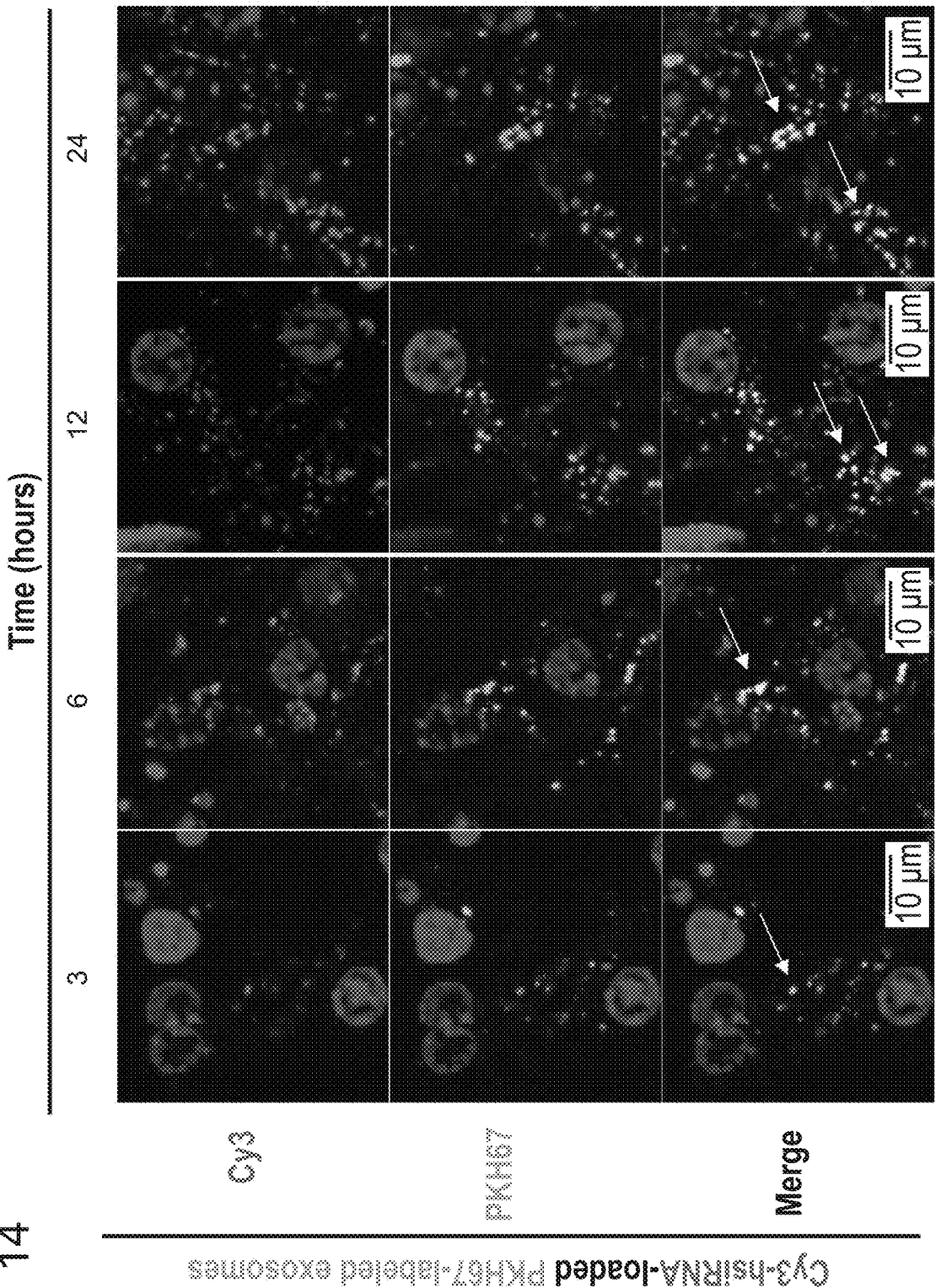
FIG. 14. Efficient internalization of hydrophobic Cy3-hsiRNA-loaded exosomes in primary cortical neurons. Cy3-HTT10150 hsiRNA-loaded exosomes (PKH67 labeled, green) were added to primary cortical neurons, and internalization was followed by imaging on Leica confocal microscope (63×). Nuclei were stained with Hoechst dye (blue). A significant level of co-localization between exosomes and hsiRNA was observed.

As exosome internalization is a relatively slow process and there was a non-linear efficiency of internalization (FIG. 15B), the fraction of therapeutic cargo that was delivered to primary neurons after 4 days was estimated by tracking the absolute fluorescence associated with the cells (FIG. 15B). There was a higher fraction of exosomes (19% of exosomes) internalized by the cells at low hsiRNA concentrations than at high concentration (1.4% of exosomes) (FIG. 15C). This supports the notion that neurons have a limited capacity to traffic exosomes, consistent with previously observed slow uptake kinetics (FIG. 14). Slow and saturatable trafficking of exosomes in neurons might be an advantage for in vivo delivery and promote wide distribution of formulated oligonucleotides through the brain.

As observed by electron microscopy, hsiRNA are detected both in the lumen and at the surface of exosomes. The hsiRNA-loaded exosomes complex seems to be stable during preparation, and the presence of hsiRNA did not interfere with the physical (size, charge, appearance) and functional (trafficking, brain distribution) properties of the exosomes (FIGS. 12 and 14). Simple co-incubation of hsiRNA and exosomes results in robust and highly reproducible loading of exosomes, independently of the sequence of compounds used. This methodology can be easily applied to loading of other classes of therapeutic oligonucleotides, including miRNA, antisense, antagomirs, or aptamers, as long as oligonucleotides are stable and hydrophobically modified. The simplicity of the protocol makes it attractive for the use of exosomes as delivery vehicles for oligonucleotide therapeutics.

Figures 16A, 16B:
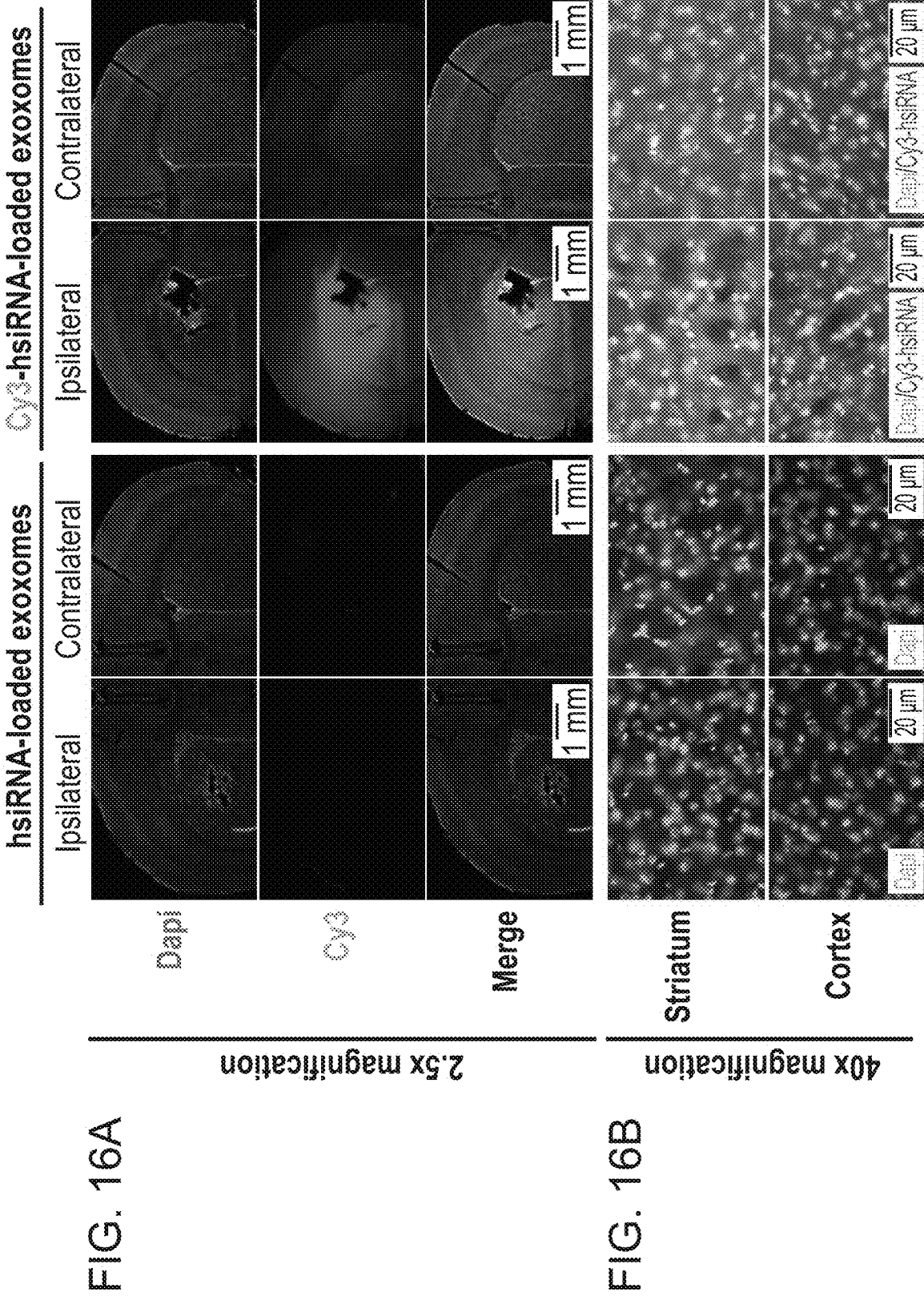
FIGS. 16A and B. Bilateral distribution of Cy3-hsiRNA-loaded exosomes upon unilateral brain infusion. hsiRNA-loaded exosomes or Cy3-hsiRNA-loaded exosomes (red) were loaded into an ALZET pump and unilaterally infused into the striatum of WT (FVBj) mice. Mice were sacrificed after 7 days. 40 µM coronal sections of the brain were stained with Dapi (cyan) as nuclear marker. (A) Pictures of the striatum and cortex were acquired with Leica DM5500-DFC365FX; 2.5×. Representative pictures are shown (n=2). (B) Magnifications were acquired with Leica DM5500-DFC365FX; 63×. Representative pictures are shown (n=2 per group). Unilateral infusion resulted in bilateral distribution of hsiRNA-loaded exosomes throughout the brain, with Cy3-hsiRNA detectable in striatum and cortex on both sides of the brain.

Example 11: Bilateral Distribution of Cy3-hsiRNA-Loaded Exosomes Upon Unilateral Brain Infusion To monitor the in vivo bio-distribution of hsiRNA delivered by exosomes, Cy3-hsiRNA-loaded exosomes were infused directly into mouse striatum for 7 days (0.5 µg/day). Interestingly, unilateral infusion resulted in bilateral distribution of hsiRNA-loaded exosomes throughout the brain, with Cy3-hsiRNA detectable in striatum and cortex on both sides of the brain (FIG. 16). The brains of animals infused with non-Cy3-labeled hsiRNA-loaded exosomes were used as a normalization control to insure that observed fluorescence was indeed due to distribution of Cy3-hsiRNA rather than an increase in tissue fluorescence. Implantation of the pump induced a similar degree of structural damage at the site of infusion in all treatment groups.

There was a high level of fluorescence visible around the site of administration which might be due in part to a high concentration of exosomes or/and degradation of exosomes followed by local release of non-formulated Cy3-hsiRNA. Higher resolution imaging showed that beyond the immediate injected area there was a uniform distribution of the hsiRNA-loaded exosomes throughout brain tissue (40× magnification, FIG. 16). Confocal fluorescent microscopy of tissues co-stained with NeuN (neuronal marker) showed accumulation of compounds in neurons (FIG. 17).

Figure 17:
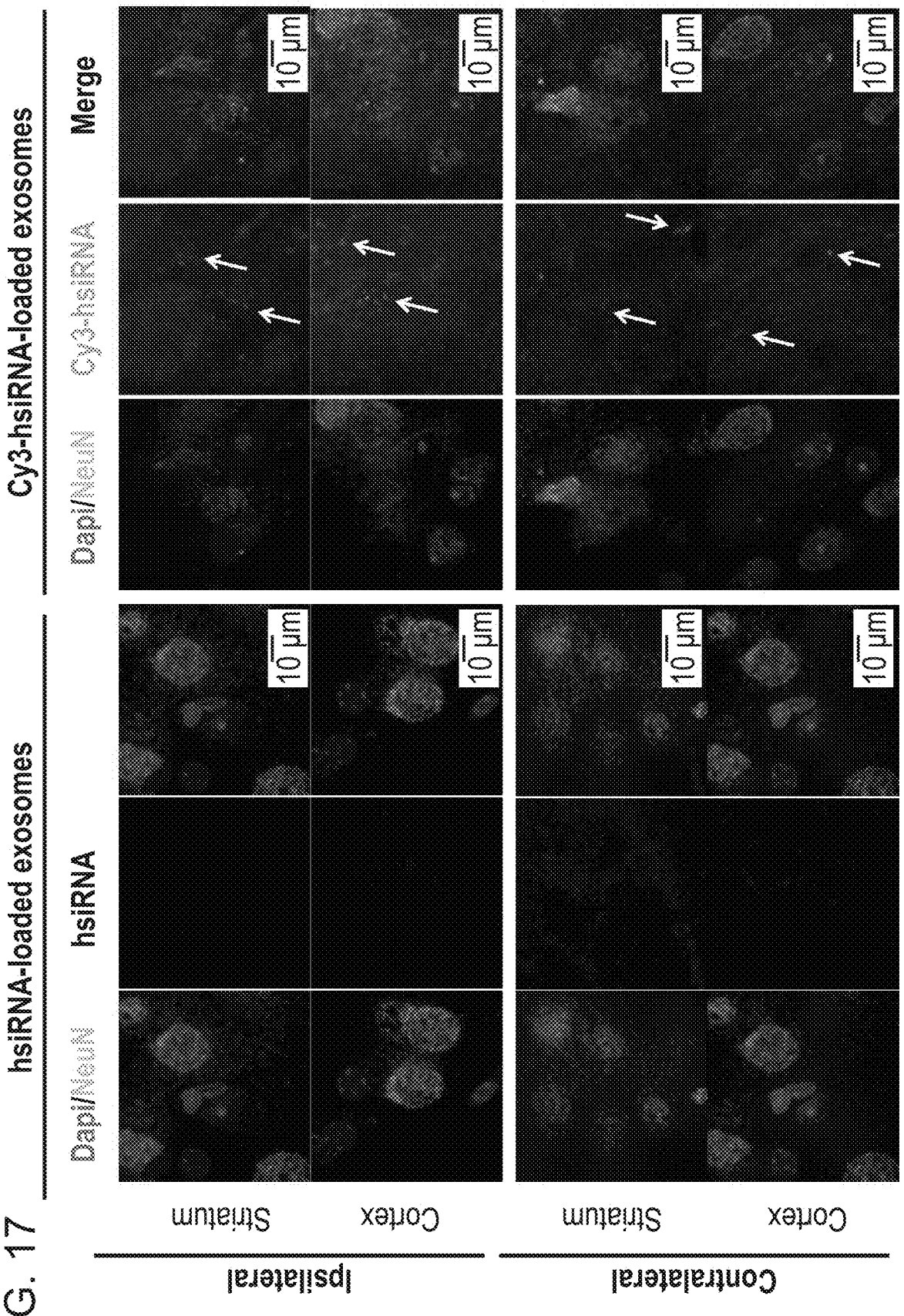
FIG. 17. Bilateral uptake of HTT10150-loaded exosomes in neurons in mouse brain. hsiRNA-loaded exosomes or Cy3-hsiRNA-loaded exosomes (red) were loaded into an ALZET pump and unilaterally infused into the striatum of WT (FVBj) mice. Mice were sacrificed after 7 days. 40 µM coronal sections of the brain were stained with Dapi (blue) as a nuclear marker and NeuN (green) as a neuron marker. Pictures of the striatum were acquired with Zeiss confocal microscope; 63× oil objective. Representative pictures are shown (n=2). Confocal fluorescent microscopy of tissues co-stained with NeuN (neuronal marker) showed accumulation of compounds in neurons Arrows=accumulation of Cy3-hsiRNA in neurons.

The intra-striatal infusion of hsiRNA-loaded exosomes resulted in bilateral compound distribution (FIGS. 16 and 17). Formulation of hsiRNA into exosomes is essential for efficacy, as infusion of the same dose of non-formulated oligonucleotides did not affect huntingtin mRNA expression (FIG. 16). These data support the notion that exosomes promote wide tissue distribution and neuronal uptake of their cargo.

Figures 18A, 18B:
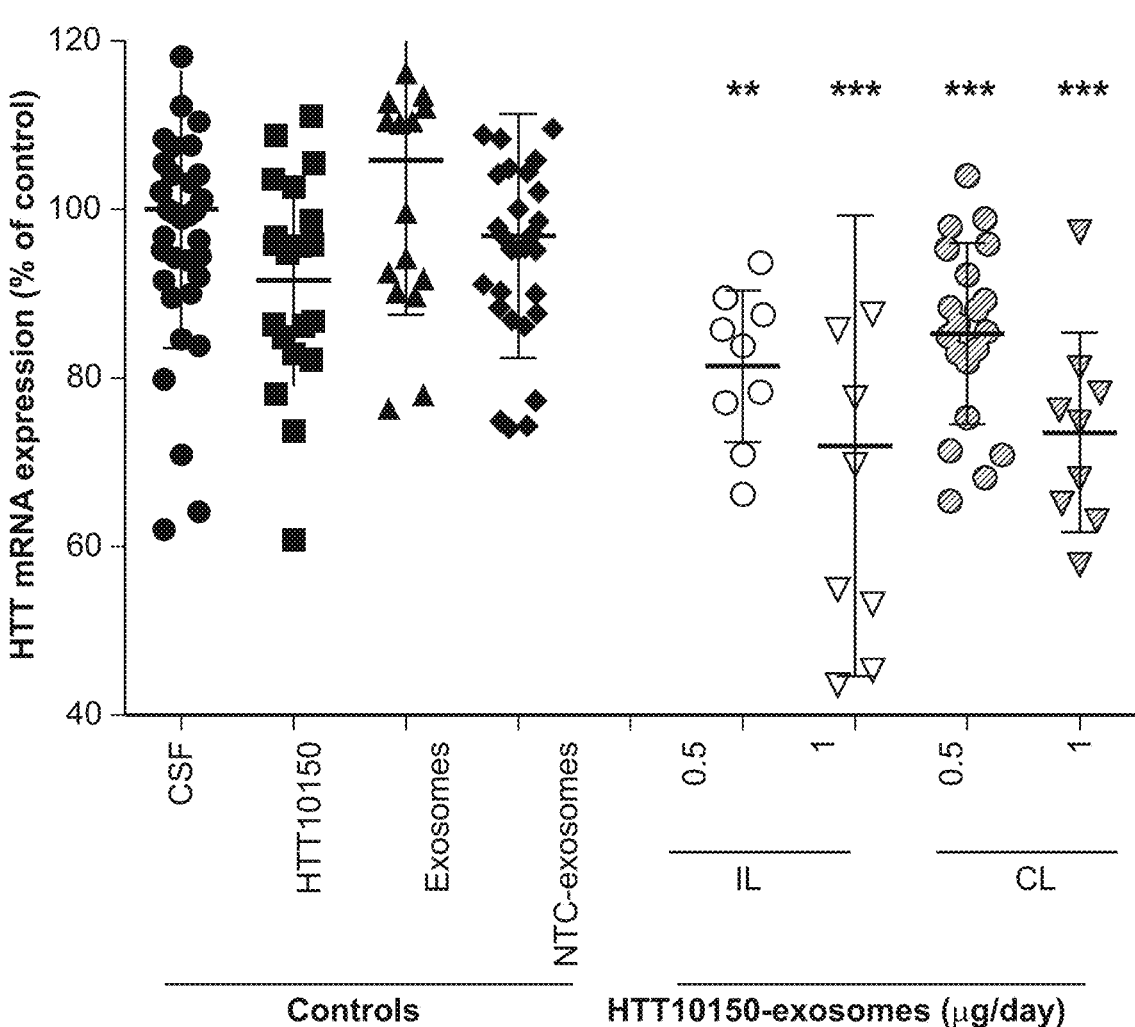
FIGS. 18A and B. hsiRNA-loaded exosomes induce bilateral HTT mRNA silencing in vivo in mouse brain. (A) ALZET pumps with PBS, aCSF, unloaded exosomes, HTT10150 (1 µg/day), NTC-loaded exosomes and HTT10150-loaded exosomes (2-4×1010 particle/day—hsiRNA 0.5 and 1 µg/day for 7 days) (n=10 for each group) were unilaterally implanted into the right striatum of WT (FVBNj) mice. Mice were sacrificed after 7 days. Brains were sliced into 300 µm sections and three 2 mm punch biopsies of both striatum were collected. The level of huntingtin mRNA was measured using QUANTIGENE assay (Affymetrix), normalized to housekeeping gene, PPIB (cyclophillin B), and presented as a percent of untreated control (n=30 punches, mean±SD). P<0.05, *P<0.01, one-way ANOVA test, Bonferroni correction. aCSF=Artificial CerebroSpinal Fluid; CL=Contralateral; IL=Ipsilateral. (B) Table showing descriptive statistics.

Example 12: HsiRNA-Loaded Exosomes Induce Bilateral HTT mRNA Silencing In Vivo in Mouse Brain It was next evaluated whether observed bilateral distribution would result in HTT mRNA silencing. HTT10150-loaded exosomes with corresponding controls were unilaterally infused into the striatum of wild type mice (n=10) by ALZET pump for 7 days. Compared to PBS injected mice, HTT10150-loaded exosomes showed a dose dependent and statistically significant decrease of HTT mRNA at both concentrations used. More importantly, the silencing was bilateral, consistent with distribution pattern (FIG. 18A). One way ANOVA with Duns' multiple comparison correction showed that the observed silencing was highly significant in all mice treated with HTT10150-loaded exosomes but not in the control groups treated with PBS or aCSF, non-formulated HTT10150 (1 µg/day) and unloaded exosomes (FIG. 18B). The fact that unformulated HTT10150 did not induce HTT silencing, indicates that the hsiRNA10150 loading into exosomes was essential for both functional neuronal uptake and brain distribution.

The intra-striatal infusion of hsiRNA-loaded exosomes resulted in statistically significant huntingtin silencing (FIG. 18). The ability of hsiRNA-loaded exosomes to silence HTT mRNA in both treated and non-treated sides of the brain was indicative of exosomes mediated efficient spread of compounds through the brain and highlights the advantage and therapeutic relevance of exosomes as a delivery vehicle in the CNS.

The Examples above demonstrate that ipsilaterally introduced hsiRNA formulated exosomes induce HTT mRNA silencing on both sides of the brain at exceptionally low concentrations. 3-7 µg of hsiRNA (infused over a week) was sufficient to induce ~35% bilateral silencing. The unexpected and surprising potency of the hsiRNA loaded exosomes shows that that their utilization can enable more potent neuronal uptake routes.

Example 13: HsiRNA-Loaded Exosomes Impact on Neuronal Integrity and Immune Response Nonspecific effects, including immuno-stimulation and cytotoxicity, represent concerns of using exosomes as a therapeutic delivery vehicle. To evaluate the impact of hsiRNA-exosome administration, the level of microglia activation and cell death were monitored. The morphology of microglia cells, which rapidly transform from a resting to an active state upon activation was assessed by Iba1 staining, a marker of neuroinflammation whose expression is restricted to microglia and up-regulated upon brain injury (Imai et al., *A novel gene iba1 in the major histocompatibility complex class III region encoding an µF hand protein expressed in a monocytic lineage.*, Biochem. Biophys. Res. Commun. 224, 855-862 (1996). Intense Iba1-positive microglia arbor an enhanced staining intensity, enlarged cell bodies and ramified processes. In addition to 7 day point, the microglia response was evaluated at 6 hours post hsiRNA-loaded exosomes injection (2 µl), as some of the immune response may be transient and might disappear by the 7 day time point.

Figures 19A, 19B:
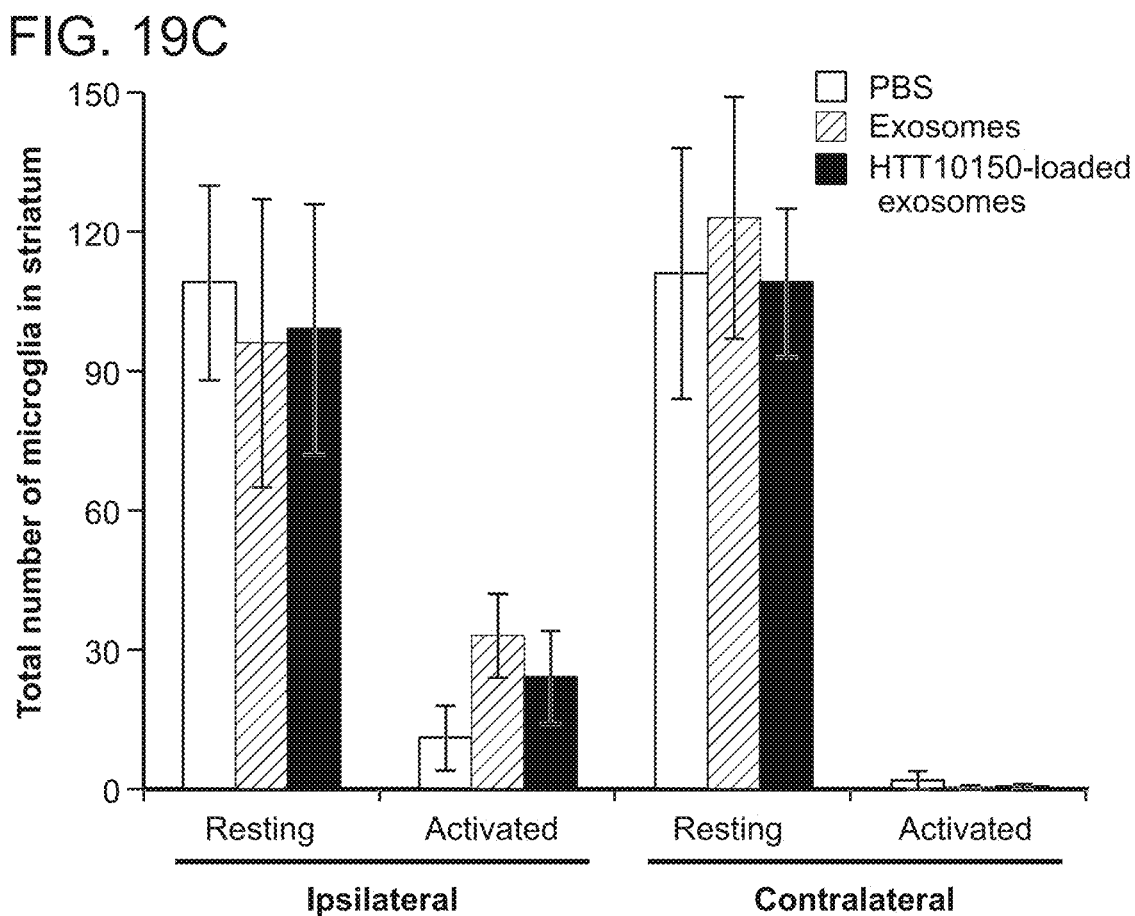
Figure 19D:
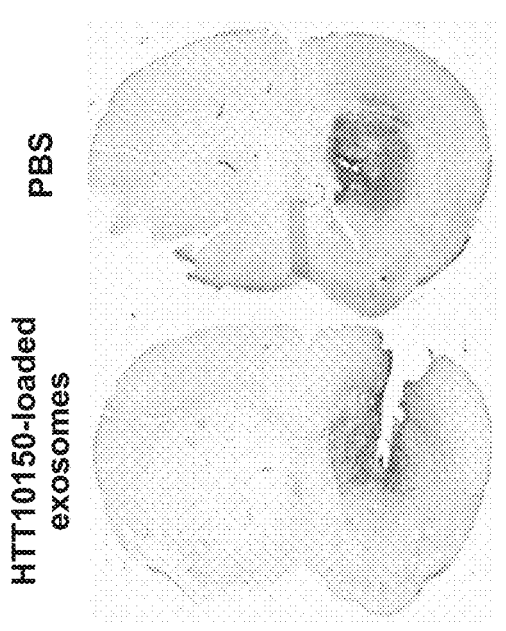
Figure 19E:
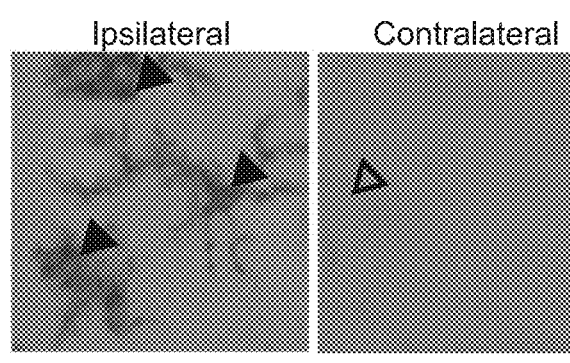
Figure 19F:
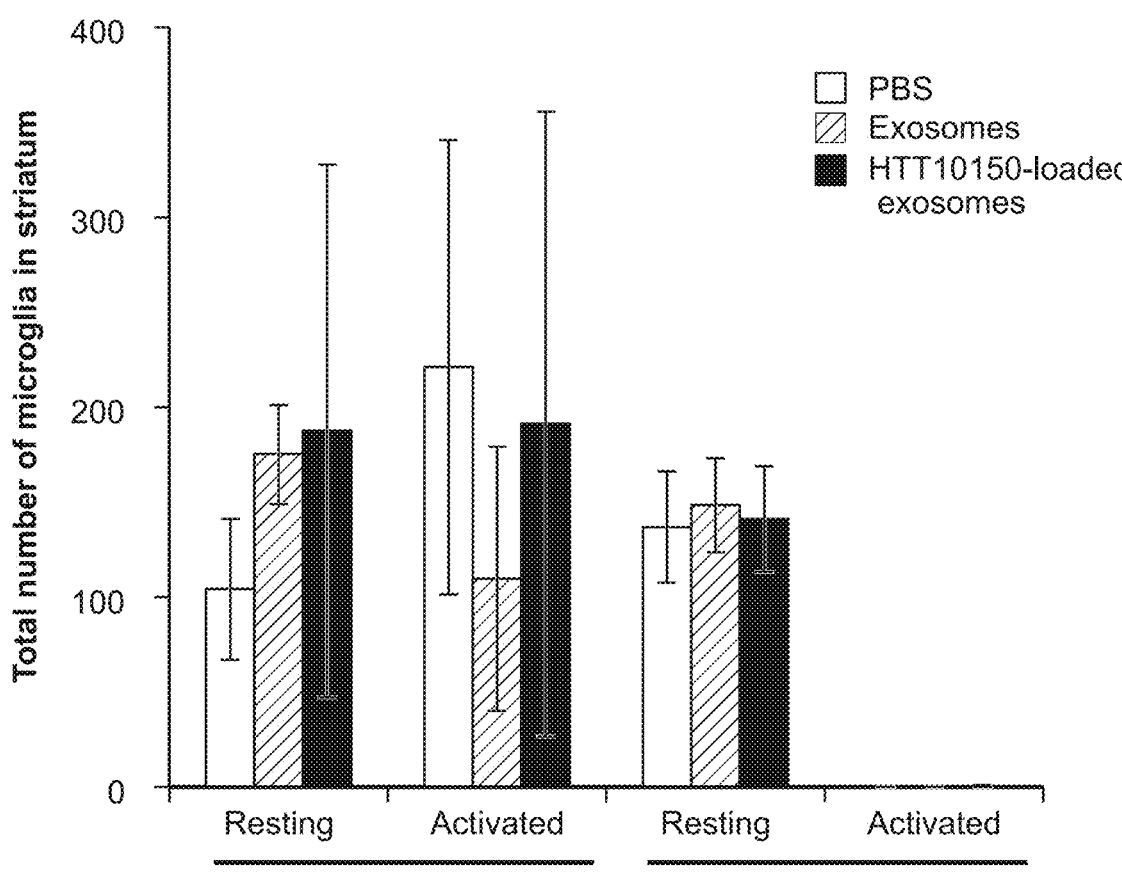
Figures 21A, 21B:
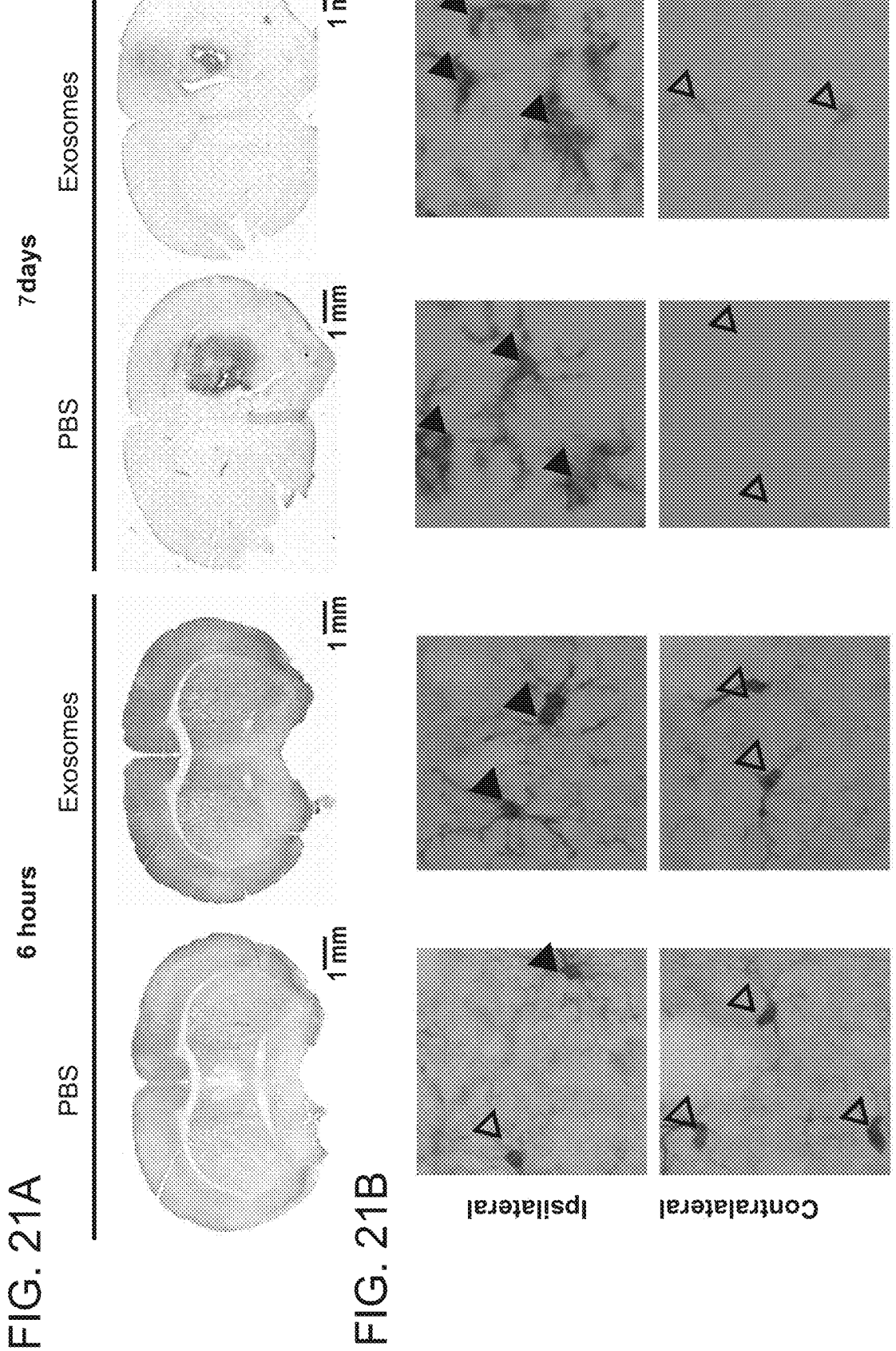
FIGS. 21A and B. Exosomes and hsiRNA-loaded exosomes have no impact on immune response in vivo. PBS, exosomes and hsiRNA-loaded exosomes were unilaterally injected into striatum or loaded into Alzet pump and unilaterally infused into the striatum of WT (FVBj) mice (n=5 per group). Mice were respectively sacrificed after 6 hours or 7 days. 40 µm coronal sections of the brain were stained with Iba1 antibody to evaluate cell death. (A) Scans of brain section were acquired using the Nikon CoolScan5000 slide scanner. (B) Magnifications of the ipsilateral and contralateral striatum were acquired with Leica DM5500-DFC365FX; 63×. Representative pictures are shown. White arrowhead=resting microglia; Black arrowhead=Actived microglia. NTC=Non Targeting Control.

Mice brain sections were analyzed either 6 h after direct striatal injection or 7 days after pump infusion of PBS, exosomes alone, and HTT10150-exosomes. The changes in histopathology and morphology of microglia staining were comparable between mice injected with PBS, or exposed to exosomes alone or HTT10150-loaded exosomes for 6 hours (FIGS. 19A and C and FIG. 21). Visual evaluation of treated and untreated brains did not show any major inflammatory events (FIG. 19B). Although more precise quantification of resting vs activated microglia demonstrated that intracranial injection with PBS induced a slight higher level of microglia activation in the ipsilateral side of the brain, but not in the contralateral side. The number of activated microglia was further increased in exosomes and hsiRNA-loaded exosomes samples suggesting a minor neuro-inflammation enhanced by the presence of injected exosomes (FIG. 19C). Following 7 days infusion, an increase of activated microglia cells was observed in the ipsilateral side of brain injected with PBS, non-loaded exosomes or HTT10150-loaded exosomes. No actived microglia were detected in the contralateral side of the brain suggesting an inflammatory response most probably due to the implantation of the pump (FIGS. 19 D, E, and F and FIG. 21).

Figure 20A:
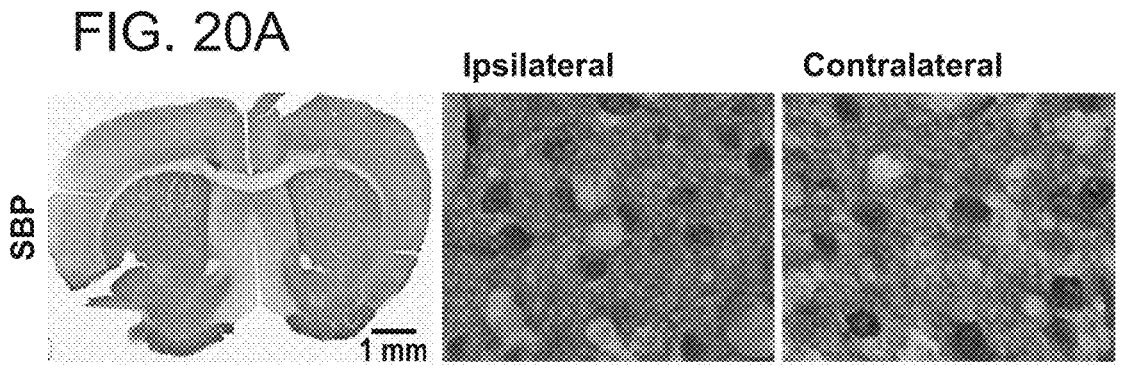
FIG. 20A-C. Exosomes and hsiRNA-loaded exosomes have no impact on cell viability in vivo. HTT10150 loaded exosomes were unilaterally injected into the striatum of WT (FVBj) mice. Mice were perfused after 7 days and brains were sliced into 40 µm sections. (A and B) Sections were stained with DARPP32 antibody. (C) Quantification of DARPP32 labeled cells did not show any change in the number of cells on the injected vs non-injected side.
Figure 20B:
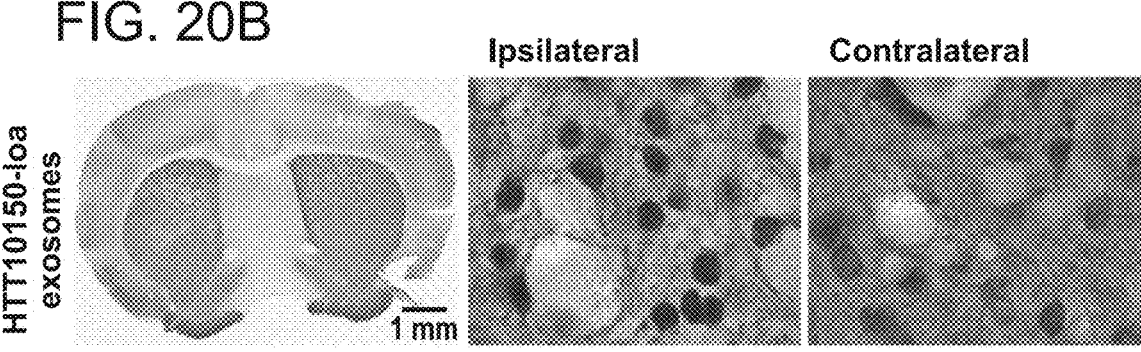
Figure 20C:
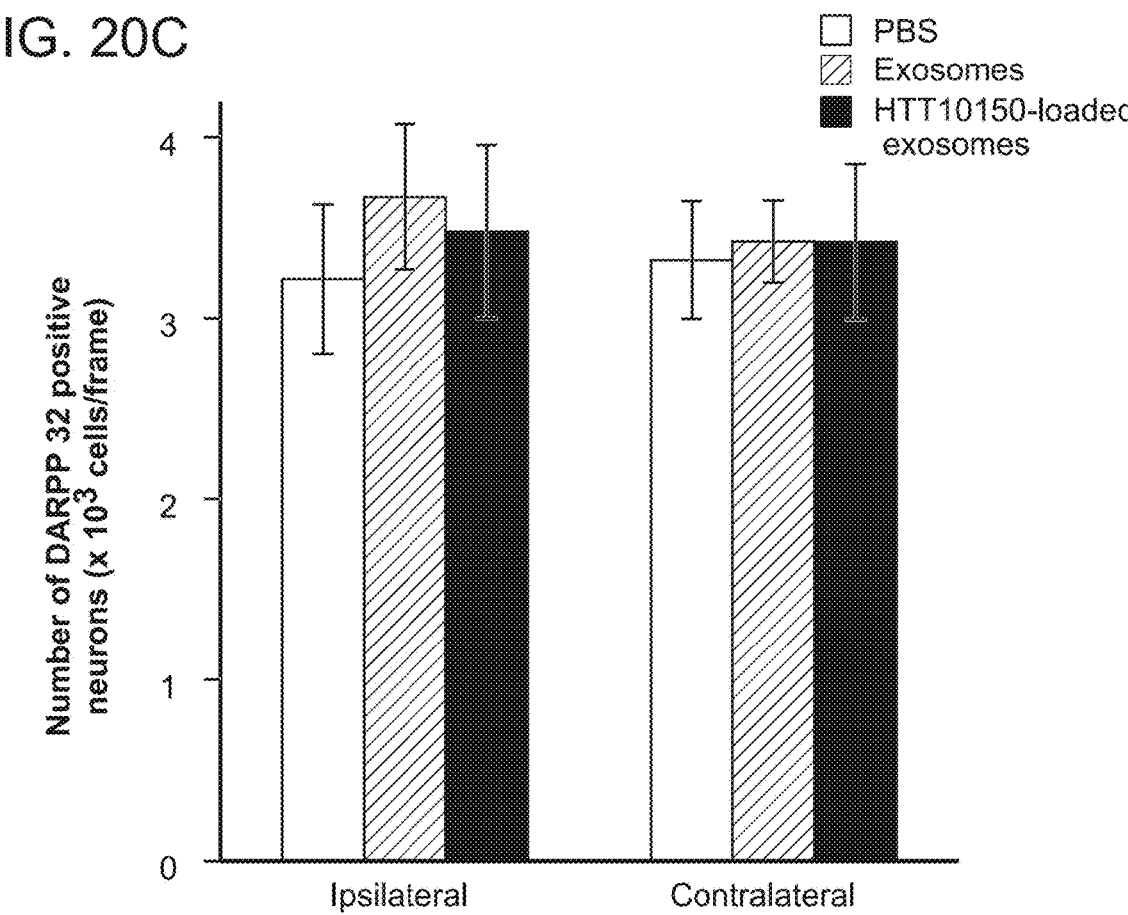

Finally, in order to assess the cytotoxicity of hsiRNA-exosomes administration, PBS, exosomes alone and HTT10150-exosomes were infused into murine striatum for 7 days. The impact on neuronal integrity was monitored by immunohistochemistry for DARPP32 which is expressed in the majority of striatal neurons known as medium spiny neurons. DARPP32 staining was performed on brain coronal sections. Qualitative and quantitative analysis of the coronal sections of each brain showed no apparent change in neuronal density on the sides ipsilateral and contralateral to the injections, (FIG. 20A-C).

The foregoing experiments describe a simple and robust method to efficiently load exosomes with therapeutic oligonucleotides. In particular, co-incubation of exosomes with hydrophobically modified siRNAs (hsiRNAs) results in quantitative and efficient association of oligonucleotides with vesicles. Loaded exosomes mediated efficient and non-toxic internalization of hsiRNA and dose-dependent HTT mRNA silencing in primary cortical neurons. Unilateral, intrastriatal infusion of hsiRNA-loaded exosomes showed a bilateral brain distribution in both striatum and cortex and bilateral silencing of HTT mRNA in the striatum. Thus, the Examples presented herein provide a path towards the utilization of exosomes as a native, highly efficient vehicle for delivery of oligonucleotide therapeutics.

Materials and Methods

The Examples described herein were performed with, but not limited to, the materials and methods below.

Cell Culture

U87 glioblastoma cells were maintained in DMEM (Cellgro #10-013CV) supplemented with 100 U/ml penicillin streptomycin (Invitrogen #15140) and 10% fetal bovine serum (Gibco #26140) at 37° C. 5% CO2. For purification of exosomes, media from the glioblastoma cultures was treated with DMEM 4× supplemented with 400 U/ml penicillin streptomycin and 40% FBS and ultracentrifuged in 70 ml polycarbonate bottles (Beckman Coulter #355622) overnight at 100,000×g, 4° C. using a Type 45 Ti rotor (Beckman Coulter #339160) and filtered in 0.2 μm filter bottle.

Preparation of Primary Cortical Neurons

Primary cortical neurons were isolated from E15.5 mouse embryos of WT (FVBNj) mice. Pregnant females were anesthetized by IP injection of Avertin (250 mg/kg weight) followed by cervical dislocation. Embryos were removed and transferred into ice-cold DMEM/F12 medium (Invitrogen #11320). Brains were removed and meninges were carefully detached. Cortices were isolated and transferred into pre-warmed Papain solution for 25 minutes at 37° C.

and 5% CO2 to dissolve tissue. Papain solution was prepared by dissolving Papain (Worthington #54N15251) in 2 mL Hibernate E (Brainbits #HE) and 1 mL EBSS (Worthington #LK003188). Separately, DNase (Worthington #54M15168) was re-suspended in 0.5 mL Hibernate E. The final Papain solution contained 0.25 mL of re-suspended DNase mixed with re-suspended Papain. After the 25 minute incubation, Papain solution was removed and 1 ml NbActiv4 (Brainbits #Nb4-500) supplemented with 2.5% FBS was added to the tissue. Cells were then dissociated by trituration with a fire polished, glass Pasteur pipet. Neurons were counted and diluted at $1×10^6$ cells/ml. For live-cell imaging studies, $2×10^5$ cells were plated in glass bottom dishes pre-coated with poly-L-lysine (Sigma #P4707). For silencing assays, $1×10^5$ neurons per well were plated on poly-L-lysine pre-coated 96-well plates (BD BIOCOAT #356515). After overnight incubation at 37° C. and 5% CO2 an equal volume of NbActiv4 supplemented with anti-mitotics, 0.484 μl/ml of 5'UtP (Sigma #U6625) and 0.2402 μl/ml of 5'FdU (Sigma #F3503), was added to prevent the growth of non-neuronal cells. Half of the volume of media was replaced every 48 hours (with new NbActiv4 with anti-mitotics) until the experiments were performed.

Purification and Characterization of Exosomes

Exosomes were purified from U87 glioblastoma cells as described (Tetta et al., *Extracellular vesicles as an emerging mechanism of cell-to-cell communication.*, Endocrine 44, 11-9 (2013)) (FIG. 9A). Conditioned culture medium containing exosomes was harvested and centrifuged at 300×g for 10 min. The supernatant was then centrifuged at 10,000× g, 4° C. for 30 min and filtered in a 0.2 μm filter bottle. Medium was centrifuged in 70 ml polycarbonate bottles for at least 70 min at 100,000×g, 4° C. using a Type 45 Ti rotor. Pellets were resuspended in 1 ml PBS, and ultracentrifuged for 1 h at 100,000×g, 4° C. in a tabletop ultracentrifuge using a TLA-110 rotor (Beckman Coulter #366730). Pellets were resuspended in PBS for further experiments. For each sample, the concentration and sizes of particles were identified by monitoring the rate of Brownian motion using the NanoSight NS300 system (Malvern) calibrated based on manufacturer's protocol. Samples were diluted at room temperature in 1 ml PBS and monitored in duplicate for 30s with manual shutter and gain adjustments. The recorded videos were analyzed with a Nanoparticle Tracking Analysis (NTA) software. The particles' electronegativity was monitored using the Zetasizer Nano NS (Malvern). Samples were diluted in 1 ml H20 and the zeta potential was monitored in the universal glass cuvette Dip Cell kit (Malvern #ZEN1002).

Loading of Exosomes with Hydrophobic siRNA (hsiRNA) and Fluorescent Labeling

Exosomes were loaded with indicated concentration of hsiRNA in PBS by shaking at 500 rpm, 37° C. for 1 h 30 min. Exosomes were washed from unloaded hsiRNA by ultracentrifugation for 1 h at 100,000 g, 4° C. in a tabletop ultracentrifuge using a TLA-110 rotor (FIG. 10). For in vitro uptake experiments, pellets were resuspended in PBS; for in vitro knock down analysis, pellets were resuspended directly in cell medium. Following the ultracentrifugation, the loading efficiency was estimated by monitoring the Cy3-fluorescence of the supernatant and the pellet resuspended in PBS. Samples were transferred in Costar UV-transparent flat bottom 96-well plate (Corning #3635) and fluorescence was measured using the Infinite® M1000 Pro microplate spectrophotometer (Tecan) with excitation and emission wavelengths respectively at 547 nm and 570 nm. For monitoring uptake, of hsiRNA, exosomes were fluorescently labeled with PKH67 dye (Sigma #PKH67GL-1KT). Briefly, 1 μl of PKH67, at a final concentration of 10 UM, was added to exosomes, diluted in 100 μl PBS, and incubated for 30 min at 37° C. Free dye was washed from labeled exosomes using the Exosome Spin Column (MW3000) (Life Technologies #4484449) as indicated by the manufacturer's protocol.

mRNA Quantification mRNA was quantified using the QuantiGene 2.0 Assay (Affymetrix #QS0011). Cells were lysed in 250 μL diluted lysis mixture (Affymetrix #13228) supplemented with 0.167 μg/μL proteinase K (Affymetrix #QS0103) for 30 minutes at 55° C. Cell lysates were mixed thoroughly and 40 μl (~16000 cells) of lysate were added to the capture plate along with 40 μl additional diluted lysis mixture without proteinase K. Probe sets were diluted as specified in the Affymetrix protocol. 20 μl of mouse HTT or PPIB probe set (Affymetrix #SB-14150, #SB-10002) was added for a final volume of 100 μl.

Tissues were lysed in 300 μl of homogenizing buffer (Affymetrix #10642), supplemented with 2 μg/μl proteinase K per 5 mg tissue punch, and homogenized in 96-well plate format on the QIAGEN TissueLyser II. 40 μl were added to the capture plate and mixed with 60 μl of either HTT or PPIB diluted probe sets (Affymetrix #SB-14150, #SB-10002) for a final volume of 100 μl, as specified by the manufacturer's protocol. Signal was amplified according to the Affymetrix protocol. Luminescence was detected on either the Veritas (Promega) or the Infinite® M1000 Pro (Tecan) microplate luminometer.

Live Cell Staining

For live cell uptake monitoring, cells were plated at a density of $2\times10^5$ cells per 35 mm glass-bottom dish. Prior to imaging, cell nuclei were stained in cell medium using the NUCBLUE Live READYPROBE as indicated by the manufacturer (Life Technologies #R37605). Imaging was performed in phenol red free Hibernate E (Brainbits #HE-Pr). Cells were treated with 0.5 μM of Cy3-labeled hsiRNA, and live cell imaging was performed over time.

Brain Sections Immunohistochemistry Staining

In vivo cytotoxicity and microglia activation were monitored by respectively staining for immunoreactive DARPP32 and Iba1 proteins. Perfused brains were sliced into 40 μm sections in ice cold PBS with the Leica Vibratome 2000T (Leica Biosystems) through the striatum. Immunohistochemistry was performed on every 6th section at room temperature unless stated. Iba1-reactive cells were stained by incubating sections in blocking solution (5% normal goat serum and 1% bovine serum albumin) with 0.2% TRITON-X-100 and 0.03% hydrogen peroxide in PBS for one hour. Sections were washed with PBS, and incubated with anti-Iba1 (polyclonal rabbit anti-mouse/human/rat; dilution: 1:1,000 in blocking solution) (Wako #019-19741) overnight at 4° C. Sections were washed with PBS, and incubated in biotinylated secondary antibody (1:200 goat anti-rabbit; Vector Laboratories) in PBS for 10 minutes. After washing with PBS, the Vectastain ABC Kit (Vector) was used, followed by a final PBS wash. The reaction was visualized by 3,3'-diaminobenzidine (DAB) with the Metal Enhanced DAB Substrate Kit (Pierce). DARPP32 immunohistochemistry consisted of a 3 minute wash in 3% hydrogen peroxide, 20 minute wash in 0.2% TritonX-100, and a 4 hour incubation in 1.5% normal goat serum diluted in 1×PBS. Primary DARPP32 antibody (1:10,000 dilution) (Abcam #40801) in 1.5% normal goat serum was added, and sections were incubated at 4° C. overnight. Secondary anti-rabbit antibody, ABC kit, and DAB reagent were used as described above. Following staining, sections were mounted and visualized by light microscopy. Four images were taken at 20× in the striatum of both injected and non-injected sides of each section. The number of DARPP32 positive neurons and activated microglia, detected by morphology of stained cells for Iba1, were quantified using ImageJ. Pictures were acquired with an epifluorescence Leica DM5500-DFC365FX microscope.

Animal Stereotaxic Injections

Animals were deeply anesthetized prior to injection with 1.2% Avertin. For direct injection in the striatum, wild-type (FVBNj) mice received microinjections by stereotactic placement into the right striata (coordinates (relative to bregma) were 1.0 mm anterior, 2.0 mm lateral, and 3.0 mm ventral). For 7 day infusion, ALZET osmotic pumps (#1007D, delivery rate 0.5 μl/hour over 7 days) were pre-filled with 100 μl of sample following manufacturer's instructions and primed overnight at 37° C. in a water bath. For analysis of immunoreative DARPP32 and Iba1 mice received injections or pump infusion (100 μl) of either PBS or artificial cerebrospinal fluid (2 μl per striata, or 100 μl per pump, n=5 mice), $20\text{-}30\times10^8$ particles/day of exosomes alone (2 μl per striata, or 100 μl per pump, n=5 mice), or HTT10150-exosomes (2 μl per striata or 100 μl per pump, n=5 mice), and euthanized 6 hours or 8 days later. For the 7 day infusion study, mice were treated with either PBS or artificial cerebrospinal fluid (100 μl per pump, n=10 mice), 20-30×108 particles/day of exosomes alone (100 μl per pump, n=10 mice), 1 μg/day HTT10150 alone (100 μl per pump, n=10 mice) and 1 μg/day of NTC siRNA associated with $20\text{-}30\times10^8$ particles/day of exosomes (100 μl per pump, n=10 mice) 0.5 or 1 μg/day of HTT10150 associated with 20-30×108 particles/day of exosomes (100 μl per pump, n=10 mice/treatment group) and euthanized 8 days later. Brains were harvested and sliced into three 300 μm coronal sections. One 2 mm punch was taken from the striatum and cortex from each hemisphere of each section and placed in RNA later (Ambion #AM7020) for 24 hours at 4° C. Each punch was processed as an individual sample for the QuantiGene 2.0 Assay analysis. All animal procedures were approved by the University of Massachusetts Medical School Institutional Animal Care and Use Committee (IACUC, protocol number A-2411).

Confocal Imaging

For the analysis of hsiRNA uptake in vitro, mages were acquired with a Leica DM IRE2 confocal microscope using a 63× oil immersion objective. For the study of distribution in brain, images of labeled sections were acquired with a CSU10B Spinning Disk Confocal System scan head (Solamere Technology Group) mounted on a TE-200E2 inverted microscope (Nikon) with a 60× Plan/APO oil lens and a Coolsnap HQ2 camera (Roper). Images were processed using ImageJ (1.47v) software and the percentage of colocalization was calculated based on Manders Overlap Coefficient using the Manders Coefficients plugin in ImageJ.

Size Exclusion Chromatography

Exosomes from U87 were purified as previously described. 50 μl of cell conditioned medium or 50 μl of exosomes were injected onto BioSep SEC-s4000 column (size exclusion column, pore size 500 Å) on Agilent 1100 HPLC system. Chromatography was conducted with 0.75 ml/min flow rate with PBS as mobile phase. Eluted fractions were monitored at 220 nm with Agilent DAD G1315B absorbance detector.

Anion Exchange Chromatography

Primary cortical neurons, plated at $1\times10^5$ cells/well in 96-well plate, were treated with Cy3-labeled hsiRNA with or without exosome formulation. After 4 days of incubation, both medium, transferred into a new 96 well plate, and cells were lysed in EpiCentre Cell and Tissue Lysis Solution in the presence of proteinase K. SDS from the lysis buffer was precipitated by 3 M KCl and pelleted at 5000 g. Supernatant was injected onto anion exchange Dionex DNAPac P100 column on Agilent 1100 HPLC system. Chromatography was conducted at 1 ml/min flow rate in 50% water, 50% acetonitrile, 25 mM Tris (pH=8.8), 1 mM EDTA, salt gradient 10-100% 800 mM NaclO4. Eluted fractions were detected by Cy3 fluorescence with Agilent FLD1260 G1321B detector.

Electron Microscopy

The samples and grids for electron microscopy were prepared at room temperature unless specified in the method. An equal volume of 4% paraformaldehyde was added to the exosome sample and incubated for 2 h. 3 μl aliquots of exosomes were dropped onto grids and incubated in 2% paraformaldehyde for 20 min. The grids were transferred to a wax strip and washed with 100 μl PBS. The grids were incubated in 50 mM glycine/PBS for 5 min and blocked in 5% BSA/PBS for 10 min in the presence or absence of 0.1% saponin. The grids were washed in 2×PBS and incubated with 6 or 10 nm streptavidin immune-gold particles diluted 1:10-1:20 in 0.5% BSA/PBS for 1 h in the presence or absence of 0.1% saponin. The grids were washed with 3×PBS and incubated in 1% glutaraldehyde for 5 min. Following 8 washes of 2 min each with H20, the grids were incubated for 5 min in uranyl oxalate and in 1% methyl cellulose: 4% uranyl acetate (9:1) for 10 min on ice. Excess liquid was removed with a filter paper and the grids were air dried for 5 to 10 min. Exosomes were examined in a JEOL 1100 transmission electron microscope at 60 kV and. Images were obtained with ATM digital camera.

Statistical Analysis

Data analyses were done using GraphPad Prism 6 version 6.04 software (GraphPad Software Inc.). For determination of IC50s, a curve was fitted using log (inhibitor) vs. response-variable slope (four parameters). The bottom of the curve was set to be no less than zero and the top of the curve was set to be no greater than 100. For each mouse experiment, the level of knockdown at each dose was normalized to the mean of the control group, which was the non-injected side in those mice treated with PBS or artificial CSF. In vivo data were analyzed using the Kruskal-Wallis test (one-way ANOVA) with Bonferroni corrections for multiple comparisons. Differences in all comparisons were considered significant at $P<0.05$.

INCORPORATION BY REFERENCE

The contents of all cited references (including literature references, patents, patent applications, databases and websites) that maybe cited throughout this application are hereby expressly incorporated by reference in their entirety for any purpose, as are the references cited therein. The practice of the present invention will employ, unless otherwise indicated, conventional techniques of immunology, molecular biology and cell biology, which are well known in the art.

EQUIVALENTS

The invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims rather than by the foregoing description, and all changes that come within the meaning and range of equivalency of the claims are therefore intended to be embraced herein.

---

The invention claimed is:

1. A method of loading exosomes with a therapeutically effective amount of an oligonucleotide cargo, said method comprising:

providing oligonucleotides comprising one or more hydrophobic modifications at a concentration of 1.25 µM to 20 µM, wherein the one or more hydrophobic modifications comprise a hydrophobic moiety conjugated to the oligonucleotide;

wherein the hydrophobic moiety is selected from the group consisting of a sterol, GM1, a lipid, a vitamin, a small molecule, a peptide, or a combination thereof; and incubating the oligonucleotides comprising one or more hydrophobic modifications with a population of exosomes, wherein the method takes place in the absence of ultracentrifugation, electroporation and a separately added transfection reagent; thereby loading the exosomes with a therapeutically effective amount of an oligonucleotide cargo;

wherein the therapeutically effective amount is an average of 1000-3000 oligonucleotide molecules per exosome.

2. The method of claim 1, wherein the oligonucleotide is selected from the group consisting of siRNA, siRNA-Gal-NAc, antisense RNA, LNA, hairpin siRNA, PMO, miRNA, miRNA inhibitor and combinations thereof.

3. The method of claim 2, wherein the oligonucleotide is siRNA or miRNA.

4. The method of claim 1, consisting essentially of incubating the oligonucleotides with a population of exosomes.

5. The method of claim 1, wherein loading of the exosomes with the therapeutically effective amount of the oligonucleotide cargo occurs in 30 minutes or less.

6. The method of claim 1, wherein at least 90% of the exosomes in the population of exosomes are loaded with oligonucleotide cargo.

7. The method of claim 1, wherein the hydrophobic moiety is a sterol.

8. The method of claim 7, wherein the hydrophobic moiety is cholesterol.

9. The method of claim 1, wherein the hydrophobic moiety is a vitamin.

10. The method of claim 9, wherein the hydrophobic moiety is Vitamin E.

11. The method of claim 1, wherein the one or more hydrophobic modifications further comprise a backbone modification, a sugar modification, a base modification, or combinations thereof.

12. The method of claim 11, wherein the one or more hydrophobic modifications comprise a backbone modification.

13. The method of claim 12, wherein the backbone modification is selected from the group consisting of phosphorothioate modifications, phosphorodithioate modifications, p-ethoxy modifications, methylphosphonate modifications, methylphosphorothioate modifications, alkyl- and aryl-phosphate modifications, alkylphosphotriester modifications, peptide nucleic acid (PNA) modifications, and locked nucleic acid (LNA) modifications.

14. The method of claim 11, wherein the one or more hydrophobic modifications comprise a sugar modification.

15. The method of claim 14, wherein the sugar is ribose, and wherein the sugar modification comprises 2'O-Methyl, 2'Methoxy-ethyl, 2'Fluor, or 2'FANA.

16. The method of claim 11, wherein the one or more hydrophobic modifications comprise a base modification.

17. The method of claim 16, wherein the base modification is a phenyl modification, a naphthyl modification, or an isobutyl modification.

18. The method of claim 1, wherein the exosomes are derived from cultured cells.

19. The method of claim 18, wherein the exosomes are derived from dendritic cells (DC), immature dendritic cells, B cells, T cells, mast cells, epithelial cells, stem cells, induced pluripotent stem cells (iPS cells), neuronal cells or tumor cells.

20. The method of claim 1, wherein the exosomes are synthetic exosomes.

21. The method of claim 1, wherein the exosomes comprise a targeting peptide.

22. The method of claim 21, wherein the targeting peptide directs the exosomes to neuronal cells.

23. The method of claim 1, wherein the method takes place at a temperature of about 4° C. to about 37° C.

24. The method of claim 1, further comprising purifying the exosomes loaded with the oligonucleotide cargo from unloaded oligonucleotides.

* * * * *